(12) United States Patent
Howard

(10) Patent No.: US 11,957,897 B2
(45) Date of Patent: Apr. 16, 2024

(54) BIOLOGICAL CO-PROCESSOR (BCP)

(71) Applicant: Newton Howard, Providence, RI (US)

(72) Inventor: Newton Howard, Providence, RI (US)

(*) Notice: Subject to any disclaimer, the term of this patent is extended or adjusted under 35 U.S.C. 154(b) by 1158 days.

(21) Appl. No.: 15/495,959

(22) Filed: Apr. 24, 2017

(65) Prior Publication Data

US 2018/0093092 A1  Apr. 5, 2018

Related U.S. Application Data

(60) Provisional application No. 62/397,474, filed on Sep. 21, 2016, provisional application No. 62/353,343, (Continued)

(51) Int. Cl.
| | | |
|---|---|---|
| *A61N 1/05* | (2006.01) | |
| *A61B 5/00* | (2006.01) | |
| *A61L 27/38* | (2006.01) | |
| *A61N 5/06* | (2006.01) | |
| *B82Y 15/00* | (2011.01) | |

(Continued)

(52) U.S. Cl.
CPC .......... *A61N 1/0529* (2013.01); *A61L 27/383* (2013.01); *A61N 5/0622* (2013.01); *B82Y 15/00* (2013.01); *G01N 21/1702* (2013.01); *G01N 27/4145* (2013.01); *A61B 5/0093* (2013.01); *A61N 1/0531* (2013.01); *A61N 5/06* (2013.01); *A61N 2005/0611* (2013.01); *A61N 2005/063* (2013.01); *A61N 5/067* (2021.08); *B82Y 5/00* (2013.01)

(58) Field of Classification Search
CPC ...... A61N 1/0529; A61N 1/0531; A61N 1/06; A61N 5/0622; A61N 2005/0611; A61N 2005/063; A61N 2005/067; A61L 27/383; B82Y 15/00; B82Y 5/00; G01N 21/1702; G01N 27/4145; A61B 5/0093
See application file for complete search history.

(56) References Cited

U.S. PATENT DOCUMENTS 5,862,273 A  1/1999  Pelletier
6,167,298 A  12/2000  Levin
(Continued)

FOREIGN PATENT DOCUMENTS

WO  2013019997 A1  2/2013

OTHER PUBLICATIONS

Hill et al., "Validation of Independent Component Analysis for Rapid Spike Sorting of Optical Recording Data", Innovative Methodology, pp. 3721-3731.

(Continued)

*Primary Examiner* — Eun Hwa Kim
*Assistant Examiner* — Catherine Premraj
(74) *Attorney, Agent, or Firm* — Michael A. Schwartz

(57) ABSTRACT

Embodiments may provide a general-purpose, relatively inexpensive, AI-driven implant that is able to adapt to and modulate any given neuron, circuit, or region in the brain, as well as individual cells of any type of tissue. For example, in an embodiment, a method for interacting with living tissue may comprise attaching a device to a body of a person or animal, the device comprising plurality of carbon fibers in contact with the living tissue, receiving by the carbon fibers signals from the living tissue, processing the received signals by the device, and transmitting the processed signals.

17 Claims, 52 Drawing Sheets

Related U.S. Application Data filed on Jun. 22, 2016, provisional application No. 62/326,007, filed on Apr. 22, 2016.

(51) Int. Cl.
| | |
|---|---|
| *G01N 21/17* | (2006.01) |
| *G01N 27/414* | (2006.01) |
| *A61N 5/067* | (2006.01) |
| *B82Y 5/00* | (2011.01) |

(56) References Cited

U.S. PATENT DOCUMENTS

| | | | |
|---|---|---|---|
| 8,632,577 | B1 | 1/2014 | Bendett |
| 2002/0099412 | A1* | 7/2002 | Fischell ............. A61N 1/36025 607/3 |
| 2004/0133118 | A1 | 7/2004 | Llinas |
| 2005/0032219 | A1 | 2/2005 | Aubourg |
| 2005/0177058 | A1 | 8/2005 | Sobell |
| 2005/0273890 | A1 | 12/2005 | Flaherty |
| 2007/0038307 | A1* | 2/2007 | Webster ................ A61L 31/084 623/23.5 |
| 2008/0007154 | A1 | 1/2008 | Wei |
| 2009/0062676 | A1 | 3/2009 | Kruglikov et al. |
| 2009/0182391 | A1* | 7/2009 | Fowler ................ A61N 1/36082 607/55 |
| 2009/0318825 | A1 | 12/2009 | Kilborn |
| 2010/0098113 | A1 | 4/2010 | Nicholson |
| 2011/0150964 | A1 | 6/2011 | Borck |
| 2012/0094315 | A1 | 4/2012 | Fryar-Williams |
| 2013/0023741 | A1 | 1/2013 | Ayanruoh |
| 2013/0046358 | A1 | 2/2013 | Leyde |
| 2013/0060549 | A1 | 3/2013 | Grimes |
| 2013/0237906 | A1 | 9/2013 | Park |
| 2013/0338526 | A1* | 12/2013 | Howard ................ A61M 21/02 600/544 |
| 2013/0338744 | A1 | 12/2013 | Frewin |
| 2014/0094674 | A1* | 4/2014 | Nurmikko ............ A61B 5/6864 600/378 |
| 2014/0146211 | A1 | 5/2014 | Mori |
| 2014/0148872 | A1 | 5/2014 | Goldwasser |
| 2014/0151733 | A1 | 6/2014 | Koike |
| 2015/0202351 | A1* | 7/2015 | Kaplan ................ A61B 5/6877 607/116 |
| 2016/0030765 | A1* | 2/2016 | Towne ................. A61N 5/0622 607/88 |
| 2016/0120432 | A1 | 5/2016 | Sridhar |
| 2016/0232420 | A1 | 8/2016 | Fan |
| 2017/0164852 | A1 | 6/2017 | Jackson |

OTHER PUBLICATIONS

Hipp et al., "Oscillatory Synchronization in Large Scale Cortical Networks Predicts Perception," Neuron, vol. 69 No. 2, 2011, pp. 387-396.

Ho et al., "Midfield Wireless Powering for Implantable Systems", Proceedings of the IEEE, vol. 101 No. 6, 2013, pp. 1369-1378.

Ho et al., "Wireless power transfer to deep-tissue microimplants" Proceedings of the National Academy of Sciences, vol. 111 No. 22, 2014, pp. 7974-7979.

Hoffmann et al., "Temporal Parameters of Spontaneous Speech in Alzheimer's Disease", International Journal of Speech-Language Pathology, vol. 12 No. 1, 2010, pp. 29-34.

Howard et al., "Computational Methods for Clinical Applications: An Introduction", Functional Neurology, Rehabilitation, and Ergonomics, vol. 1 No. 2, pp. 237-250.

Howard et al., "LXIO: The Mood Detection Robopsych", 2nd International Conference on Biologically Inspired Cognitive Architectures.

Howard N., "Brain Language: The Fundamental Code Unit", The Brain Sciences Journal, vol. 1 No. 1, 2012a, pp. 4-45.

Howard N., "Approach Towards a Natural Language Analysis for Diagnosing Mood Disorders and Comorbid Conditions", Lecture Notes in Computer Science, MICAI, 2013.

May et al., "Detection of Optogenetic Stimulation in Somatosensory Cortex by Non-Human Primates—Towards Artificial Tactile Sensation", PLoS One vol. 9 No. 12, 2014, pp e114529.

Howard, N., "The Twin Hypotheses: Brain Code and the Fundamental Code Unit Springer Lecture Notes in Artificial Intelligence", MICAI , 2013.

Howard et al., "Effect of Impairment on Upper Limb Performance in an Ageing Sample Population Universal Access in Human-Computer Interaction", User and Context Diversity, 2013c, pp. 78-87.

Howard N., "Approach to Study the Brain: Towards the Early Detection of Neurodegenerative Disease", Oxford University, Boldeian Library, 2014.

Howard N., "The Brain Language: Psychotrauma Spectrum Disorder and Cybernetic Detection of Disease Conditions and Comorbidities", Université de Paris Descartes, 2015.

Howard et al., "Combined Modality of the Brain Code Approach for Early Detection and the Long-Term Monitoring of Neurodegenerative Processes", Frontiers Special Issue INCF Course Imaging the Brain at Different Scales, 2013.

Ioannides et al., "Meg Identifies Dorsal Medial Brain Activations During Sleep", Neuroimage, vol. 44 No. 2, 2009, pp. 155-468.

Jäckel et al., "Applicability of Independent Component Analysis On High-Density Microelectrode Array Recordings," 2012, pp. 334-348.

Johnson et al., "Direct Electrical Stimulation of the Somatosensory Cortex in Humans Using Electrocorticography Electrodes: A Qualitative and Quantitative Report", Journal of Neural Engineering, vol. 10 No. 3, 2013.

Kam et al., "Electrical Stimulation of Neural Stem Cells Mediated by Humanized Carbon Nanotube Composite Made with Extracellular Matrix Protein", Nano Letters, vol. 9 No. 1, 2008, pp. 273-278.

Kashiwagi et al., "Deposition of Carbon Nanotubes around Microfiber Via Evanescent Light", Optics Express, vol. 17 No. 20, 2009, pp. 18364-18370.

Keefer et al., "Carbon Nanotube Coating Improves Neuronal Recordings" Nature Nanotechnology, vol. 3 No. 7, 2008, pp. 434-439.

Keller et al., "Sex Differences in the Single Prolonged Stress Mode", Behavioural brain research, vol. 286, 2015, pp. 29-32.

Kelso et al., "Dynamic Cortical Activity in the Human Brain Reveals Motor Equivalence", Nature, vol. 392 No. 6678, 1998, pp. 814-818.

Kim et al., "Point-and-Click Cursor Control with an Intracortical Neural Interface System by Humans with Tetraplegia", Neural Systems and Rehabilitation Engineering, IEEE Transactions on, vol. 19 No. 2, 2011, pp. 193-203.

Kim et al., "Ambulatory Balance Monitoring Using a Wireless Attachable Three-Axis Accelerometer", Journal of Vestibular Research, vol. 23 No. 4-5, 2013, pp. 217-225.

Kohler et al., "Influence of Probe Flexibility and Gelatin Embedding on Neuronal Density and Glial Responses to Brain Implants" PloS one, vol. 10 No. 3, 2015, pp. e0119340.

Kotov et al., "Nanomaterials for Neural Interfaces", Advanced Materials, vol. 21 No. 40, 2009, pp. 3970-4004.

Kringelbach et al., "Translational Principles of Deep Brain Stimulation", Nature Reviews Neuroscience, vol. 8 No. 8, 2007, pp. 623-635.

LaLumiere R. T., "A New Technique for Controlling the Brain: Optogenetics and Its Potential for Use in Research and the Clinic", Brain Stimulation, vol. 4 No. 1, 2011, pp. 1-6.

Lewicki M. S., "A Review of Methods For Spike Sorting: The Detection and Classification of Neural Action Potentials" Network: Computation in Neural Systems, vol. 9 No. 4, 1998, pp. R53-R78.

Liewald et al. "Optogenetic Analysis of Synaptic Function", Nature Methods, vol. 5 No. 10, 2008, pp. 895-902.

Lind et al., "Multiple Implants Do Not Aggravate the Tissue Reaction in Rat Brain" PLoS One, vol. 7 No. 10, 2012, pp. e47509.

Lind et al., "The Density Difference between Tissue and Neural Probes Is a Key Factor for Glial Scarring", Scientific Reports, vol. 3, 2013.

(56) References Cited

OTHER PUBLICATIONS

Liston et al., "Postural Prioritization is Differentially Altered in Healthy Older Compared to Younger Adults During Visual and Auditory Coded Spatial Multitasking" Gait & Posture, 2013.
Lovat et al. "Carbon Nanotube Substrates Boost Neuronal Electrical Signaling", Nano Letters, vol. 5 No. 6, 2005, pp. 1107-1110.
Ma et al., "Midfield Wireless Power Transfer for Bioelectronics", IEEE Circuits and Systems Magazine, vol. 15 No. 2, 2015, pp. 54-60.
Madany et al., "Unsupervised Spike Sorting With ICA and its Evaluation Using Genesis Simulations," Neurocomputing, vol. 66, 2005, pp. 275-282.
Macknik et al., "Optical Images of Visible and Invisible Percepts in the Primary Visual Cortex of Primates", PNAS, vol. 96, 1999, pp. 15208-15210.
Makarov et al., "Disentanglement of Local Field Potential Sources by Independent Component Analysis," 2010, pp. 445-457.
Martin et al., "A User-Centred Approach to Requirements Elicitation in Medical Device Development: A Case Study from an Industry Perspective", Applied Ergonomics, vol. 43 No. 1, 2012, pp. 184-190.
Marty et al., "Executive Function And Activities Of Daily Living In Alzheimer's Disease:A Correlational Meta-Analysis", Dementia and Geriatric Cognitive Disorders, vol. 33 No. 2-3, 2012, pp. 189-203.
McKenzie et al., "Decreased Functions of Astrocytes on Carbon Nanofiber Material" Biomaterials, vol. 25 No. 7, 2004, pp. 1309-1317.
Mijovic, B., "Source Separation From Single-Channel Recordings by Combining Empirical-Mode Decomposition and ICA," vol. 57 No. 9, 2010, pp. 2188-2196.
Minnikanti et al., "Implantable Electrodes with Carbon Nanotube Coatings,": INTECH Open Access Publisher, 2011.
Mirbozorgi et al., "A Single-Chip Full-Duplex High Speed Transceiver for Multi-Site Stimulating and Recording Neural Implants," in IEEE Transactions on Biomedical Circuits and Systems, vol. 10 No. 3, 2016, pp. 643-653.
Montgomery et al., "Wirelessly Powered, Fully Internal Optogenetics for Brain, Spinal and Peripheral Circuits In Mice", Nature Methods, vol. 12 No. 10, 2015, pp. 969-974.
Morin et al., "Modeling Dyskinesia in Animal Models of Parkinson Disease", Experimental Neurology, vol. 256, 2014, pp. 105-116.
Mukamel et al., "Coupling Between Neuronal Firing, Field Potentials, and FMRI in Human Auditory Cortex" Science, vol. 309 No. 5736, 2005, pp. 951-954.
Nedelcovych et al., "A Rodent Model of Traumatic Stress Induces Lasting Sleep and Quantitative Electroencephalographic Disturbances" ACS Chemical Neuroscience, vol. 6 No. 3, 2015, pp. 485-493.
Nicolelis et al., "Chronic, Multisite, Multielectrode Recordings in Macaque Monkeys" Proceedings of the National Academy of Sciences, vol. 100 No. 19, 2003, pp. 11041-11046.
Niiyama et al., "Sticky Actuator: Free-Form Planar Actuators for Animated Objects", Paper presented at the Proceedings of the Ninth International Conference on Tangible, Embedded, and Embodied Interaction, 2015.
Nir et al., "Bold and Spiking Activity" Nature Neuroscience, vol. 11 No. 5, 2008, pp. 523-524.
Nir et al., "Widespread Functional Connectivity and Fmri Fluctuations in Human Visual Cortex in the Absence of Visual Stimulation", Neuroimage, vol. 30 No. 4, 2006, pp. 1313-1324.
Nishimoto et al., "Reconstructing Visual Experiences from Brain Activity Evoked by Natural Movies", Current Biology, vol. 21 No. 19, 2011, pp. 1641-1646.
Nolta et al., "Bbb Leakage, Astrogliosis, and Tissue Loss Correlate with Silicon Microelectrode Array Recording Performance" Biomaterials, vol. 53, 2015, pp. 753-762.
Nunes et al., "Application of Carbon Nanotubes in Neurology: Clinical Perspectives and Toxicological Risks", Archives of toxicology, vol. 86 No. 7, 2012, pp. 1009-1020.
Ochsner et al., "Micro-Well Arrays for 3d Shape Control and High Resolution Analysis of Single Cells" Lab on a Chip, vol. 7 No. 8, 2007, pp. 1074-1077.
Owen et al., "Deep Brain Stimulation for Neuropathic Pain" ACTA Neurochirurgica-Supplementum Then Supplement-Wien, vol. 97 No. 2, 2007, pp. 111.
Pasley et al., "Reconstructing Speech from Human Auditory Cortex", PLoS Biology, vol. 10 No. 1, 2012, pp. e1001251.
Penfield et al., "Somatic Motor and Sensory Representation in the Cerebral Cortex of Man as Studied by Electrical Stimulation", Brain, vol. 60, 1937, pp. 38-443.
Perlovsky, L. I. "Vague-to-Crisp" Neural Mechanism of Perception Neural Networks, IEEE Transactions on, vol. 20 No. 8, 2009, pp. 1363-1367.
Pillow et al., "A Model-Based Spike Sorting Algorithm for Removing Correlation Artifacts in Multi-Neuron Recordings", PloS one, vol. 8 No. 5, 2013, pp. e62123.
Prausnitz et al., "Transdermal Drug Delivery" Nature Biotechnology, vol. 26 No. 11, 2008, pp. 1261-1268.
Rajangam et al., "Wireless Cortical Brain-Machine Interface for Whole-Body Navigation in Primates", Scientific Reports, vol. 6, 2016.
Rajput et al., "Cell Interaction Study Method Using Novel 3d Silica Nanoneedle Gradient Arrays", Colloids and Surfaces B: Biointerfaces, vol. 102, 2013, pp. 111-116.
SCENIHR (Scientific Committee on Emerging and Newly Identified Health Risks), "Risk Assessment of Products of Nanotechnologies", Europa: European Comission, 2009.
Rey et al., "Past, Present and Future of Spike Sorting Techniques" Brain Research Bulletin, vol. 119, 2015, pp. 106-117.
Rieiro et al. "Perceptual Elements in Penn & Teller's "Cups and Balls" Magic Trick", PeerJ , vol. 1, 2013, pp. e19.
Rousche et al., "Chronic Recording Capability of the Utah Intracortical Electrode Array in Cat Sensory Cortex" Journal of Neuroscience Methods, vol. 82 No. 1, 1998, pp. 1-15.
Ruther et al., "New Approaches for CMOS-Based Devices for Large-Scale Neural Recording", Current Opinion in Neurobiology, vol. 32, 2015, pp. 31-37.
Rutten et al., "Neuro-Electronic Interfacing with Multielectrode Arrays", Engineering in Medicine and Biology Magazine, IEEE, vol. 18 No. 3, 1999, pp. 47-55.
Sartory et al., "In Search of the Trauma Memory: A Meta-Analysis of Functional Neuroimaging Studies of Symptom Provocation in Posttraumatic Stress Disorder (Ptsd)", PloS one, vol. 8 No. 3, 2013, pp. e58150.
Scepanovic et al., "Design and Processing of High-Density Single-Mode Fiber Arrays for Imaging and Parallel Interferometer Applications", Applied optics, vol. 43 No. 21, 2004, pp. 4150-4156.
Seidl et al., "CMOS-Based High-Density Silicon Microprobe Arrays for Electronic Depth Control in Intracortical Neural Recording", Journal of Microelectromechanical Systems, vol. 20 No. 6, 2011, pp. 1439-1448.
Serruya et al., "The Braingate Pilot Trial: Building and Testing a Novel Direct Neural Output for Patients with Severe Motor Impairment", Society for Neuroscience, 2004.
Shenk D., "Welcome to the Body-Wide Web", Nature Biotechnology, vol. 24 No. 3, 2006, pp. 282-283.
Shepherd G. M., "Corticostriatal Connectivity and Its Role in Disease", Nature Reviews Neuroscience, vol. 14 No. 4, 2013, pp. 278-291.
Shulman et al., "Subjective Report Versus Objective Measurement of Activities of Daily Living in Parkinson's Disease", Movement Disorders, vol. 21 No. 6, 2006, pp. 794-799.
Silva G. A., "Neuroscience Nanotechnology: Progress, Opportunities and Challenges", Nature Reviews Neuroscience, vol. 7 No. 1, 2006, pp. 65-74.
Smith, K., "Nanotube 'Shortcut ' Boosts Brain Signals", Nature News, Nov. 2008.
Sokolova et al., "Beyond Accuracy, F-Score and ROC: A Family of Discriminant Measures for Performance Evaluation", Advances in Artificial Intelligence , vol. 4304, 2006, pp. 1015-1021.

(56) References Cited

OTHER PUBLICATIONS

Sorkin et al., "Process Entanglement as a Neuronal Anchorage Mechanism to Rough Surfaces", Nanotechnology, vol. 20 No. 1, 2008, pp. 015101.
Sotnikov et al., "Implementation of Dynamic Logic Algorithm for Detection of Em Fields Scattered by Langmuir Soliton", 2012.
Stanley et al., "Reconstruction of Natural Scenes from Ensemble Responses in the Lateral Geniculate nucleus", Journal Neuroscience, vol. 19, 1999, pp. 8036-8042.
Stoy et al. "High Yield Subcortical Patch Clamping in Vivo", Biophysical Journal, vol. 3 No. 110, 2016, pp. 149a.
Subbaroyan et al., "The Role of Flexible Polymer Interconnects in Chronic Tissue Response Induced by Intracortical Microelectrodes-a Modeling and an in Vivo Study", Paper presented at the Engineering in Medicine and Biology Society, 2006.
Sucapane et al., "Interactions between Cultured Neurons and Carbon Nanotubes: A Nanoneuroscience Vignette", Journal of Nanoneuroscience, vol. 1 No. 1, 2009, pp. 10.
Suzuki et al., "Carbon Nanotube Multi-Electrode Array Chips for Noninvasive Real-Time Measurement of Dopamine, Action Potentials, and Postsynaptic Potentials", Biosensors and Bioelectronics, vol. 49, 2013, pp. 270-275.
Takahashi et al., "A New Approach to Spike Sorting for Multi Neuronal Activities Recorded with a Tetrode—How ICA Can Be Practical," Neuroscience Research, vol. 46 No. 3, 2003, pp. 265-272.
De Waal FB et aal., "Towards a Bottom-Up Perspective on Animal and Human Cognition", Trends in Cognitive Sciences, vol. 14 No. 5, May 2010, pp. 2017.
Diederik Aerts., "Quantum Structure in Cognition", Journal of Mathematical Psychology, vol. 53 No. 5, Oct. 2009, pp. 314-348.
Lamb, Sydney., "On the Neurocognitive Basis of Language." Wenzao suline College of Languages, 2010.
Blais et al., "The Physics of the Brain: Towards an Understanding of Learning and Memory", Brown University Laboratory talk, Dec. 2011.
Penrose, Roger. "The Emperor's New Mind" (1991 ). New York: Penguin Books (1991).
J. Qusaibaty et al., "Intention Awareness in the Nutshell." Defense Concepts, Aug. 2004.
Baslow, Morris H. "The Languages of Neurons: An Analysis of Coding Mechanisms by Which Neurons Communicate, Learn and Store Information." Entropy, vol. 11, 2009, pp. 782-797.
New Boris et al., "Differential Processing of Consonants and Vowels in Lexical Access through Reading", Association for Psychological Science, vol. 19 No. 2, 2008.
Sanghvi, Natalie et al., "Activity of Spiking Neurons Stimulated by External Signals of Different Wave", 4th CSI Undergraduate Research Conference of the College of Staten Island, Book of Abstracts, 2005, pp. 32.
McFadden et al., "Synchronous Firing and Its Influence on the Brain's Electromagnetic Field: Evidence for an Electromagnetic Field Theory of Consciousness", Journal of Consciousness Studies, vol. 9 No. 4, 2002, pp. 23-50.
Solms et al., "The Brain and the Inner World: An Introduction to the Neuroscience of Subjective Experience", Other Press, 2002.
McMurry, John. "Organic Chemistry (7th Edition)", Thomson Books/Cole, 2008.
Crossley, Roger., "Chirality and the Biological Activity of Drugs", CRC-Press, 1995.
Pinel, John J., "Biopsychology, 6th Ed", Pearson Education, Inc., 2006.
Spitzer et al. "Enantio-Selective Cognitive and Brain Activation Effects of N-Ethyl-3.4-Methylenedioxymethamphetamine in Humans". Neuropharmalacology, vol. 41, 2001, pp. 263-271.
Kaiser, Gary E., "Structure of DNA", CCBC Faculty Webpages, 2011.
Shannon C et al., "The Mathematical Theory of Communication", University of Illinois Press, 1963.

Hoskins et al., "Diagnostic Ultrasound: Physics and Equipment", Greemvich Medical Media, 2010.
Rinaldi et al., "Modification by Focused Ultrasound Pulses of Electrically Evoked Responses from an In-Vitro Hippocampal Preparation", Brain Research, vol. 558, 1991, pp. 36-42.
Weibeld et al., "Symmorphosis: On Form and Function information Japing Life", Harvard University Press, Cambridge, MA. 2000.
Y Cajal et al., "Histology of tile Nervous System of Man and Vertebrates", Oxford University Press, 1995.
Mitchison Graeme., "Neuronal Branching Patterns and idle Economy of Cortical Wiring", Proceedings of Royal Society, vol. 245 No. 1313, 1991, pp. 151-158.
Koukalov et al., "Orientation Preference Patterns in Mammalian Visual Cortex: A Wire Length Minimization Approach", Neuron, vol. 29, Feb. 2001, pp. 519-527.
Hsu, Jeremy., "How Much Power Does the Human Brain Require to Operate?", Popular Science, Nov. 2009.
Kety SS., "The General Metabolism of the Brain In Vivo in: Metabolism of the Nervous System", London: Pergamon, 1957, pp. 221-223.
Sokoloffl., "The Metabolism of the Central Nervous System In Vivo. In: Handbook Of Physiology", Section I, Neurophysiology, vol. 3, 1960, pp. 1843-1864.
Rolfe., "Cellular Energy Utilization and Molecular Origin of Standard Metabolic Rate In Mammals", Physiology Reviews, vol. 77, 1997, pp. 731-758.
Aiello et al., "In Defense of Expensive Tissue Hypothesis. In Evolutionary Anatomy of the Primate Cerebral Cortex", Cambridge: Cambridge University Press, 2001, pp. 57-78.
Crespi et al., "Comparative Genomics of Autism and Schizophrenia" Proceedings of the National Academy of Sciences (PNAS). Early Edition Sep. 2009.
Simoncelli et al., "Natural Image Statistics and Neural Representation" Annual Review of Neuroscience, vol. 24, 2001, pp. 1193-1121.
Baddeley, Alan., "The Central Executive: A Concept and Some Misconceptions." Journal of the International Neuropsychological Society, vol. 4, 1998, pp. 523-552.
Balasubramanian et al., Metabolically Efficient Information Processing, Neural Computation , vol. 13, 2001, pp. 799-815.
David J., "What is the Goal of Sensory Coding?" Cornell University (Dept.of Psychology), 1994.
Levy et al., "Energy-Efficient Neural Codes", Neural Computation, vol. 8, 1996, pp. 531-543.
Atwell et al., "An Energy Budget for Signaling in the Grey Matter of the Brain", Journal of Cerebral Blood Flow and Metabolism, vol. 21, 2001, pp. 1133-1145.
F Frohlichand et al., "Endogenous Electric Fields May Guide Neocortical Network Activity", Neuron, vol. 67 No. 1, Jul. 2010, pp. 129-143.
Hunt L et al., "Mechanisms Underlying Cortical Activity Dming Value-Guided Choice", Nature Neuroscience, 2012.
Kennerley S. et al., "Double Dissociation of Value Computations in Orbitofrontal and Anterior Cingulate Neurons", Nature Neuroscience, 2011.
Qu et al., "A Patient-Specific Algorithm for the Detection of Seizure Onset in Long-Term EEG Monitoring: Possible Use as a Warning Device", IEEE Transactions On Biomedical Engineering, vol. 44, No. 2, Feb. 1997.
Hameroff S. "Orchestrated Reduction of Quantum Coherence in Brain Microtubules A Model for Consciousness", NeuroQuantology, vol. 5, Issue 1, Mar. 2007, pp. 1-8.
The Brain Sciences Journal, The Official Journal of The Brain Sciences Foundation, vol. 1, No. 1, Mar. 2012, pp. 92.
Torfs et al., "Two-Dimensional Multichannel Neural Probes with Electronic Depth Control", Biomedical Circuits and Systems, IEEE Transactions on, vol. 5 No. 5, 2011, pp. 403-412.
Hameroff, Stuart & Roger Penrose, In: Toward a Science of Consciousness—The First Tucson Discussions and Debates, eds. Hameroff, S.R., Kaszniak, A.W. and Scott, A.C., Cambridge, MA: MIT Press, pp. 507-540 (1996).

(56) References Cited

OTHER PUBLICATIONS

Lee et al., "Multifunctional Transparent Opto Electrode Array for in-Vivo Optogenetic Studies", Paper presented at the CLEO: Applications and Technology, 2015.
Mei et al., "Miniaturizing wireless implants" Nature Biotechnology, vol. 32 No. 10, 2014, pp. 1008-1010.
Takekawa et al., "Spike Sorting of Heterogeneous Neuron Types by Multimodality Weighted PCA and Explicit Robust Variational Bayes," vol. 6, 2012, pp. 1-13.
Tannenholz et al., "Local and Regional Heterogeneity Underlying Hippocampal Modulation of Cognition and Mood", Frontiers in behavioral neuroscience, vol. 8, 2014.
Teng et al., "Persistence of Neuropsychological Testing Deficits in Mild Cognitive Impairment", Dement Geriatr Cogn Disord, vol. 28 No. 2, 2009, pp. 168-178.
Thelin et al., "Implant Size and Fixation Mode Strongly Influence Tissue Reactions in the CNS", PloS one, vol. 6 No. 1, 2011, pp. e16267.
Thies et al., "Movement Variability in Stroke Patients and Controls Performing Two Upper Limb Functional Tasks: A New Assessment Methodology", Journal of NeuroEngineering and Rehabilitation, vol. 6 No. 2, 2009.
Thoma et al., "Automatic Detection and Rating of Dementia of Alzheimer Type Through Lexical Analysis of Spontaneous Speech", Paper Presented at the Mechatronics and Automation, 2005.
Tigan et al., "Neural Spike Sorting Using Iterative ICA and a Deflation Based Approach," Journal of Neural Engineering, vol. 9 No. 6, 2012, pp. 066002.
Tufail et al., "Transcranial Pulsed Ultrasound Stimulates Intact Brain Circuits Neuron," vol. 66 No. 5, 2010, pp. 681-694.
Uswatte et al., "Reliability and Validity of the Upper-Extremity Motor Activity Log-14 for Measuring Real-World Arm Use", Stroke, vol. 36 No. 11, 2005, pp. 2493-2496.
Van Dulmen et al., "Patient Adherence to Medical Treatment: a Review of Reviews", BMC Health Services Research, vol. 7 No. 1, 2007, pp. 55.
Vann et al., "What Does the Retrosplenial Cortex Do?" Nature Reviews, Neuroscience, vol. 10 No. 11, 2009, pp. 792-802.
Vitale et al., "Neural Stimulation and Recording with Bidirectional, Soft Carbon Nanotube Fiber Microelectrodes", ACS Nano, vol. 9 No. 4, 2015, pp. 4465-4474.
Voge et al., "Carbon Nanotubes in Neural Interfacing Applications", Journal of Neural Engineering, vol. 8 No. 1, 2011, pp. 011001.
Waldemar et al., "Recommendations for the Diagnosis and Management of Alzheimer's Disease and Other Disorders Associated with Dementia: EFNS Guideline", European Journal of Neurology, vol. 14 No. 1, 2007, pp. e1-e26.
Wang et al., "Effects of Carbon Nanotubes on Rat Liver and Brain", NANO, vol. 9 No. 7, 2014, pp. 1450083.
Wang et al., "Functionalized Carbon Nanotubes: Revolution in Brain Delivery", Nanomedicine, vol. 10 No. 17, 2015, pp. 2639-2642.
Wang et al., "Neural Stimulation with a Carbon Nanotube Microelectrode", Array Nano letters, vol. 6 No. 9, 2006, pp. 2043-2048.
Wild et al., "Performance Comparison of Extracellular Spike Sorting Algorithms for Single Channel Recordings," Journal of Neuroscience Methods, vol. 203 No. 2, 2012, pp. 369-376.
Williams et al., "Long-Term Neural Recording Characteristics of Wire Microelectrode Arrays Implanted in Cerebral Cortex", Brain Research Protocols, vol. 4 No. 3, 1999, pp. 303-313.
Wilson et al., "Valproic Acid Effects in the Hippocampus and Prefrontal Cortex in an Animal Model of Post-Traumatic Stress Disorder", Behavioural brain research, vol. 268, 2014, pp. 72-80.
Winslow et al., "A Comparison of the Tissue Response to Chronically Implanted Parylene-C-Coated and Uncoated Planar Silicon Microelectrode Arrays in Rat Cortex", Biomaterials, vol. 31 No. 35, 2010, pp. 9163-9172.
Winslow et al., "Quantitative Analysis of the Tissue Response to Chronically Implanted Microwire Electrodes in Rat Cortex", Biomaterials, vol. 31 No. 7, 2010, pp. 1558-1567.
Wise K. D., "Silicon Microsystems for Neuroscience and Neural Prostheses", Engineering in Medicine and Biology Magazine, IEEE, vol. 24 No. 5, 2005, pp. 22-29.
Yamada et al., "A Stretchable Carbon Nanotube Strain Sensor for Human-Motion Detection", Nature Nanotechnology, vol. 6 No. 5, 2011, pp. 296-301.
Yi et al., "A Flexible and Implantable Microelectrode Arrays Using High-Temperature Grown Vertical Carbon Nanotubes and a Biocompatible Polymer Substrate", Nanotechnology, vol. 26 No. 12, 2015, pp. 125301.
Zariwala et al., "A Cre-Dependent GCaMP3 Reporter Mouse for Neuronal Imaging In Vivo", Journal Neuroscience, vol. 32, 2012, pp. 3131-3141.
Zhang et al., "Multimodal Fast Optical Interrogation of Neural Circuitry", Nature, vol. 446 No. 7136, 2007, pp. 633-639.
Zhang et al., "Carbon Nanotube Uptake and Toxicity in the Brain", Carbon Nanotubes: Methods and Protocols, 2010, pp. 55-65.
Zhang et al., "Fault Detection of Non Gaussian Processes Based on Modified Independent Component Analysis," Chemical Engineering Science, vol. 65 No. 16, 2010, pp. 4630-4639.
Zhao et al., "Functional Graphene Nanomesh Foam", Energy & Environmental Science, vol. 7 No. 6, 2014, pp. 1913-1918.
Zhou et al., "Use of Multiple Wearable Inertial Sensors in Upper Limb Motion Tracking" Medical Engineering & Physics, vol. 30 No. 1, 2008, pp. 123-133.
Zhou et al., "Poly (3, 4-Ethylenedioxythiophene)/Multiwalled Carbon Nanotube Composite Coatings for Improving the Stability of Microelectrodes in Neural Prostheses Applications", Acta biomaterialia, vol. 9 No. 5, 2013, pp. 6439-6449.
Montgomery et al., "Wirelessly Powered, Fully Internal Optogenetics for Brain, Spinal and Peripheral Circuits in Mice", Nature Methods, vol. 12 No. 10, 2015, 969-974.
Bjarkam et al., "Neuromodulation in a Minipig MPTP Model of Parkinson Disease", British Journal of Neurosurgery, vol. 22 No. Suppl 1, 2008, pp. S9-S12.
Ahmed et al., "Efficient Delivery of Cre-Recombinase to Neurons in Vivo and Stable Transduction of Neurons Using Adeno-Associated and Lentiviral Vectors" BMC Neuroscience, vol. 5 No. 4, 2004.
Klapoetke et al., "Independent Optical Excitation of Distinct Neural Populations", Nature Methods, vol. 11 No. 3, Mar. 2014, pp. 338-346.
Sun et al., "Single-chip Microprocessor that Communicates Directly Using Light", Nature, vol. 24 No. 528, 2015, pp. 534-538.
Shipton et al., "Left-Right Dissociation of Hippocampal Memory Processes in Mice", Proceedings of the National Academy of Sciences of the United States of America, vol. 111 No. 42, 2014, pp. 15238-15243.
Kohl et al., "Hemisphere-Specific Optogenetic Stimulation Reveals Left-Right Asymmetry of Hippocampal Plasticity", Nature Neuroscience, vol. 14 No. 11, 2011, pp. 1413-1415.
Diester et al., "An Optogenetic Toolbox Designed For Primates", Nature Neuroscience, vol. 14 No. 3, 2011, pp. 387-397.
Howard et al., "Tropism and Toxicity of Adeno-Associated Viral Vector Serotypes 1, 2, 5, 6, 7, 8, And 9 in Rat Neurons and Glia in Vitro", Virology, vol. 372 No. 1, 2008, pp. 24-34.
Xu et al., "Quantitative Comparison of Expression with Adeno-Associated Virus (AAV-2) Brain-Specific Gene Cassettes", Gene Therapy, vol. 8 No. 17, 2001, pp. 1323-1332.
Sapolsky, Robert., "This Is Your Brain on Metaphors", New York Times, 2010.
Wang et al., "Information and Knowledge Representation in the Brain." Proceedings of the Second IEEE International Conference on Cognitive Infonnatics. 2003, pp. 1-6.
Guarino, Nicola. "Formal Ontology, Conceptual Analysis and Knowledge Representation." Int. Hwnan-ComputerStudies, vol. 43, 1995, pp. 625-640.
Gero, John S. "Design Prototypes: A Knowledge Representation Schema for Design." Al Magazine , vol. 11 No. 4, 1990 pp. 26-36.

(56) References Cited

OTHER PUBLICATIONS

Block H.D. "The Perceptron: A Model for Brain Functioning I", Reviews of a Modern Physics, vol. 34 No. 1, Jan. 1962, pp. 123-137.
Anderson et al., "The Atomic Components of Thought," Lawrence Erlbaum Associates, Mahwah, 1998.
Ahmed et al. "Efficient Delivery of Cre-Recombinase to Neurons in Vivo and Stable Transduction of Neurons Using Adeno-Associated and Lentiviral Vectors", BMC Neuroscience, vol. 5, 2004.
Anderson et al., "Improved Signal and Reduced Noise in Neural Recordings from Close Spaced Electrode Arrays Using Independent Component Analysis as a Preprocessor," vol. 150, 2006, pp. 254-264.
Ayzenshtat et al., Population Response to Natural Images in the Primary Visual Cortex Encodes Local Stimulus Attributes and Perceptual Processing, The Journal of Neuroscience, vol. 32, 2012, pp. 13971-13986.
Bai et al., "Graphene Nanomesh", Nature Nanotechnology, vol. 5 No. 3, 2010, pp. 190-194.
Bar et al., "Top-Down Facilitation of Visual Recognition", Proceedings of the National Academy of Sciences of the United States of America, vol. 103 No. 2, 2006, pp. 449-454.
Bardi et al., "Pluronic-Coated Carbon Nanotubes Do Not Induce Degeneration of Cortical Neurons in Vivo and in Vitro", Nanomedicine: Nanotechnology, Biology and Medicine, vol. 5 No. 1, 2009, pp. 96-104.
Bareket-Keren et al., "Carbon Nanotube-Based Multi Electrode Arrays for Neuronal Interfacing: Progress and Prospects", Front Neural Circuits, vol. 6 No. 122, 2013.
Harrison et al., "Carbon Nanotube Applications for Tissue Engineering", Biomaterials, vol. 28 No. 2, 2007, pp. 344-353.
Bareket-Keren et al., "Novel Interfaces for Light Directed Neuronal Stimulation: Advances and Challenges", International Journal of Nanomedicine, vol. 9, 2014b, pp. 65-83.
Barra et al., "Increasing cognitive load with increasing balance challenge: recipe for catastrophe", Experimental Brain Research, vol. 174 No. 4, 2006, pp. 734-745.
Barton et al., "Movement Disorders Caused by Medical Disease", Paper Presented at the Seminars in Neurology, 2009.
Bellamkonda et al,. "Materials for Neural Interfaces", MRS Bulletin, vol. 37 No. 6, 2012, pp. 557-561.
Belyanskaya et al., "Effects of Carbon Nanotubes on Primary Neurons and Glial Cells", Neurotoxicology, vol. 30 No. 4, 2009, pp. 702-711.
Wierzbicka, Anna. 1996. Semantics: Primes and Universals. Oxford: Oxford University Press. (1996).
Bergmann et al., "Wearable and Implantable Sensors: The Patient's Perspective", Sensors, vol. 12 No. 12, 2012, pp. 16695-16709.
Bergmann et al., "Body-worn sensor design: what do patients and clinicians want?" Annals of Biomedical Engineering, vol. 39 No. 9, 2011, pp. 2299-2312.
Bergmann et al., "Procedural Differences Directly Affect Timed Up and Go Times", Journal of the American Geriatrics Society, vol. 57 No. 1, 2009, pp. 2168-2169.
Bergmann et al,. "Exploring the Use of Sensors to Measure Behavioral Interactions: An Experimental Evaluation of Using Hand Trajectories", PLoS One, vol. 9 No. 2, 2014, pp. e88080.
Bergmann et al,. "A Portable System for Collecting Anatomical Joint Angles During Stair Ascent: A Comparison With an Optical Tracking Device", Dynamic Medicine, vol. 8 No. 1, 2009, pp. 3.
Bergmann et al,. "Using a Body Sensor Network to Measure the Effect of Fatigue on Stair Climbing Performance", Physiological Measurement, vol. 33 No. 2, 2012, pp. 287.
Bergmann et al,. "An Attachable Clothing Sensor System for Measuring Knee Joint Angles", Sensors Journal, IEEE, vol. 13 No. 10, 2013, 4090-4097.
Bergmann et al., "The "Wear and Measure" Approach: Linking Joint Stability Measurements from a Smart Clothing System to Optical Tracking", Journal of Sensors, vol. 8, 2015.
Bergmann et al., "Comparison of Median Frequency Between Traditional and Functional Sensor Placements During Activity Monitoring", Measurement, vol. 46 No. 7, 2013, pp. 2193-2220.
Kalat, James W. Introduction to Psychology. 8th Ed. WadsWorth Publishing. (2007).
Biran et al., "Neuronal Cell Loss Accompanies the Brain Tissue Response to Chronically Implanted Silicon Microelectrode Arrays", Experimental Neurology, vol. 195 No. 1, 2005, pp. 115-126.
Bonato P., "Wearable Sensors and Systems", IEEE Engineering in Medicine and Biology Magazine, vol. 29 No. 3, 2005, pp. 25-36.
Boyden E. "A History of Optogenetics: The Development of Tools for Controlling Brain Circuits with Light", 2011.
Boyden et al., "Millisecond-Timescale, Genetically Targeted Optical Control of Neural Activity", Nature neuroscience, vol. 8 No. 9, 2005, pp. 1263-1268.
Boyle et al., "See the Light: Can Optogenetics Restore Healthy Heartbeats? And, If It Can, Is It Really Worth the Effort?", Expert review of cardiovascular therapy, vol. 12 No. 1, 2014, pp. 17-20.
Brown et al., "Independent Component Analysis at the Neural Cocktail Party," vol. 24 No. 1, 2001, pp. 54-63.
Bruggemann et al., "Automated Patch Clamping of 384 Cells at Once for Massively Parallel lon Channel Screening", Biophysical Journal, vol. 106 No. 2, 2014, pp. 132a.
Canolty et al,. "Oscillatory Phase Coupling Coordinates Anatomically Dispersed Functional Cell Assemblies," Proceedings of the National Academy of Sciences of the United States of America, vol. 107 No. 40, 2010, pp. 17356-17361.
Chah et al., "Automated Spike Sorting Algorithm Based on Laplacian Eigenmaps and K Means Clustering," Journal of Neural Engineering, vol. 8, 2011, pp. 016006.
Chen et al., "An Active, Flexible Carbon Nanotube Microelectrode Array for Recording Electrocorticography" Journal of Neural Engineering, vol. 8 No. 3, 2011, pp. 034001.
Cohen et al., "Explaining a Complex Living System: Dynamics, Multi-Scaling and Emergence", Journal of the Royal Society Interface, vol. 4 No. 13, 2007, pp. 175-182.
Davis et al., "Caregivers' Perceptions of Dementia Patients' Functional Ability", American Journal of Alzheimer's Disease & Other Dementias, vol. 21 No. 2, 2006, pp. 85-91.
Deisseroth, K., "Optogenetics", Nature methods, vol. 8 No. 1, 2011, pp. 26-29.
Deisseroth, K., "Controlling the brain with light", Scientific American, vol. 303 No. 5, 2010, pp. 48-55.
Erdfelder et al,. "GPOWER: A General Power Analysis Program", Behavior Research Methods, vol. 28 No. 1, 1996, pp. 1-11.
Fenno et al., "The Development and Application of Optogenetics", Neuroscience, vol. 34 No. 1, 2011, pp. 389.
Fitch et al., "Cns Injury, Glial Scars, and Inflammation: Inhibitory Extracellular Matrices and Regeneration Failure", Experimental Neurology, vol. 209 No. 2, 2008, pp. 294-301.
Frackowiak et al., "The Future of Human Cerebral Cartography: A Novel Approach", Philosophical Transactions of the Royal Society of London B: Biological Sciences, vol. 370 No. 1668, 2015, pp. 20140171.
Freeman et al., "Mapping Brain Activity at Scale With Cluster Computing," Nature Methods, vol. 11, 2014, pp. 941-950.
Freeman J., "Open Source Tools for Large Scale Neuroscience," Current Opinion in Neurobiology, vol. 32, 2015, pp. 156-163.
Gabriel et al., "Easily Made Single-Walled Carbon Nanotube Surface Microelectrodes for Neuronal Applications", Biosensors and Bioelectronics, vol. 24 No. 7, 2009, pp. 1942-1948.
Gerits et al., "Optogenetically Induced Behavioral and Functional Network Changes in Primates", Current Biology, vol. 22 No. 18, 2012, pp. 1722-1726.
Gorelik et al., "Ion Channels in Small Cells and Subcellular Structures Can Be Studied with a Smart Patch-Clamp System", Biophysical Journal, vol. 83 No. 6, 2002, pp. 3296-3303.
Grosenick et al., "Closed-Loop and Activity-Guided Optogenetic Control", Neuron, vol. 86 No. 1, 2015, pp. 106-139.
Hammond et al., "Pathological Synchronization in Parkinson's Disease: Networks, Models and Treatments", Trends in neurosciences, vol. 30 No. 7, 2007, pp. 357-364.

(56) References Cited

OTHER PUBLICATIONS

Campbell, Neil A., Brad Williamson, and Robin J. Heyden Biology 91 Chapter 2, Section 2.2. Boston, Massachusetts: Pearson Prentice Hall. (2010) Edition (2010).

* cited by examiner

Fig. 6

| Laser Advantages | Laser Disadvantages |
|---|---|
| • Narrow spectral linewidth of 0.1 nm or better means that there is no chance of cross-talk and no need for additional filtering.<br>• Directional output results in high coupling efficiency in the range of 85-90%. Allows for additional optical components in the beam path.<br>• If not using fiber optics for beam delivery, it is easy to direct high intensity light to the target site in free space.<br>• Best choice when high intensity or wavelength specificity is required | • Laser modules are more bulky than LEDs and cannot be mounted directly to a subject animal.<br>• Instability in the pulse shape when directly modulating sometimes necessitates an external modulator.<br>• Size of hardware and connectors |
| LED Advantages | LED Disadvantages |
| • Can be directly modulated at high speed with little degradation in pulse shape.<br>• Very small and light, can be mounted directly on an animal's head for direct stimulation.<br>• Specifications for stability and optical noise are inherently low<br>• Small size required for extremely high density probe. | • LEDs output in all directions, so it is much harder to couple high power levels into optical fiber. 20-30 mW is a typical maximum throughput for a multi-Watt blue LED coupled to optical fiber. This figure is even lower for green and yellow LEDs.<br>• Wide spectral linewidth of 10-30 nm makes it harder to eliminate cross-talk.<br>• Additional filters may be required to remove unwanted wavelengths, but these will reduce the total power even further. |

Fig. 7

| CNT Advantages | CNT Disadvantages |
|---|---|
| • Electrical conductor/optical fiber dual functionality.<br>• Small size required for extremely high density probe.<br>• Excellent conducting properties<br>• CNT are nanoscale, strong, tough, flexible, biocompatible and non-faradaic while also having both high electrical conductivity and high surface area (Bareket-Keren, L. & Hanein, Y., 2012; Bareket-Keren, L. & Hanein, Y., 2014a; Kotov, N.A. et al., 2009; Voge, C.M. & Stegemann, J.P., 2011).<br>• CNT can allow for the use of smaller electrodes by reducing impedance, thus improving signal-to-noise ratios (Minnikanti, S. & Peixoto, N., 2011). | • Fragile and potentially difficult to handle in a clinical setting<br>• Probe density doesn't have to be a problem (see Lind, G. et al., 2012 for example ), but needs to be addressed<br>• There may be harmful effects of CNT. Most nanotube solutions contain metal catalysts involved in their manufacture that are not removed by the purification process. Some of these, such as yttrium, are known to inhibit the function of ion channels in brain cells (Smith, K., 2008).<br>• We've seen nanorods being phagocytized and carried off by monocytes and suspect this is size-rather than material-dependent. Mention this, ?http://www.ncbi.nlm.nih.gov/pubmed/19845389<br>• It's possible that a lot of the benefit of CNT could be lost to tissue reactions within 50 μm from the implant. |
| Free-floating implant Advantages | Free-floating implant Disadvantages |
| • Reduced astroglial scarring and foreign body response.<br>• No transcranial or transdermal wiring prone to malfunctioning and infection. | • Power supply made more difficult.<br>• Explantation procedures in case of negative effects on patient possibly made more difficult. |

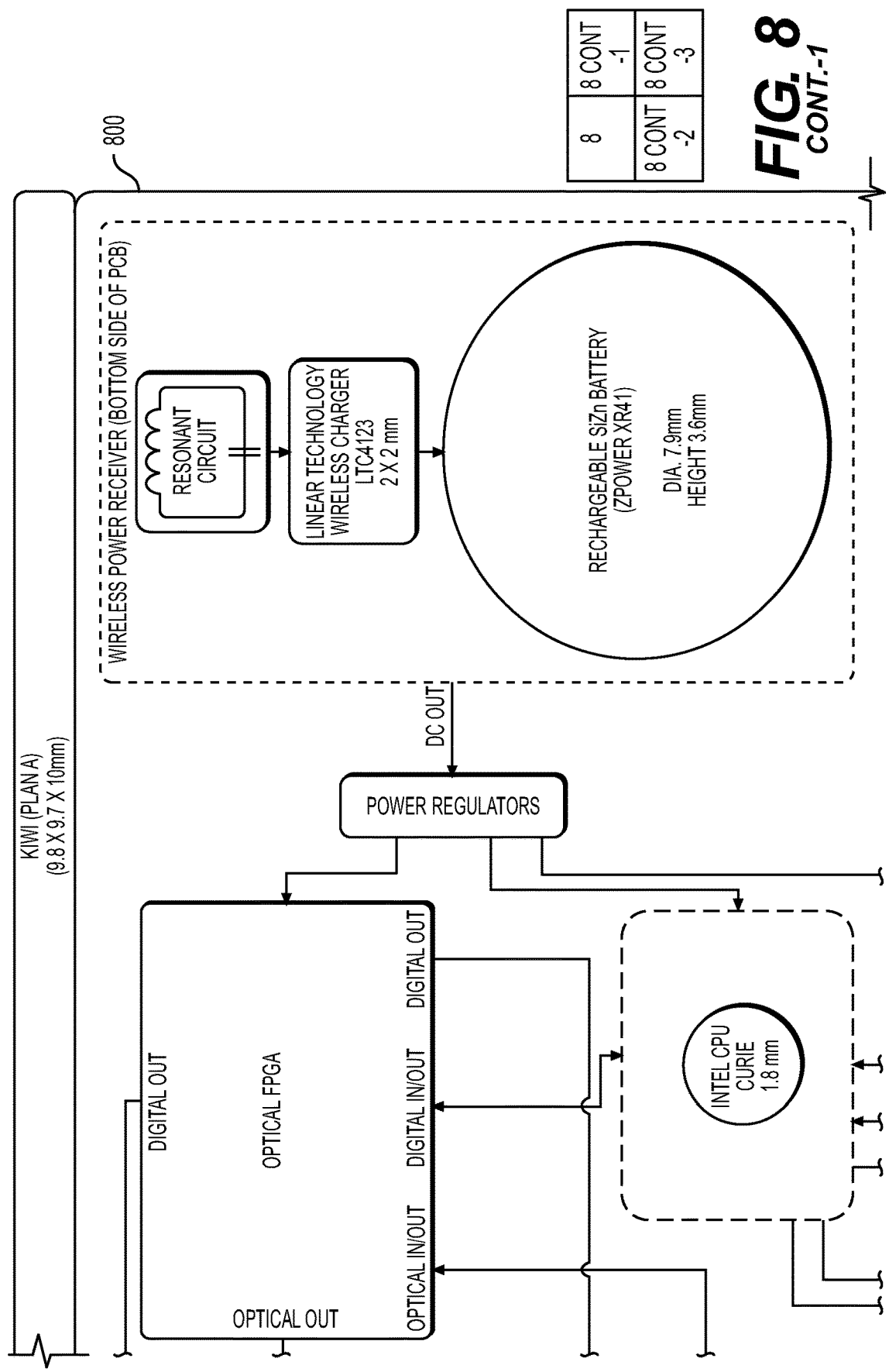

Problem Statement

- DBS is useful but imprecise, electrodes affect all neurons
- Read/write bandwidth of microelectrode arrays is limited
- Implants require wires for communications and power
- Implants are difficult or impossible to update, fail over time
- No implant with B2D-D2B deep ML and response exists
- No system synchronously captures multiple points (2+ KIWI)
- No closed-loop system of internal/external biofeedback exists
- No implant with cloud-scale processing capability exists
- No tool to quantifiably diagnose neurological disorder exists
- No tool to quantifiably track efficacy of treatment exists
- No means to merge data (fMRI, EEG, video, text, KIWI) exists
- No central DB exists of large volumes of raw scan/EEG data
- Implants only map locally – brain is a networked system

Vision

- Build a closed-loop optoelectric neuromodulative system
- NESD informed by internal and external conditions
- Realtime, full data capture and cloud-based analysis
- Map neuronal activity to behavior, context and vitals
- Map audial and prefrontal cortical activity to EEG, speech
- Lay groundwork for hearing augmentation, restoration
- Reach to D2B-B2D for thought to text, text to brain
- Develop highly accurate neurodiagnostic system
- Develop highly accurate neurotherapeutic system
- Develop wearable system for psychological screening
- Develop general-purpose implant for synchronous control of multiple implants to map and modulate entire brain circuits
- Decode the Language of the Brain

Program Objectives

- Develop high resolution bi-directional optrode, w/CNTs
- Build a (Kiwi-inspired) 3D radial probe with a million CNTs
- Read from 1M neurons, write to 100,000 neurons
- Read/write bi-directionally to over 1,000 neurons
- Build wireless comm and inductive recharge into implant
- Build earbuds with EEG and key vitals to comm with implant
- Build system wide apps and API/SDK for smartphone/tablet
- Build a secure cloud service to store and process all data
- Implant identical KIWI units in mPFC and audial regions
- B2D-D2B ML to mine for patterns and transduce Brain Codes
- Develop advanced database of Brain Codes/biomarkers
- Build a tool for diagnosing state of any neurological disorder
- Establish a therapeutic solution for treating PD, PTSD, others
- Map neural activity (3 points) to linguistic/cognitive structure
- Transcribe thought to text – with BCP, then from EEG alone

Impact

- Surgical intervention for PTSD, PD, ALS, many other disorders
- Will non-invasively diagnose state of many disorders, NDDs
- Unique radial design of implant
- CNTs increase points of neural connection
- CNTs improve bio acceptance
- Will improve quantity and quality of neural recording
- Provides realtime biofeedback for precise neuroprosthetics, enabling trained control of self and of remote devices (BMI)
- Collect vast quantities of neurobehavioral information to analyze in the cloud, enabling DML and Big Data neurology
- BCCS enable high-quality, low-cost home healthcare/monitor
- Closed-loop architecture will enable discovery of functional circuits, biomarkers and Brain Codes at unprecedented rate, enabling a range of new diagnostic and treatment modalities

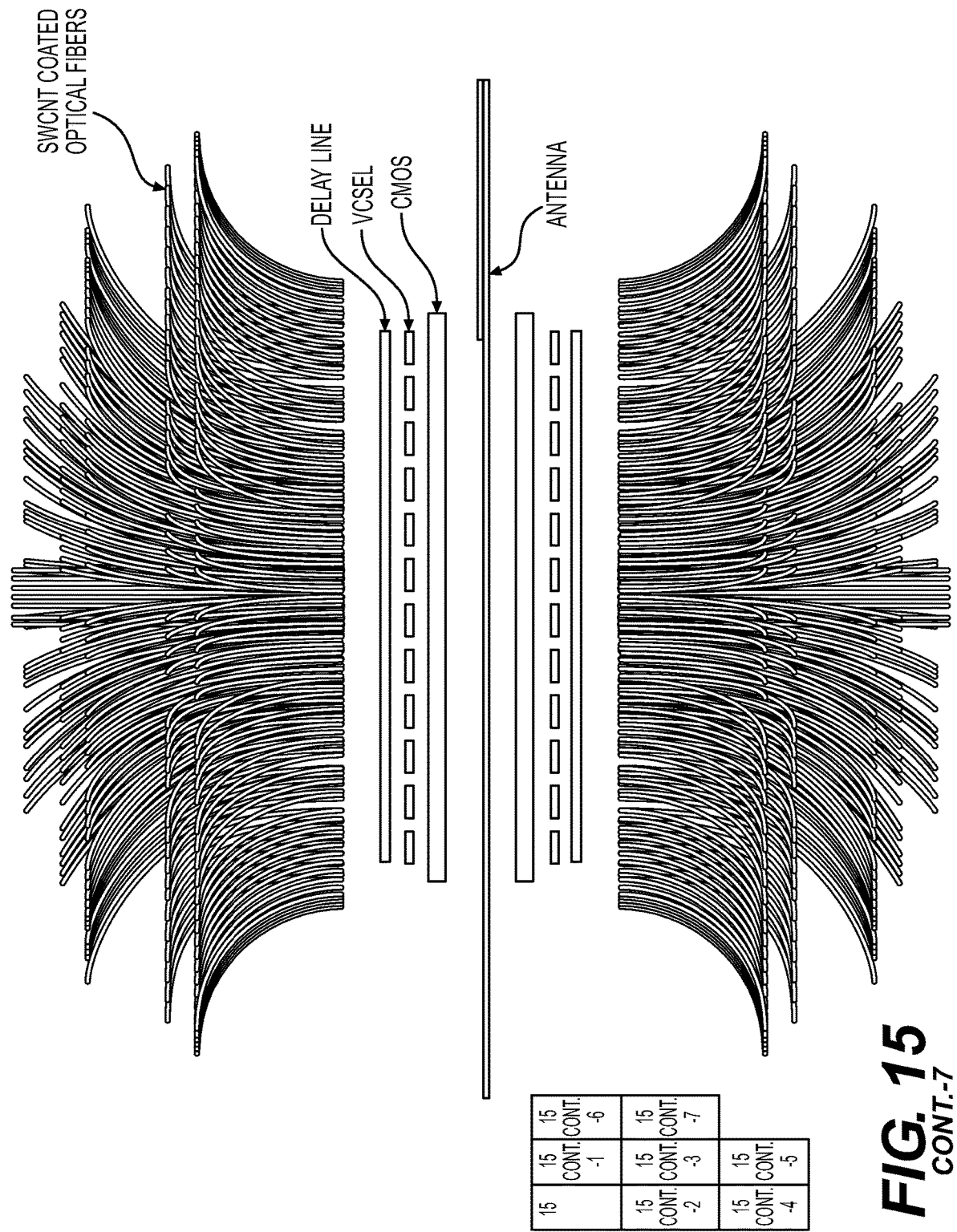

Personalized Fitness Example

Neural Oscillations Monitoring System Algorithm→Classification based on Borg Rating of Perceived Exertion→Scaling a Running-based Training Module Multi-level code translation to cognition

[S+,R-] + [+EPSP, -IPSP] + [3,5 ionization] + [3,5 primes oscillation] = [+/- speech]

MDP showing transitions between three mind states.

Fig. 25

| Symbol | Description | Properties |
|---|---|---|
| S | Brain regions | |
| A | Activation sets | $a \in A \Rightarrow a \subset S$ |
| $\mathscr{A}$ | Concept activation sets | $A \subset \mathscr{A}$ |
| W | Concepts | |
| p | Concept activation mapping | $P : a' \in \mathscr{A} \to w \in W$ |
| Ξ | Axiology | $\Xi : W \to \{+,-\}$ |
| F | Parity mapping | |
| μ | Weight mapping | |

Fig. 31

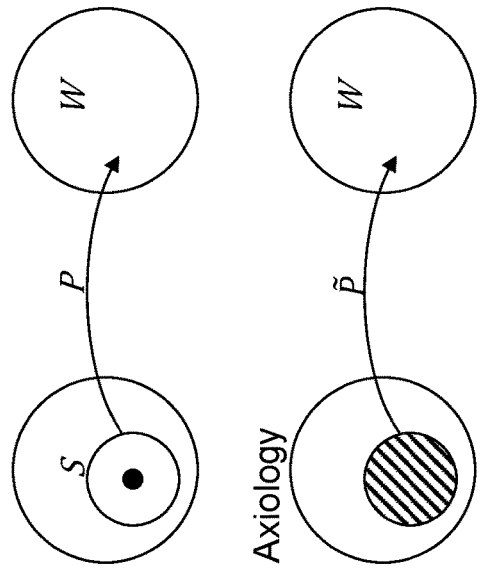

Set S and algebra A

Axiology

Weight Integral: $\int_a F(s)\,du(s)$ 2.3 Elements of Time
2.3.1 Effect based on duration
The weight mapping and the parity mapping may depend on a duration parameter
2.3.2 Time Evolution
Both the concept activation mapping and the brain activation mapping are presumed to change over time, either (i) in response to external stimulus or (ii) in response to "instantiating" the mapping.

$$d\mathcal{F}(a, t+\delta t, \Delta t) = f(a, t, \delta t, \Delta t, \mathcal{F}(a, \delta t, \Delta t))$$

Describing this properly will require a wave-function-like representation in which $\Xi(w) - \Xi(P(\tilde{P}(w)))$ is not necessarily 0.

Fig. 34

Photoelectric experiment

* Modeling an exchange of photons for electrons in a specific ratio (e.g., 5 photons for 3 electrons), based on the chemical element
* For example, if each photon has 1,759.2KJ/mol of energy, then those 5 photons (hitting simultaneously) would ionize iron into the +3 state.
* We theorize that each actionable photon should hold the quantum of energy required for 1 electron. Thus, using the above example, rather than having 5 photons at 1,759.2KJ/mol, we would ideally want 3 photons with different energies:
  * 762 KJ/mol to exactly match the first ionization energy of iron
  * 1,561 KJ/mol to exactly match the second ionization energy of iron
  * 2,957 KJ/mol exactly matches iron third ionization energy of iron
* The atmosphere is being ionized each night by high energy photons. If 5 photons hit a nitrogen you could get 3 electrons off, other combinations possible.

Fig. 35

Ionization energies of chemical elements

| Element | Atomic # | 1st ion. energy, kJ/Mole | 2nd ion. energy, kJ/Mole | 3rd ion. energy, kJ/Mole |
|---|---|---|---|---|
| H | 1 | 1312 | Nil | Nil |
| C | 6 | 1086.4 | 2352.6 | 4620.4 |
| N | 7 | 1402.3 | 2856 | 4578 |
| O | 8 | 1313.9 | 3388.2 | 5300.3 |
| Na | 11 | 495.8 | 4562.4 | 6912.2 |
| Al | 13 | 577.6 | 1816.6 | 2744.7 |
| Si | 14 | 786.4 | 1577 | 3231.5 |
| P | 15 | 1011.7 | 1903 | 2911.9 |
| S | 16 | 999.6 | 2251 | 3360.6 |
| K | 19 | 418.8 | 3051.3 | 4411.3 |
| Cr | 24 | 652.8 | 1592 | 2987.2 |
| Fe | 26 | 759.3 | 1561 | 2957 |
| Ni | 28 | 736.7 | 1752.9 | 3393.4 |
| Cu | 29 | 745.4 | 1957.9 | 3553.3 |
| Zn | 30 | 906.4 | 1733.2 | 3832.6 |
| As | 33 | 946.5 | 1797.8 | 2797.4 |
| Se | 34 | 940.9 | 2044.5 | 2973.7 |
| Cd | 48 | 867.7 | 1631.4 | 3616.2 |
| I | 53 | 1008.4 | 1845.8 | 3184 |
| Pb | 82 | 715.6 | 1450 | 3082 |

BIOLOGICAL CO-PROCESSOR (BCP)

CROSS-REFERENCE TO RELATED APPLICATIONS

This application claims the benefit of U.S. Provisional App. No. 62/326,007, filed Apr. 22, 2016, U.S. Provisional App. No. 62/353,343, filed Jun. 22, 2016, U.S. Provisional App. No. 62/397,474, filed Sep. 21, 2016, the contents of which are incorporated herein in their entirety.

BACKGROUND

The present invention relates to a device that may provide the capability to receive communication from neurons, cellular tissues, other physiological elements (all forms including but not limited to signal, frequency etc.), analyze that data, generate communication in a form readable by neurons or cells (for example, signals) and bi-directionally transmit communication to the same neurons or cells and or other neurons or cells, and through local and network-based processing.

One use case implementation is for brain and neurological disorders. Another use case is for any disease or dysfunction of any organ or body function. Another use case is for cognitive and or cellular enhancement for a living system healthy or unhealthy.

According to the United Nations, roughly one billion people, nearly ⅙th of the world's population, presently suffer from some form of neurological disorder, with some 6.8 million deaths each year. During the past decades, a large amount of work on several brain diseases was unsuccessful, because they take neither the initial state of the neuronal-brain region nor the initial neuronal interplay into consideration, greatly limiting the validity of conclusions made. Because the data recorded are only a snapshot of a precise situation, conclusions must be made based mainly on assumption about the properties of neurons and networks in prior states.

The UN estimates that one in every four people will suffer from a neurological or mental disorder in their lifetime and the vast majority of these cases will remain undiagnosed. Of those who are diagnosed, the World Health Organization claims two-thirds never seek treatment. Conventional systems cannot quantitatively detect and track the progression of a neurological disease (or the efficacy of a treatment).

Accordingly, a need arises for a system that can quantitatively detect and track the progression of a neurological disease (or the efficacy of a treatment), as well as to provide the capability to receive neuronal signals from brain tissue, transmit optical and electrical signals to brain tissue, as well as local and network-based processing to analyze and generate such signals.

The human body is an ocean of electricity and light activity that we can both listen to and influence. This relationship—of input and output—will impact the evolution of our species. KIWI offers open API to that electrical and optical network of the human body, it can be recorded, it can be modulated. We have designed intuitive, ergonomic, and socially responsible systems that improve the human experience as a whole. Our KIWI is among other features a low-cost bio sensing hardware/software platform, capable of measuring EEG, EMG, ECG, and more from brain and cellular activities.

We have coded a brain-computer interface (BCI) in a form close to the embodiment of a whole or partial artificial brain and or artificial cellular structure. This device is an embodiment of an open source, innovative, human-computer interface technology enabling brain computer interfacing, artificial intelligence, augmented reality, physical and cognitive computing, and brain to digital-digital to brain translation capable of implementing consciousness.

The Biological Co-Processor (BCP) device is capable of read and write, inter and extra cellular stimulation in any cellular system including but not limited to brain neuronal tissue. It's forms of embodiment include but are not limited to an implantable or wearable computer that can utilize our natural peripherals to process and input and return an output directly within a cellular system.

SUMMARY

Embodiments of the present invention may provide a general-purpose, relatively inexpensive, AI-driven device that is able to adapt to and modulate any given region in the brain or the body of a living system. Potential clinical applications may include cortical stimulation for treating psychiatric conditions, such as PTSD. For example, by recording and stimulating the auditory cortex and mPFC to identify and manipulate stimulus attention and oscillatory synchronization deficits in PTSD we may be able to establish an experimental treatment or cure for PTSD. This technology may also advance and expand fundamental, applied, theoretical, and clinical brain research, or be paired with other cellular technology such as transcriptomic, genomic, and proteomic. It may also be possible to apply a similar Biological Co-Processor (BCP) approach to the human nervous system.

Another research tool and use of the device may be brain and cellular recordings. Because a BCP can record 24/7 without interrupting physical or mental processes, during activities of daily living, data from a BCP can highlight the mechanism(s) by which several diseases occur, for example neurological disorders, mood disorders, cognitive decline, etc. Data collected from a healthy brain or cellular system during normal activity may enable us to better understand the neuronal or cellular properties and the function of a given brain region or living system. The device may be able to give us the dynamic continuum of the whole activity and the considered region and thus provide important insights into the fundamental mechanisms underlying both normal brain function and abnormal brain functions (for example, brain disease).

KIWI's ability to record a basic global neuronal state of a specific brain region and the dynamic neuronal interplay may allow for other uses of the device. The potential for these findings to be translated into therapies are endless because this device may be used in any region of the brain or cellular system and represents the first synthesis of a closed-loop modulator informed by internal and external conditions. The BCP provides a large amount of information and could be used to explore any brain or cellular disease (such as neurodegenerative or movement disorders) within a real dynamic, in vivo condition. The potential of this device for diagnosis and detection of cellular or neuronal diseases is enormous. The BCP device could also be used to reverse brain or cellular disease using light or electric modulation, for example therapeutic use cases may include chronic pain, tinnitus, and epilepsy. The device may also be able to complement existing techniques such as MRI for diagnosis, treatment and or research purposes. The device could be used in focal epileptic zone owing to its optogenetic capacity to control excitability of a specific populations of neurons.

Even if the device does not cure epilepsy, it may help to control otherwise refractory seizures and help to avoid surgery.

In embodiments, this cellular or neural interface system with the capabilities described herein would open a new frontier for research and medicine. That the BCP device may allow clinicians to better understand the mechanisms of brain function (and dysfunction), which would have countless applications and would deeply impact how neurological disorders are researched, managed and treated. The BCP would be of particular interest to the military, as the U.S. Department of Veterans Affairs, which is responsible for millions of veterans with some form of a neurological disorder. The VA estimates that 31% of all Vietnam veterans, 10% of all Gulf War veterans and 11% of those returning from Afghanistan suffer from Post-Traumatic Stress Disorder (PTSD). Traumatic Brain Injury (TBI) has been referred to as the "signature wound" of OEF/OIF service members, with over 200,000 cases diagnosed. Over 80,000 veterans have Parkinson's disease (PD) and even more are suffering from Alzheimer's disease (AD), dementia and depression. The BCP could treat or reverse many of these problems. The BCCS earbuds alone could be used to provide a high level of healthcare and disease management from home, saving the VA many millions of dollars in visitation and extended care costs Therapeutic aims may include use of the device as a brain stimulator, cellular stimulator drug delivery, disease management, disease detection, etc.

In an embodiment, a system for interacting with living tissue may comprise a device adapted to be attached to a body of a person or animal, adapted to transcribe signals from the living tissue, and adapted to transmit the transcribed signals, a processing device adapted to receive the transcribed signals, process the transcribed signals, and transmit the processed transcribed signals; and a computer system adapted to receive the processed transcribed signals, store and further process the processed transcribed signals, and store other data related to the person or animal.

In embodiments, the device may comprise a plurality of carbon fibers adapted to receive electrical signals from the living tissue, a processor adapted to receive the electrical signals and to process the electrical signals to form digital data representing the signals, and a transmitter adapted to transmit the digital data representing the signals. The carbon fibers may comprise single walled carbon nanotubes. The device may further comprise a receiver adapted to receive digital data representing signals to be applied to the living tissue and output control signals representing the signals to be applied to the living tissue, a plurality of light sources adapted to receive the control signals and output optical signals representing the control signals, and a plurality of optical fibers adapted to apply the optical signals to the living tissue. The optical fibers may be coated with single walled carbon nanotube which adapt the optical fibers to receive electrical signals from the living tissue. The device further may comprise delay lines between the carbon fibers and the coated optical fibers and the processing device, wherein the delay lines are adapted to compare time between pulses of the electrical signals. The light sources may comprise vertical-cavity surface-emitting laser devices. The transmitter may comprise a wireless transmitter. The device further may comprise an inductively-recharged power source. The device is further may be adapted to be implanted within the body of the person or animal and the transcribed signals may comprise neural signals from living brain or other neural tissue.

In an embodiment, a method for interacting with living tissue may comprise attaching a device to a body of a person or animal, the device comprising plurality of carbon fibers in contact with the living tissue, receiving by the carbon fibers signals from the living tissue, processing the received signals by the device, and transmitting the processed signals.

In an embodiment, a computer program product for controlling interaction with living tissue may comprise a non-transitory computer readable storage having program instructions embodied therewith, the program instructions executable by a processor, to cause the processor to perform a method comprising receiving neural signals at a device attached to a body of a person or animal, the signals received from the living tissue using a plurality of carbon fibers coupled to the device attached to the body of the person, the plurality of carbon fibers in contact with the living tissue, processing the received signals by the device, and transmitting the processed signals.

In an embodiment, the device may be implanted within the body, for example, in contact with the brain or attached to the Vagus nerve on the neck.

BRIEF DESCRIPTION OF THE DRAWINGS

The details of the present invention, both as to its structure and operation, can best be understood by referring to the accompanying drawings, in which like reference numbers and designations refer to like elements.

FIG. 6 illustrates exemplary advantages of aspects of technologies that may be utilized by embodiments.

FIG. 7 illustrates exemplary advantages of aspects of technologies that may be utilized by embodiments.

FIGS. 8, 8CONT1, 8CONT2, and 8CONT3 illustrate an exemplary embodiment of a KIWI device.

FIGS. 10 and 10CONT1 illustrate an example of factors linking behavior with neural, muscular, glandular, and genetic activities.

FIG. 12 illustrates examples of objectives and advantages of embodiments of the present invention.

FIGS. 15, 15CONT1, 15CONT2, 15CONT3, 15CONT4, 15CONT5, 15CONT6, and 15CONT7 illustrate an exemplary embodiment of a Biological Co-processor System.

FIG. 25 illustrates examples of definitions of symbols for axiology mappings.

FIG. 31 illustrates an example of elements of time including effect based on duration and time evolution.

FIG. 34 illustrates and exemplary photo electric experiment.

FIG. 35 illustrates examples of ionization energies of chemical elements.

DETAILED DESCRIPTION

The following patent applications are incorporated herein in their entirety: U.S. Provisional App. No. 62/214,443, filed Sep. 4, 2015, U.S. patent application Ser. No. 15/257,019, filed Sep. 6, 2016, U.S. Provisional App. No. 62/294,435, filed Feb. 12, 2016, U.S. patent application Ser. No. 15/431, 283, filed Feb. 13, 2017, U.S. Provisional App. No. 62/294, 485, filed Feb. 12, 2016, U.S. patent application Ser. No. 15/431,550, filed Feb. 13, 2017, U.S. Provisional App. No. 62/308,212, filed Mar. 14, 2016, U.S. patent application Ser. No. 15/458,179, filed Mar. 14, 2017, U.S. Provisional App. No. 62/308,212, filed Mar. 14, 2016, and U.S. patent application Ser. No. 15/458,179, filed Mar. 14, 2017.

The Biological Co-Processor is unique in that is uses advanced nanotechnology, optogenetics and deep machine learning to intelligently map internal events, such as neural spiking activity, to external physiological, linguistic and behavioral expression. The initial device contains over a million carbon nanotubes, each of which is 10,000 times smaller than the width of a human hair. Carbon nanotubes provide a natural, high-bandwidth interface as they conduct heat, light and electricity. They adhere to neuronal constructs and even promote neural growth.

The device uses a combination of methods to write to the brain, including pulsed electricity, light and various molecules that simulate or inhibit the activation of specific neuronal groups. These can be targeted to stimulate a desired response, such as releasing chemicals in patients suffering from a neurological disorder or imbalance. The BCP is designed to use the brain's own internal systems and chemistries to pattern and mimic healthy brain behavior, an approach that stands in stark contrast to the current state of the art, which is to simply apply mild electrocution to problematic regions of the brain.

Rather than simply disrupting neural circuits, the machine learning systems within the BCP are designed to interpret these signals and intelligently read and write to the surrounding neurons. These capabilities could be used to reestablish any degenerative or trauma-induced damage and perhaps write these memories and skills to other, healthier areas of the brain. Because the brain controls all systems in the body the BCP may be used to interface and modulate organs and functions outside of the brain The BCP device could also be used in healthy patients to radically augment human ability and proactively improve health and cognitive capacity.

Figure 1:
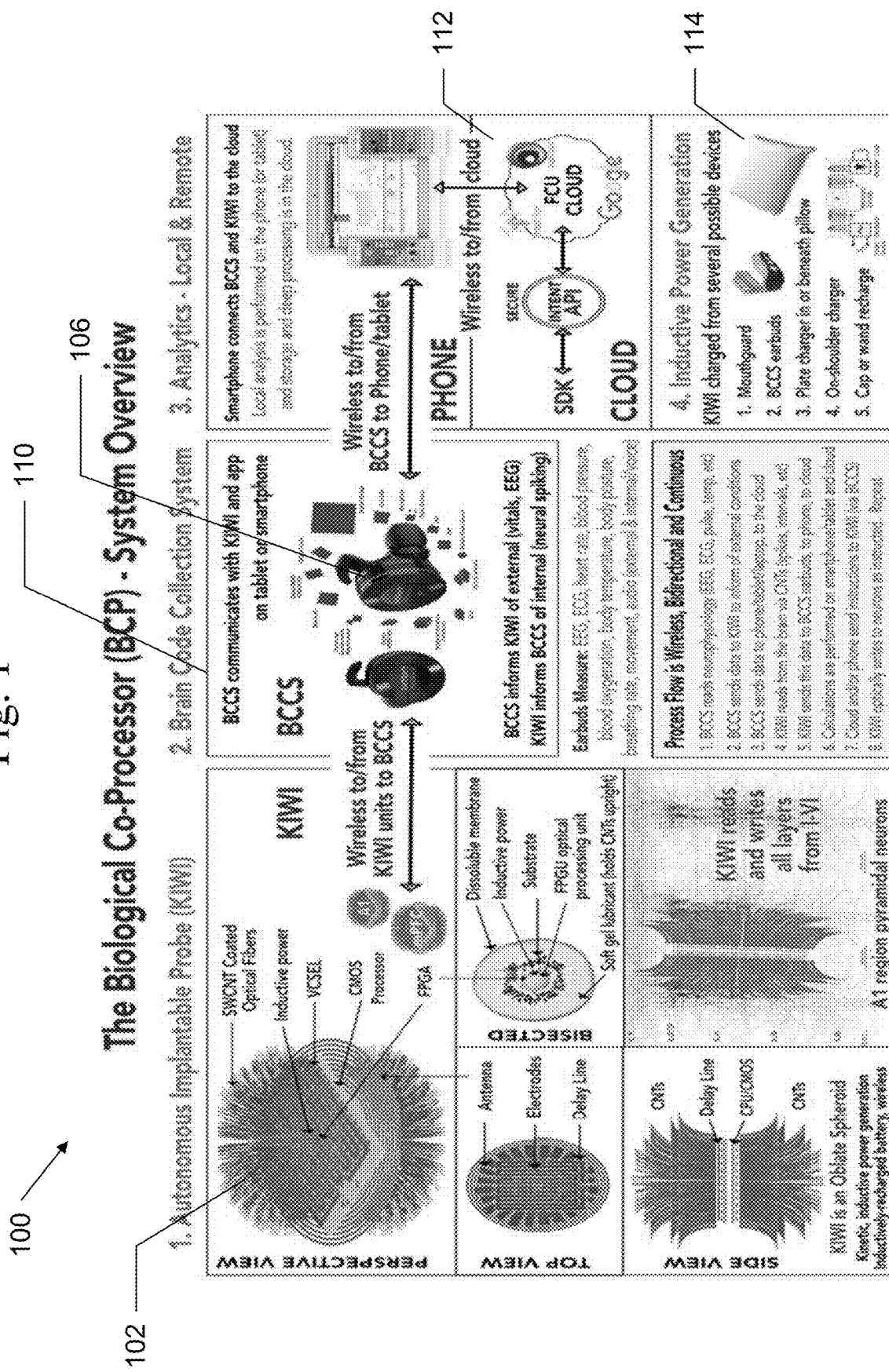
FIG. 1 illustrates an exemplary embodiment of a Biological Co-Processor System (BCP).

An exemplary embodiment of a Biological Co-Processor System (BCP) 100 is shown in FIG. 1. In embodiments, BCP 100 may include a neuromodulatory system comprising one, two, or more inductively-recharged neural implants 102 (the KIWI), two earbuds 106, which may include wireless and various sensors, together known as the Brain Code Collection System (BCCS) 110. These devices may work independently, but together may form a closed-loop system that provides the BCP 100 with bidirectional guidance of both internal (neural) and external (behavioral and physiological) conditions. The BCCS earbuds 106 may read the brain for oscillatory rhythms from internal onboard EEG and analyze their co-modulation across frequency bands, spike-phase correlations, spike population dynamics, and other patterns derived from data received from the KIWI implants 102, correlating internal and external behaviors. The Fundamental Code Unit (FCU) 112 is a mathematical framework that enables the various BCCS 110 sensor feeds and KIWI 102 neural impulses to be rapidly and meaningfully combined.

The FCU 112 may provide common temporal and spatial coordinates for the BCP 100 and resides in all components of the system (implants, earbuds, app, cloud) ensuring consistent mapping across different data types and devices. FCU 112 algorithms may provide extremely high rates of data compression, association and throughput, enabling the KIWI 102 to transcribe neural signals in high volume. Each KIWI 102 may have an embedded AI processor, optical neurostimulation capabilities and electrical recording capabilities. The KIWI 102 may consist of two types of microfabricated carbon nanotube (CNT) neural interfaces, a processor unit for radio transmission and I/O, a light modulation and detection silicon photonic chip, an inductive coil for remote power transfer and an independent receiver system, where the signal processing may reside. The BCP 100 system may include any or all of four main components: (1) the KIWI 102 implant(s), (2) the BCCS 110 and (3) the cloud services (with API and SDK) and (4) an inductive power supply.

Figure 2:
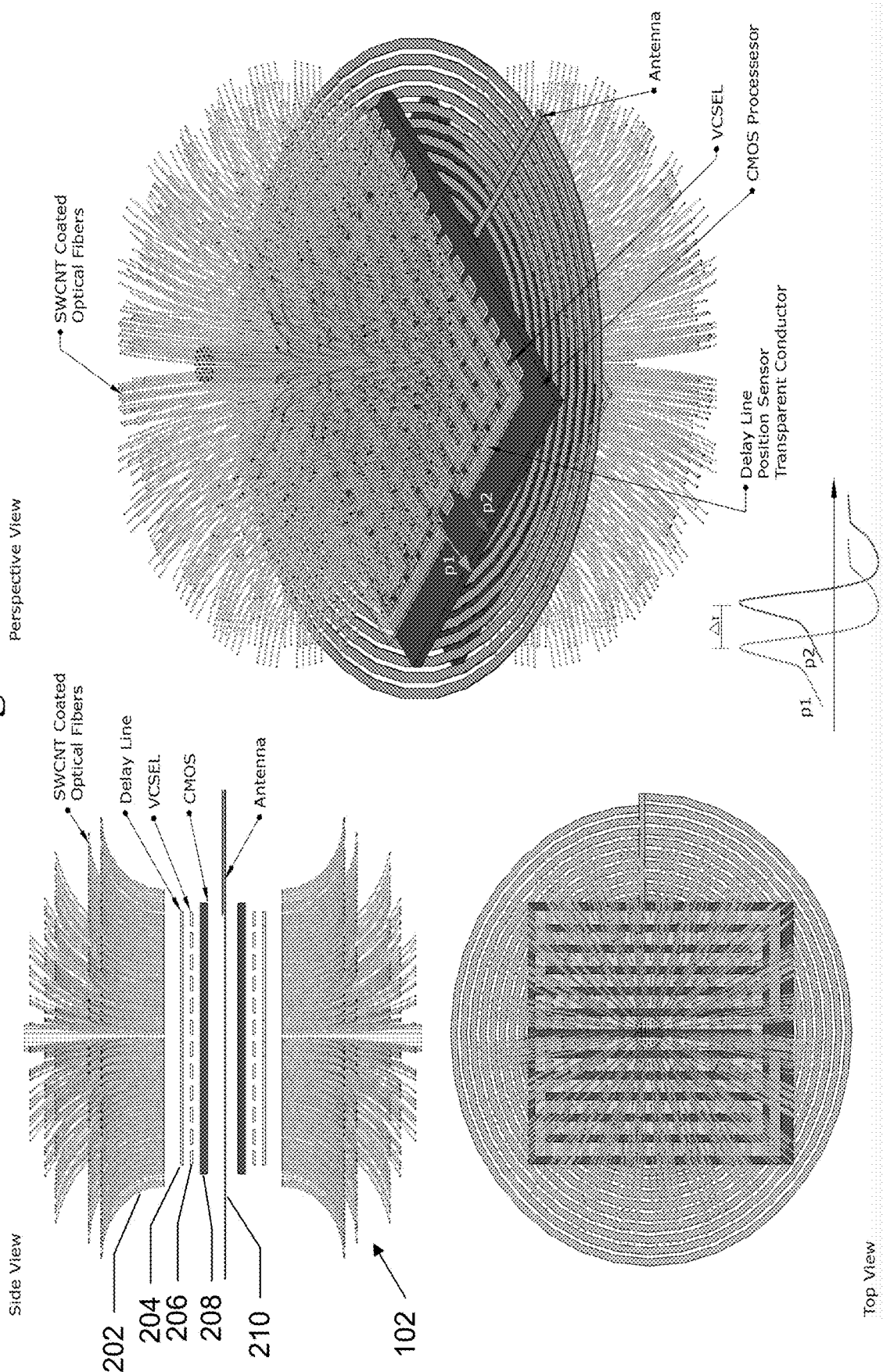
FIG. 2 illustrates an exemplary embodiment of an implantable signal receiving, processing, and transmitting device, shown in FIG. 1.

Turning briefly to FIG. 2, each KIWI 102 implant may be, for example, an oblate spheroid (for example, 0.98×0.97× 1.0 cm), a design inspired by the radial characteristics of a KIWI 102 fruit. In the center of the implant is a nucleus surrounded by a fleshy membrane. The nucleus may house the processing, transmitting, and receiving circuitry 208, including an embedded processor for local preprocessing, read and write instructions, the modulation scheme, and an optical or electronic FPGA dedicated for real time optical modulation. It may also contain a CMOS dedicated integrated front-end circuit developed for a pre-amplification and multiplexing of the neural signals recorded, 4G-MM for offline storage, wireless transceiver, inductive power receiver, and an optical modulation unit. Covering the nucleus are, for example, 1 million fibers 202 made of single walled carbon nanotubes (SWCNT) and, for example, 1100 geometrically distributed optical fibers coated with SWCNT, connected in the same manner as the SWCNT fibers, wrapping around a central primary processing nucleus. Fibers are built on a flexible interface substrate and surrounded by a gel/flesh membrane. When implanted, the membrane casing will slowly dissolve, naturally exposing the probes to a cellular environment with limited risk of rejection. The lubrication of the CNT probes will attract neurons to the implant. The KIWI 102 implant may, for example be able to record from pyramidal layers II-III down to layer VI of any brain cortex region, as well as other regions of brain tissue or other types of tissue. Also shown in FIG. 2 are delay line devices 204, light sources, such as vertical-cavity surface-emitting lasers 206 (VCSELs), and antenna 210.

Figure 3:
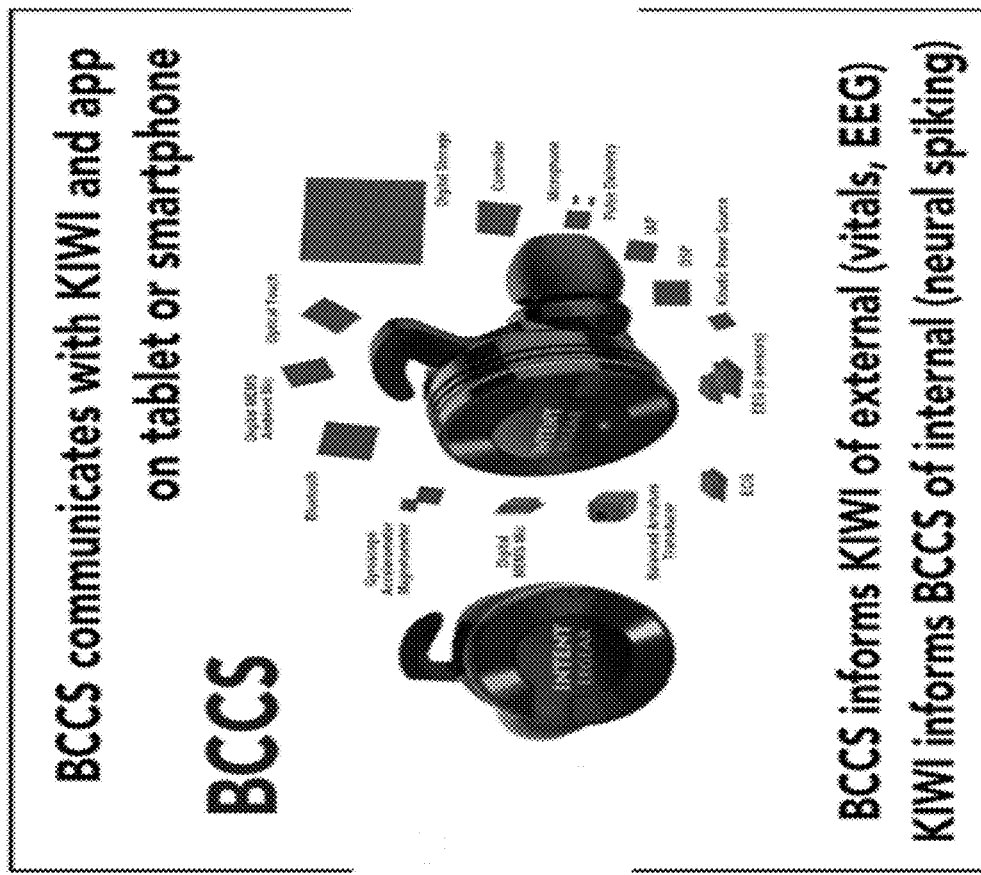
FIG. 3 illustrates an exemplary embodiment of Brain Code Collection System earbud, shown in FIG. 1.

Returning to FIG. 1, the BCCS earbud 106, also shown in FIG. 3, wirelessly communicates with the KIWI 102. The earbud contains a signal amplifier and a relay for modulation schemes, algorithms and instructions to and from the implant. The BCCS earbud 106 may also include additional functions. For example, such additional functions may include EEG and vestibular sensors, which will serve as crosscheck metrics to measure efficacy and provide global behavioral, physiological and cognitive data along with neural data on the same timescale, as well as many other types of additional functions and sensors.

Figure 4:
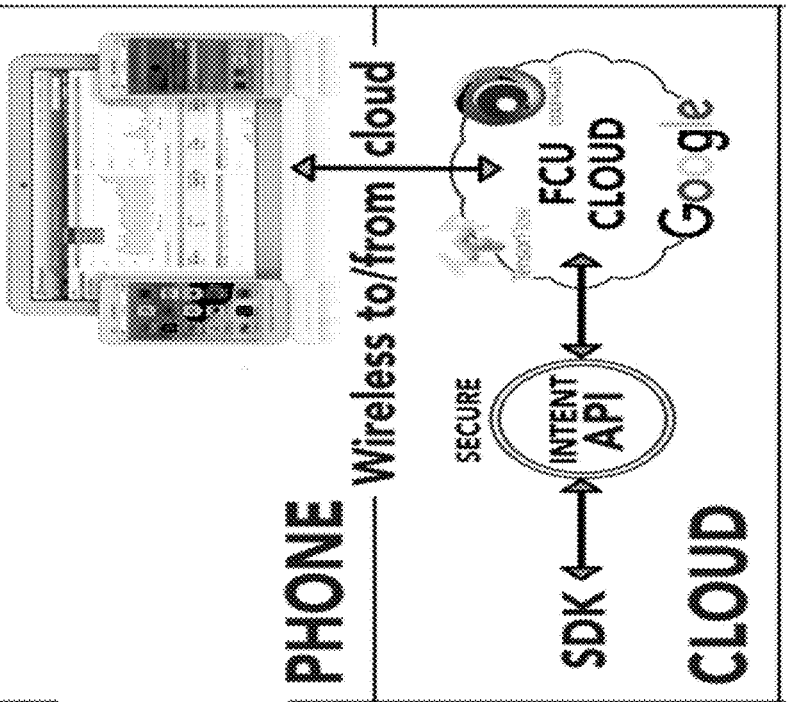
FIG. 4 illustrates an exemplary embodiment of a cloud platform, shown in FIG. 1.

A cloud platform 112, also shown in FIG. 4, may include the parallel data flow and FCU 112 analytic engine powered by neuro-computational algorithms and extreme machine learning. Physiological data, such as EEG, ECG, and other (external and internal) will be uploaded to the cloud wirelessly and automatically from the BCCS 110 and KIWI 102. A suite of algorithms will analyze the aggregate data streams and formulate instructions to the KIWI for optimal electrical and/or optical neuromodulations in a closed loop feedback system. Integrated stimulation/control, recording/readout and modulated stimulation parameters will allow simultaneous optical and/or electrical recording and stimulation.

Figure 5:
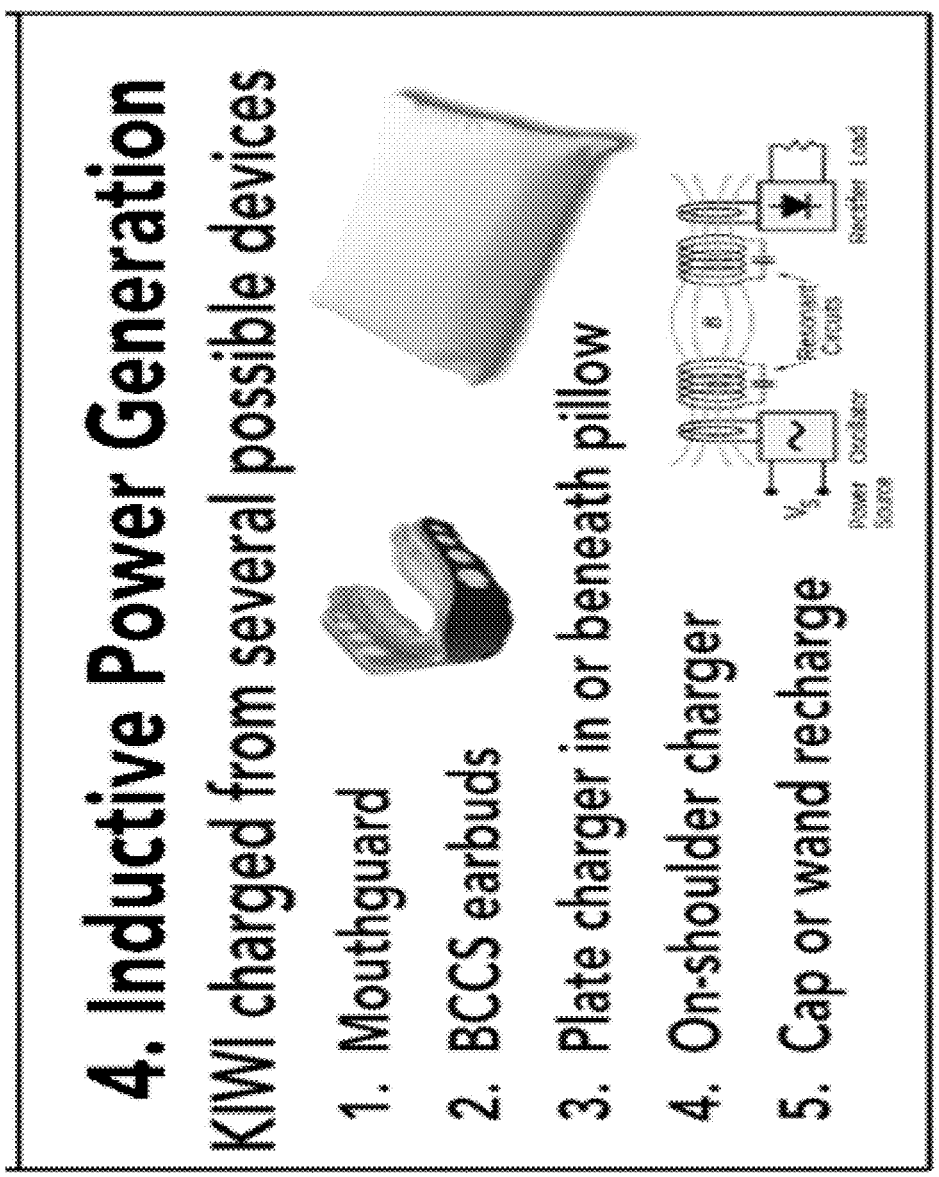
FIG. 5 illustrates an exemplary embodiment of an inductive powering system, shown in FIG. 1.

An inductive powering system 114, also shown in FIG. 5, may be used recharge the KIWI 102 implant (see FIG. 1) non-invasively. Various wearable and/or kinetic inductive power technologies may be utilized, including a retainer/mouthguard, a head-mounted cap, or an under the pillow charging mat.

Combined electro and optogenetic approach enables precise ON/OFF control of specific target neurons and circuits. Unary controls in combination with rapid closed loop controls in the KIWI's microchip will enable neural synapse firings with intensity, and frequency modulation.

Integrating SWCNT nanotechnology with optical fibers enables both optogenetic writing and electrical stimulation capabilities synchronously or independently.

CNTs are biologically compatible, enabling the KIWI to be stably implanted for long periods of time.

A dissolvable membrane, such as Dextrane, Gelatine, or Collicoat, will limit the risk of damaging sensitive surface tissue during surgery and minimize adverse tissue reactions following the implant insertion trauma. This will protect both the patient and the CNTs.

The KIWI implant will be in the brain parenchyma, rather than tethering the implant to the skull, which can be a major contributor to adverse tissue reactions.

The KIWI's open hardware architecture can record data from all pyramidal layers II-III down to layer VI (as well as other types of brain and neural tissue, and other types of tissue) offering several advantages in terms of data quality.

Closed loop architecture enables dynamic, informed response based on real-time internal and external conditions.

Big data approach utilizing smartphone apps, SDKs, and websites/APIs will provide visual, aggregate and actionable real-time biofeedback and software modification capabilities.

Big data approach utilizing cloud API will provide storage to capture extremely large volumes of data. The cloud platform also provides the massive processing power required to analyze these huge data sets across subject profiles and a plurality of research databases (PPMI, PDRS, etc.).

Open software architecture SDK will allow the creation of new applications and different protocols for clinical and research use, by partners, researchers and third parties.

The BCCS will be able to synchronously capture EEG, ECG, PulseOx, QT intervals, BP, HR, RR, true body temperature, body posture, movement, skin conductance, vestibular data, and audio data to provide a rich set of multi-modal data streams to dynamically correlate internal states read by the KIWI and external states observed by the BCCS, a process which will help to effectively map neural pathways and function.

The KIWI implant can be small, low power and of low energy consumption.

The BCP data flow (internal and external) allows machine learning, prior experience and real time biofeedback to autonomously guide KIWI neuromodulation. Eventually the BCP will achieve an advanced level of sensitivity and will be able to autonomously sense neuron activity and guide light and/or electrical stimulation as needed.

Autonomous stimulation will be guided by intuitive algorithms and operational self-monitoring during awake state and sleep. Personal profiles and personalized signatures of neural activity will be learned and coded over time.

The BCP system takes two distinct but complementary approaches: a direct approach by means of recording brain activity and an indirect approach deduced from the multimodal aggregate analysis of peripheral effectors such as temperature, cardiac activity, body posture and motion, sensory testing etc. This simultaneous and coupled analysis of the interplay between the brain "activities and functions" (including physiological, chemical and behavioral activities) and its peripheral effectors and the influence of the effectors on the brain "activities and functions" has never been done before.

Simultaneous brain recording and stimulation of the same region allows us to take account of the initial state of the neurons and their environment, enabling comprehension of the neurons properties and network as well as brain functions (as the data are only valid for the specific conditions in which they were obtained). Methods which are forced to ignore this initial state have limited potential for understanding the full system.

KIWI Development—in an embodiment, an approach to solving density challenges combines traditional photolithographic thin-film techniques with origami design elements to increase density and adaptability of neuronal interfaces (Niiyama, R. et al., 2015). Compared to traditional metal or glass electrodes, polymers such as CNT are flexible, strong, extremely thin, highly biocompatible, highly conductive, and have low contact impedance, which permits bidirectional interfacing with the brain (Vitale et al., 2015). These properties are especially valuable for the construction of high-density electrode arrays designed for chronic and/or long-term use in the brain. Our approach to precision and accuracy supersedes the current state of the art (SOA), which is limited to only being able to fit certain regions of the brain. These limits are due both to the physical design of the interface inserted and also to the limits of tethered communication within deeper cortical areas. The KIWI, on the other hand, is a fully computational I/O device, wireless and inductively chargeable or self-powered, and so it is implantable anywhere in the brain or other extra-cellular areas of the body, to include but not limited to the nervous system. The device can wirelessly communicate with a transceiver, which may be embodied as a patch, subdural or fully implanted, to allow reading of the cell or the neurons both at the surface and in 3D. The KIWI device can be embodied with a separate transceiver as described above or the transceiver can be built into the device itself. Other embodiments of the KIWI could be less invasive, or completely non-invasive such as a patch worn externally without any implantation or surgery. CNT fibers will allow for bidirectional input and output. CNTs will also enable more biocompatible, longer-lasting designs—current neural implants can work for short periods of time, but chronic or long-term use of neural electrodes has been difficult to achieve. The main reasons for this are: 1) degradation of the electrode, 2) using oversized electrodes to attain sufficient signal-to-noise ratio during recording, and 3) the body's natural immune response to implantation. Although there is a strong desire among neurologists to record chronic neural activity, electrodes used today can damage brain tissue and lose their electrical contacts over time (McConnell et al., 2009, Prasad et al., 2012). This is of particular concern in the case of deep cortical implants, therefore alternative materials, design principles, and insertion techniques are needed. CNT is a biocompatible material that has been proven safe for long-term use in the brain (Kashiwagi, K. & Yamashita, S., 2009; Ahn et al., 2015, Vitale et al., 2015).

Optogenetics, a technology in which light-sensitive ion channels are expressed in target neurons allowing their activity to be controlled by light, as well as other techniques may be used to facilitate selective, high-speed neuronal and cellular activation. A. By coating optical fibers (~8 µm) with dense, thin (~1 µm) CNT conformal coatings, optical modulation units may be built within the nucleus of the KIWI device that can deliver light or electric stimulation to precise locations deep within the brain, or nervous system or extra cellular organ, while recording activity at the same target locations. The light-activated proteins channelrhodopsin-2 and halorhodopsin may be used to activate and inhibit neurons in response to light of different wavelengths. Precisely-targetable fiber arrays and in vivo-optimized expression systems may enable the use of this tool in awake, behaving primates.

A suite of brain to digital and digital to brain (B2D:D2B) algorithms may be used for transducing neuron output into digital information. These algorithms may be theoretically-grounded computational models corresponding to the theory of similarity computation in Bottom-Up and Top-Down signal interaction. These neurally-derived algorithms use mathematical abstractions of the representations, transformations, and learning rules employed by the brain, which will correspond to the models derived from the data and correspond to the general dynamic logic and mathematical framework, account for uncertainty in the data, as well as provide predictive analytical capabilities for events yet to take place. BCP analytics may provide advantages over conventional systems in similarity estimation, generalization from a single exemplar, and recognition of more than one class of stimuli within a complex composition ("scene") given single exemplars from each class. This enables the system to generalize and abstract non-sensory data (EEG, speech, movement). Combined, these provide both global (brain-wide) and fine detail (for example, communication between and within cytoarchitectonic areas) modalities for reading and writing across different timescales.

The KIWI may be a microfabricated carbon nanotube neural or cellular implant that may provide, reading from $\geq 1$ neurons or cells (for example, up to one million or more), writing to $\geq 1$ neurons or cells (for example, up to one hundred thousand or more), and reading and writing simultaneously to $\geq 1$ neurons or cells (for example, up to one thousand or more) The BCCS may include multisensory wireless inductive earbuds and behavioral sensors and provide wireless communication with KIWI, inductively recharge KIWI, provide Bluetooth communication with a secure app on smartphones, tablets, etc., and may provide interfacing with cloud—API, SDK and secure website for clinicians, patients (users).

The KIWI and BCCS devices may be used in combination with FCU, BC and IA algorithms to translate audial cortex output, matching internal and external stimulus (for example, output) to transcribe thought into human readable text.

The BCP may provide advantages over conventional systems by providing a closed loop neural interface system that uses big data analytics and extreme machine learning on a secure cloud platform, to read from and intelligently respond to the brain using both electrical and optical modulation. The FCU unary framework enables extremely high speed compression, encryption and abstract data representation, allowing the system to process multimodal and multi-device data in real-time. This capability is of great interest and benefit to both cognitive neurosciences and basic comprehension of brain function and dysfunction because: (1) it combines high dynamic spatiotemporal and functional resolution with the ability to show how the brain responds to demands made by change in the environment and adapts over time through its multiple relationships of brain-behavior and brain-effectors; (2) it assesses causality because the data streams are exhibited temporally relative to the initial state and each state thereafter by integrating physiological and behavioral factors such as global synchrony, attention level, fatigues etc., and (3) data collection does not affect, interfere or disrupt any function during the process.

The BCP may provide advantages over conventional systems by recording from all six layers of the primary A1 cortex and simultaneously from the mPFC, with very high spatial resolution along the axis of the penetrating probe by combining CNT with fiber optic probes that wrap around a central nucleus. By including the principal input layer IV and the intra columnar projection layers, as well as the major output layers V and VI, brain activity can be monitored with unprecedented resolution. The recording array can be combined with optogenetic stimulation fibers, which are considerably larger and stiffer than electrode arrays. CNT fibers can be used as recording electrodes at an unprecedented scale and within a highly dense geometry.

Carbon nanotubes address the most important challenges that currently limit the long term use of neural electrodes and their unique combination of electrical, mechanical and nanoscale properties make them particularly attractive for use in neural implants. CNTs allow for the use of smaller electrodes by reducing impedance, improving signal-to-noise ratios while improving the biological response to neural electrodes. Measurements show that the output photocurrent varies linearly with the input light intensity and can be modulated by bias-voltage. The quantum efficiency of CNTs are about 0.063% in 760 Torr ambient, and becomes 1.93% in 3 mTorr ambient. A SWCNT fiber bundle can be stably implanted in the brain for long periods of time (Vitale F. et al, 2015) and attract neurons to grow or self attach to the probes as observed in several studies (Bareket-Keren, L. & Hanein, Y., 2014a; Sucapane, A. et al., 2009). CNT and optical fibers will be an excellent shank to wrap a polymer array around.

Returning to FIG. 2, the optical fibers 202 will be coated with SWCNTs and make electrical connections with the underlying delay line. The delay line 204 will be transparent to allow light from the vertical-cavity surface-emitting lasers 206 (VCSELs) to reach the optical fibers. The delay lines 204 potentially make the electrical signal position-dependent by comparing the time between pulses measured at the outputs. Provided the pulses are of sufficient intensity and individual pulses are sufficiently separated in time (>1 μs or so), the difference between pulse arrival times could be related to the position on the array. Combining this with spatially controlled optical excitation (i.e., by turning on specific VCSELs 206) would further help to quantify position, as VCSEL pulses excite a small region at the end of the adjacent fiber. These pulses are measured at a position on the delay line close to this fiber, so if neighboring neurons fire, they are sensed by nearby fibers (i.e., the SWCNTs on the fibers) and would generate additional pulses that could then be tracked over time with the delay line, mapping out the path. The SWCNT coated fiber array 202 would be randomly connected to the underlying VCSEL array as we will not have control over the fiber locations in the bundle. The substrate connectors will be graphitic nano-joints to a single-walled carbon nanotubes, we will also utilize the IBM CNT connect technique for other connectors.

Carbon nanotubes are ideal for integration into neural interfaces and the technical feasibility of doing so is well documented (Kashiwagi, K. & Yamashita, S., 2009). The use of CNT allows for one unit to function as recording electrodes and stimulating optical fibers. The optical transceivers will be integrated as a separate die on a silicon substrate, tightly-coupled to logic dice (a.k.a. "2.5D integration"). The choice of materials reflects the positive results of recent studies demonstrating the impact of flexibility and density of implanted probes on CNNI tissue responses (Köhler, P. et al., 2015; Lind, G., Linsmeier, C. E., & Schouenborg, J., 2013). CNTs are not only biocompatible in robust coatings, but they are supportive to neuron growth and adhesion. It has been found that CNTs actually promote neurite growth, neuronal adhesion, and viability of cultured neurons under traditional conditions (Lovat, V. et al., 2005; Nunes, A. et al., 2012; Silva, G. A., 2006). The nanoscale dimensions of the CNT allow for molecular interactions with neurons and the nanoscale surface topography is ideal for attracting neurons (Minnikanti, S. & Peixoto, N., 2011; Sorkin, R. et al., 2008). In fact, they have been shown to improve network formation between neighboring neurons by the presence of increased spontaneous postsynaptic currents, which is a widely-accepted way to judge health of network structure (Lovat, V. et al., 2005). Additionally, functionalization of CNT can be used to alter neuron behavior significantly (Harrison, B. S. & Atala, A., 2007). In terms of the brain's immune response, CNT have been shown to decrease the negative impact of the implanted electrodes. Upon injury to neuronal tissue, microglia (the macrophage-like cells of the nervous system) respond to protect the neurons from the foreign body and heal the injury, and astrocytes change morphology and begin to secrete glial fibrillary acidic protein to form the glial scar (Bellamkonda, R. V., Pai, S. B., & Renaud, P., 2012; Fitch, M. T. & Silver, J., 2008). This scar encapsulates the electrode and separates it from the neurons. However, carbon nanomaterials have been shown to decrease the number and function of astrocytes in the brain, which in turn decreases the glial scar formation (Mckenzie, J. L. et al., 2004; Zhou, H. et al., 2013).

Optogenetic tools may be used to enable precise silencing of specific target neurons. Using unary controls in combinations and in rapid closed loop controls within the KIWI will enable neural synapse firings with highly precise timing, intensity, and frequency modulation. Optical neuromodulation has many benefits over traditional electrode-based neurostimulation (Bareket-Keren, L. & Hanein, Y., 2014b; Boyden, E., 2011; Boyden, E. S. et al., 2005; Boyle, P. M., Entcheva, E., & Trayanova, N. A., 2014; Deisseroth, K., 2011; Fenno, L., Yizhar, O., & Deisseroth, K., 2011; Gerits, A. et al., 2012; Kringelbach, M. L. et al., 2007; Lalumiere, R. T., 2011; Liewald, J. F. et al., 2008; Owen, S. et al., 2007; Zhang, F. et al., 2007). This strategy will allow precision stimulation in near real time.

The KIWI uses a 3D design (and dissoluble membrane), both of which may provide advantages over conventional systems. The dissoluble membrane protects both the patient and the implant during surgery and the lubricant and contraction encourages neural encroachment and adherence to CNTs upon dissolution. This design maximizes neural connectivity and adhesion, while minimizing implant size. KIWI size is further reduced through inductive charging.

The BCP system aims at producing a significant leap in neuroscience research not only in scale but also in precision. The method of optical reading and writing at the same time, using SWCNT optrodes, can be combined with current cell marking techniques to guide electrodes and optic fibers to specific regions of the brain. One of the biggest challenges facing neuroscientists is to know for certain if they are hitting the right spot when performing in vivo experiments, whether it is an electrophysiological recording or an optogenetic stimulation. Cell marking techniques, on the other hand, have made a lot of progress during the past 20 years with the use of new viral approaches as well as Cre-Lox recombination techniques to express cell markers in specific sites of the brain (Ahmed et al., 2004). This has allowed, for example, the expression of fluorescent Calcium indicators in target locations without affecting surrounding regions, which is commonly used in in vivo Calcium imaging (Zariwala et al., 2012). Our technique of simultaneous optical reading and writing makes it possible to insert optrodes and guide them through brain tissue until they "sense" optical changes corresponding to the activity of target cells that express a Calcium indicator. This will reduce, to a great extent, the probability of off-target recordings and stimulations.

The synchronous connection between the KIWI and BCCS will likely lead to rapid advances in understanding the key circuits and language of the brain. The BCP provides researchers with a more thorough (and contextual) understanding of neural signaling patterns than ever before, enabling far more responsive brain-machine interfaces (for example, enabling a paralyzed patient to control a computer, quadcopter or mechanical prosthetic). A wireless implanted device might allow a PD patient to not only quell tremors but actually regain motor capacity, even just minutes after receiving an implant. By combining these technologies with behavioral and physiological metrics, we hope to open up new horizons for the analysis of cognition. Our multimodal diagnostic and analysis allows for an approach of analyzing brain machinery at higher data resolution. The data method could be considered a first step in progressing medicine from snapshots of macro anatomo-physiology to continuous, in-vivo monitoring of micro anatomo-physiology. The in-vivo study of a brain's parcel may give us a real-time relationship of the different components and their functionality, from which the complex functional mechanism of the brain machinery could be highlighted. Giving rise to new medical approaches of diagnosis, treatment, and research. More than one device may prove effective in allowing us to define a powerful new technique for brain-functional mapping, which could be used to systematically analyze and understand the interconnectivity of each brain region, along with the functionality of each region.

Therapeutic aims may include use of the device as a brain or cell stimulator, and indirect by data from recordings highlighting the mechanism(s) by which several diseases occur, owing to KIWI's ability to record a basic global neuronal state of a brain region and the dynamic neuronal interplay. The modifications which occur during its normal activity enable us to understand the neuronal properties and the function of a given brain region. Our device is able to give us the dynamic continuum of the whole activity of the considered region and thus provide important insights into the fundamental mechanisms underlying both normal brain function and abnormal brain functions (for example, brain disease). The potential for these findings to be translated into therapies are endless because this device may be used in any region of the brain and represents the first synthesis of a closed-loop neural modulator informed by internal and external conditions. The BCP provides a large amount of information and could be used to explore any brain disease within a real dynamic, in vivo condition. If successful, the potential of this device for the diagnosis of organic brain diseases is enormous and it could be an important complement to MRI for the diagnosis of non-organic disease.

Recent demonstrations of direct, real-time interfaces between living brain tissue and artificial devices, such as with computer cursors, robots and mechanical prostheses, have opened new avenues for experimental and clinical investigation of Brain Machine Interfaces (BMIs). BMIs have rapidly become incorporated into the development of 'neuroprosthetics,' which are devices that use neurophysiological signals from undamaged components of the central or peripheral nervous system to allow patients to regain motor capabilities. Indeed, several findings already point to a bright future for neuroprosthetics in many domains of rehabilitation medicine. For example, scalp electroencephalography (EEG) signals linked to a computer have provided 'locked-in' patients with a channel of communication. BMI technology, based on multi-electrode single-unit recordings, a technique originally introduced in rodents and later demonstrated in non-human primates, has yet to be transferred to clinical neuroprosthetics. Human trials in which paralyzed patients were chronically implanted with cone electrodes or intracortical multi-electrode arrays allowed the direct control of computer cursors. However, these trials also raised a number of issues that need to be addressed before the true clinical worth of invasive BMIs can be realized. These include the reliability, safety and biocompatibility of chronic brain implants and the longevity of chronic recordings, areas that require greater attention if BMIs are to be safely moved into the clinical arena. In addition to offering hope for a potential future therapy for the rehabilitation of severely paralyzed patients, BMIs can be extremely useful platforms to test various ideas for how populations of neurons encode information in behaving animals. Together with other methods, research on BMIs has contributed to the growing consensus that distributed neural ensembles, rather than the single neuron, constitute the true functional unit of the CNS responsible for the production of a wide behavioral repertoire.

When designing an interface between a living tissue and an electronic device, there are important factors to consider. Particularly, the structural and chemical differences between these two systems; an electrode's ability to transfer charge; and the temporal-spatial resolution of recording and stimulation. Traditional multi-electrode array (MEAs) for neuronal applications present several limitations: low signal to noise ratio (SNR), low spatial resolution (leading to poor site specificity) and limited biocompatibility (easily encapsulated with non-conductive undesirable glial scar tissue) which increases tissue injury and immune response (Bareket-Keren, L. & Hanein, Y., 2014b). Neural electrodes should also accommodate for differences in mechanical properties, bioactivity, and mechanisms of charge transport, to ensure both the viability of the cells and the effectiveness of the electrical interface. An ideal material to meet these requirements is carbon nanotubes (CNTs). CNTs are well suited for neural electrical interfacing applications owing to their large surface area, superior electrical and mechanical properties, and the ability to support excellent neuronal cell adhesion (Bareket-Keren, L. & Hanein, Y., 2014a, 2014b). Over the past several years it has been demonstrated as a promising material for neural interfacing applications. It was shown that the CNTs coating enhanced both recording and electrical stimulation of neurons in culture, rats and monkeys by decreasing the electrode impedance and increasing charge transfer (Keefer, E. W. et al., 2008). Related work demonstrated the single-walled CNTs composite can serve as material foundation of neural electrodes with chemical structure better adapted with long-term integration with the neural tissue, which was tested on rabbit retinas, crayfish in vitro and rat cortex in vivo (Chen, Y.-C. et al., 2011; Gabriel, G. et al., 2009; Kam, N. W. S., Jan, E., & Kotov, N. A., 2008; Yi, W. et al., 2015).

Using long CNTs implanted into the brain has many advantages, for instance an optical fiber with CNTs protruding from it (Kashiwagi, K. & Yamashita, S., 2009), but this technology has not been trialed in vivo or expanded to very large numbers of recording channels. Characterization in vitro showed that the tissue contact impedance of CNT fibers was lower than that of state-of-the-art metal electrodes, chronic studies in vivo in parkinsonian rodents also showed that CNT fiber microelectrodes stimulated neurons as effectively as metal electrodes (Vitale, F. et al., 2015). Stimulation of hippocampal neurons in vitro with vertically multi-walled CNTs electrodes suggested CNTs were capable of providing far safer and efficacious solutions for neural prostheses than metal electrode approaches (Wang, K. et al., 2006). CNT-MEA chips proved useful for in vitro studies of stem cell differentiation, drug screening and toxicity, synaptic plasticity, and pathogenic processes involved in epilepsy, stroke, and neurodegenerative diseases (Suzuki, I. et al., 2013). Nanotubes are a great feature for reducing adverse tissue reactions and maximizing the chances of high-quality recordings, but squeezing a lot of hardware into a small volume of tissue will likely produce severe astroglial reactions and neuronal death. At the same time, CNTs could extend the recording capabilities of the implant beyond the astroglial scar, without increasing the foreign body response and the magnitude of tissue reactions. Implantation of traditional, rigid silicon electrode arrays has been shown to produce a progressive breakdown of the blood-brain barrier and recruitment of an astroglial scar with an associated microglia response (Winslow, B. D. et al., 2010; Winslow, B. D. & Tresco, P. A., 2010).

Neural implant geometry and design is highly dependent on animal model used, where larger animals will see a somewhat less dramatic deterioration in recording quality and quantity, so early trials in rats probably shouldn't be too focused on obtaining very long-term recordings on a very large number of channels. While loss of yield due to abiotic failures is a manufacturing process and handling problem, biotic failures driven hostile tissue reactions can only be addressed by implementing design concepts shown to reduce reactive astrogliosis, microglial recruitment and neuronal death (Prasad, A. et al., 2012; McGonnell, G C. et al., 2009).

Conventional thin film probes can fit hundreds of leads into one penetrating shank (Seidl, K. et al., 2011; Torfs, T. et al., 2011). Rolling up a planar design would come with several benefits: first, it would decrease the amount of tissue damage a wide 2D-structure would produce. This is essential for the very high densities we are aiming for. Second, it would stiffen the probe, making it easier to penetrate tissue. Thirdly, a round cross section is preferable for reducing the foreign body response in the brain parenchyma. Finally, this design allows for potentially extremely dense architectures, as by combining several of these probes into a 10×10 array of 1 $cm^2$, an implant using this technology could potentially deploy several tens of thousands of leads in a multielectrode array, and could be conceivably combined with optical fibers for stimulation within an electronic-photonic microarray implant. Wise, K D., 2005 suggested that ideal design of an implantable electrode system is a 3D electrode array attached to a platform on the cortical surface. Said platform would be used for signal processing and wireless communication.

Why coatings or composites with CNT? The unique combination of electrical, mechanical and nanoscale properties of carbon nanotubes (CNT) make them very attractive for use in NE. Recent CNT studies have tried different CNT coatings or composites on metal electrodes and growing full electrodes purely from CNT (Wang, K. et al., 2006) (more references). Edward W. Keefer et al., (2008) was the first to do a recording study using different coatings made with CNT on electrodes. They found that CNT can help improve the electrode performance during recording by decreasing impedance, increasing charge transfer and increasing signal-to-noise ratio. CNT may improve the biological response to neural electrodes by minimizing risk of brain tissue rejection.

Why ICA for analysis? ICA signal separation is performed on a sample by sample basis where no information about spike shape is used (Lewicki, M. S. (1998)). For this reason, it is possible to achieve good performance of sorting accuracy in terms of misses and false positives, especially in cases where the background noise is not stationary but fluctuate throughout trials, which is the fact based on biophysical and anatomical considerations but is ignored by most current spike sorting algorithms (Rey, H. G., Pedreira, C., & Quiroga, R. Q. (2015)). One assumption underlying this technique is that the unknown sources are independent, which is the case under the assumption that the extracellular space is electrically homogeneous, pairs of cells are less likely to be equidistant from both electrodes (Rey, H. G., Pedreira, C., & Quiroga, R. Q. (2015)). The other assumption of this approach is that the number of channels must equal or greater than the number of sources, which can yield advantages for large-scaled recordings.

Exemplary tables of advantages of aspects of technologies that may be utilized by embodiments are shown in FIGS. 6 and 7.

Figure 8:
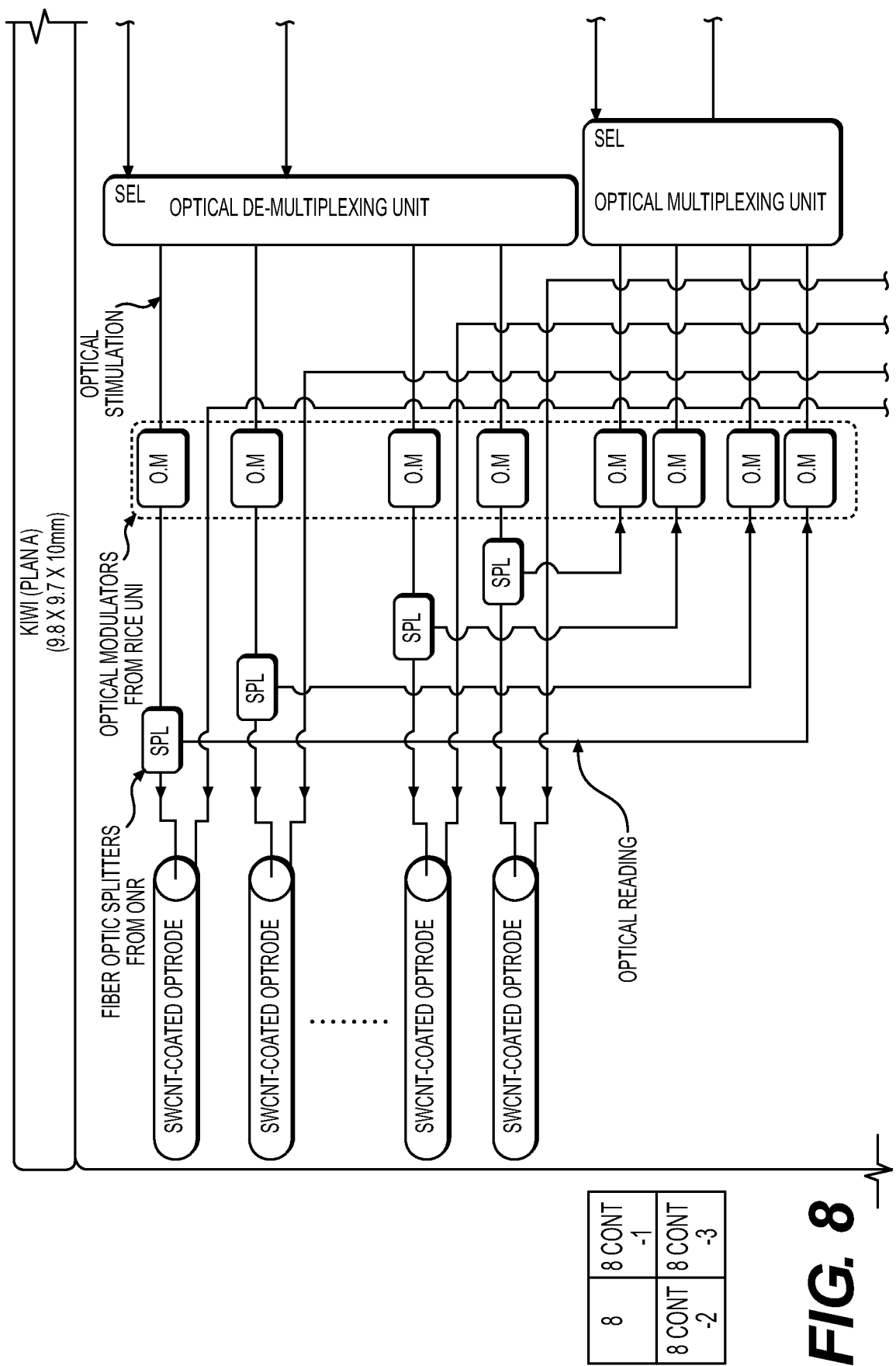
Figure 8:
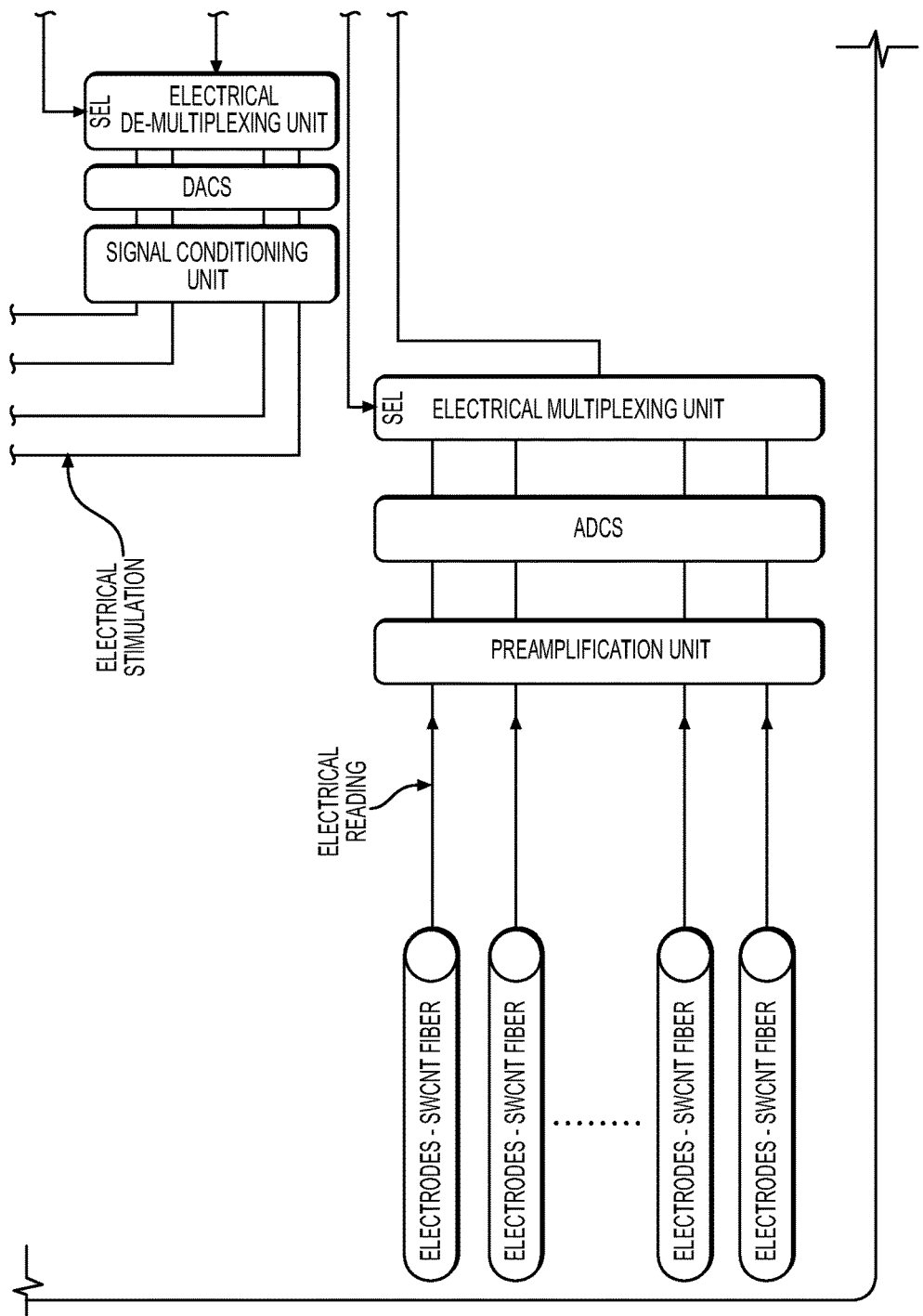
Figure 8:
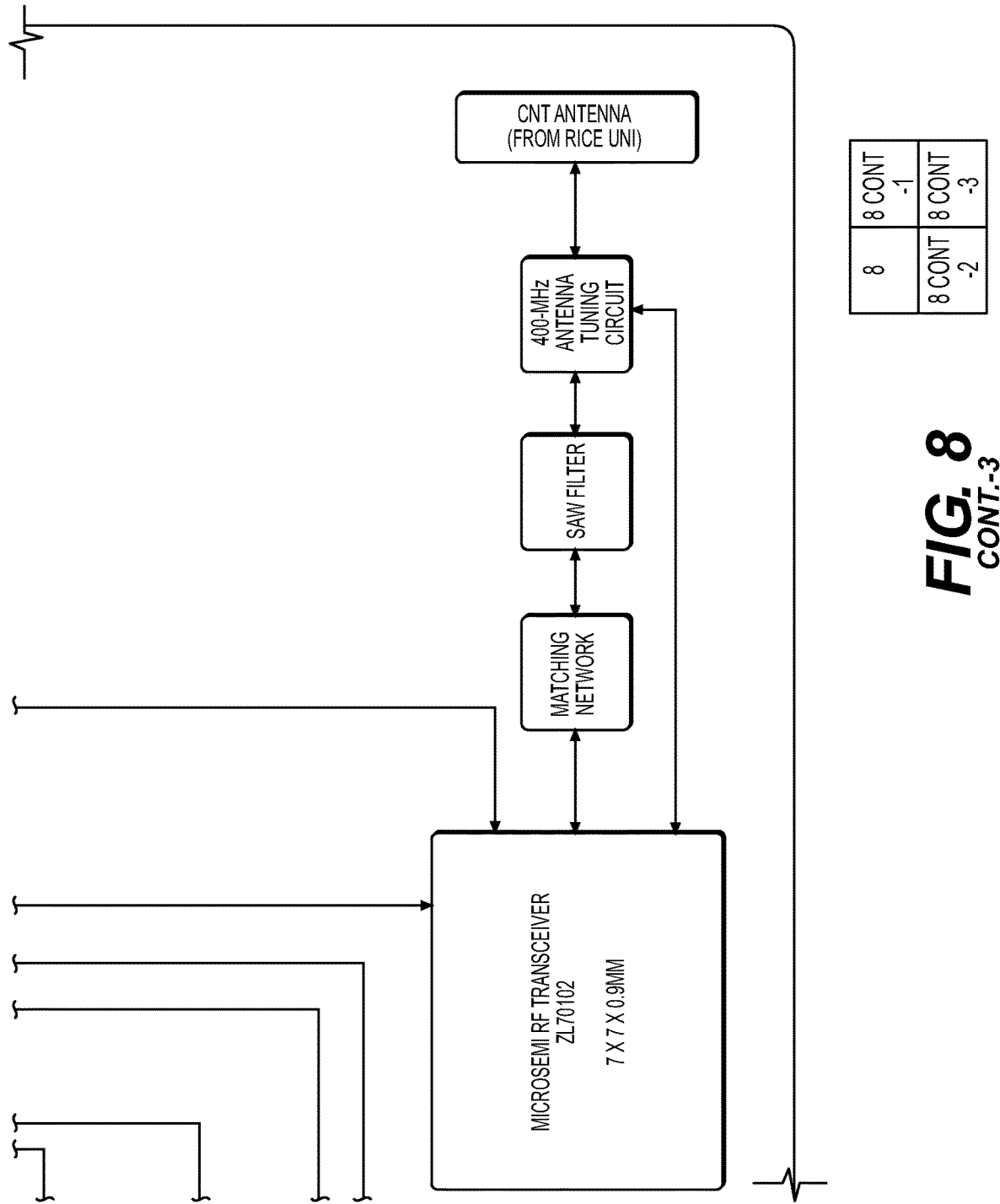

In an embodiment, the BCP hardware may be fabricated using electronic components available on the market today. In an embodiment, the KIWI may be made with a microfabricated carbon nanotube (CNT) neural interface, a light modulation and detection silicon photonic chip, and an independent Central Processing Unit (CPU) where all the processing will preside. RF communication between the KIWI and BCCS may carried out either by making use of the processor's Bluetooth capability or by implementing an independent RF transceiver in each of the two devices. The BCCS device may be calibrated to and securely integrated with the KIWI device. An exemplary block diagram of an embodiment of a KIWI device 800 is shown in FIG. 8.

Optogenetics enable the optical control of individual neurons, but even neurons with no genetic modification have light sensitivity, such as in a circuit mediated by neuropsin (OPN5), a bistable photopigment, and driven by mitochondrial free radical production. This bistable circuit is a self-regulating cycle of photon-mediated events in the neocortex involving sequential interactions among 3 mitochondrial sources of endogenously-generated photons during periods of increased neural spiking activity: (a) near-UV photons (~380 nm), a free radical reaction byproduct; (b) blue photons (~470 nm) emitted by NAD(P)H upon absorption of near-UV photons; and (c) green photons (~530 nm) generated by NAD(P)H oxidases, upon NAD(P)H-generated blue photon absorption. The bistable nature of this nanoscale quantum process provides evidence for an on/off (UNARY+/−) coding system existing at the most fundamental level of brain operation and provides a solid neurophysiological basis for the FCU. This phenomenon also provides an explanation for how the brain is able to process so much information with slower circuits and so little energy—quantum tunneling. Computers built from such material would be orders of magnitude faster than anything developed to date. The atomic scale of CNTs could potentially enable interfacing with this naturally optosensitive layer of the brain in the future, a system many orders of magnitude smaller than the neuron.

Figure 9:
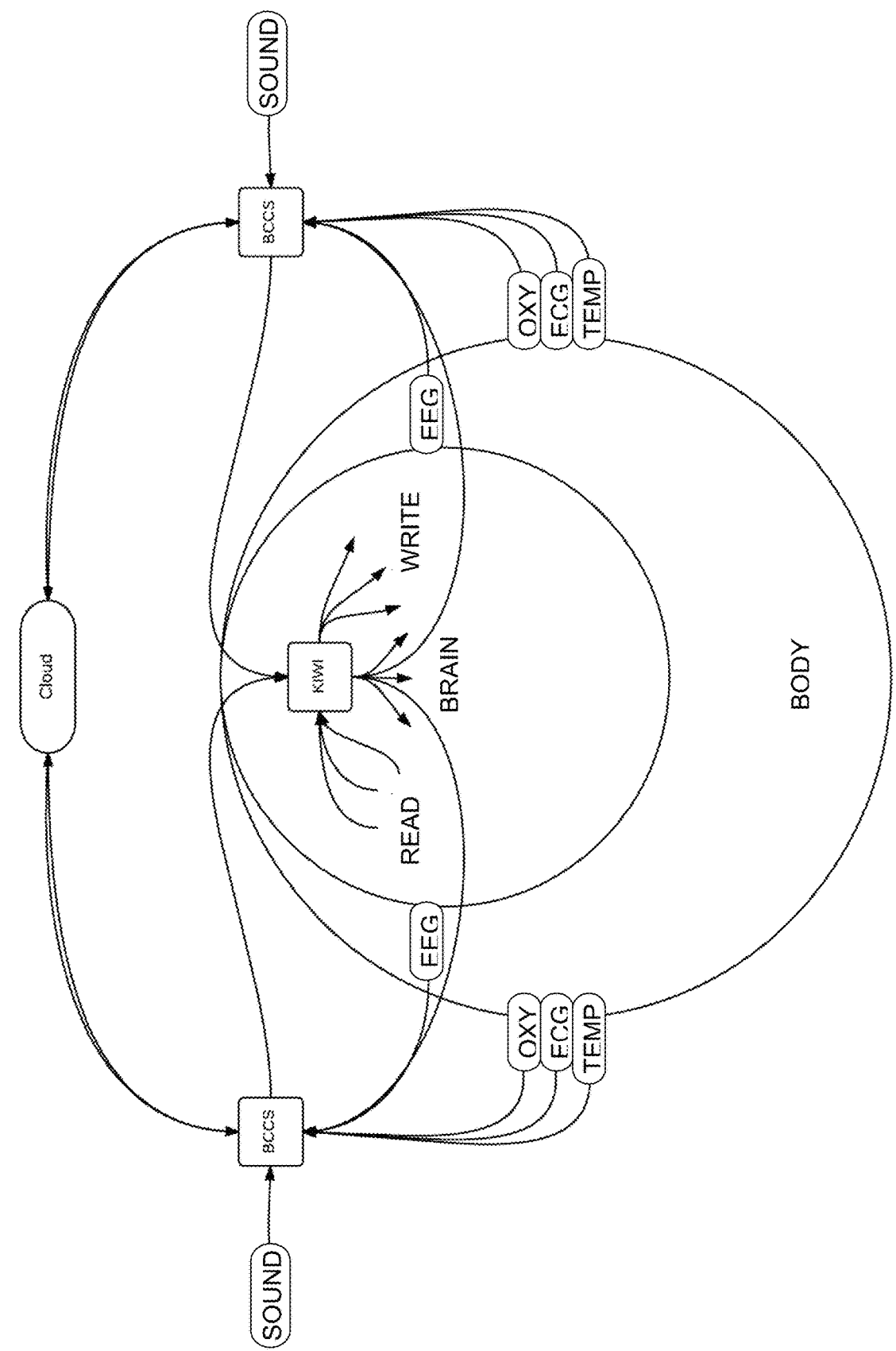
FIG. 9 illustrates an exemplary flow diagram of a process of Behavioral and Cognitive Monitoring.

In an embodiment, the BCCS earbuds may have DSP which may be used for processing of data from the KIWI implant. These earbuds may be able to capture EEG, ECG, PulseOx, QT intervals, BP, HR, RR, true body temperature, body posture, movement, skin conductance, and vestibular data. The device and all of its data streams will need to be programmed and synchronized to the coding system and the frequency of the KIWI. A body sensor network can provide a rich set of multimodal data to enable the earbuds and BCP to dynamically correlate internal states in the KIWI with external states observed by the BCCS, a process which will effectively map neural pathways and function. An exemplary process of behavioral and cognitive monitoring is shown in FIG. 9.

Figure 10:
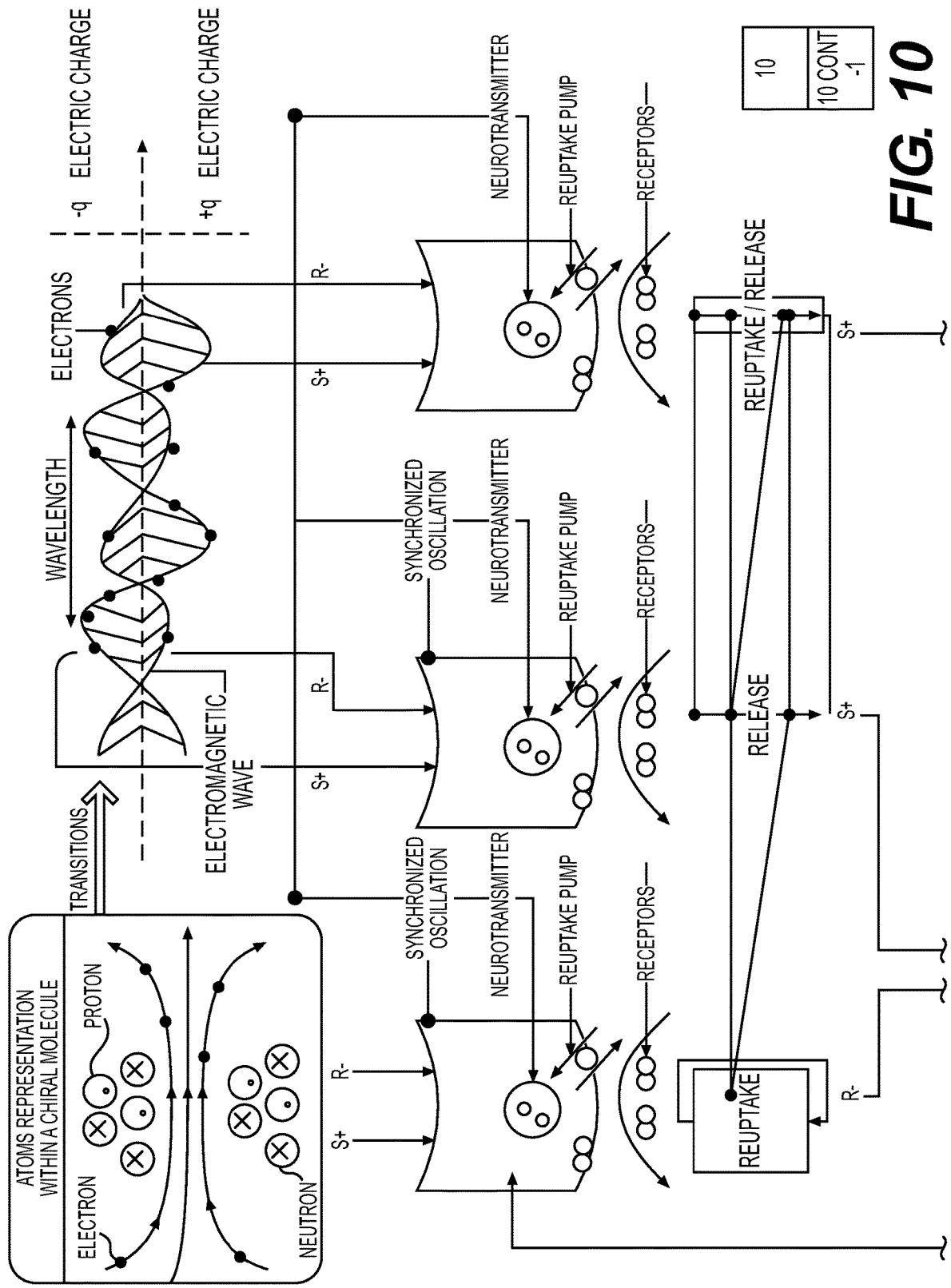
Figure 10:
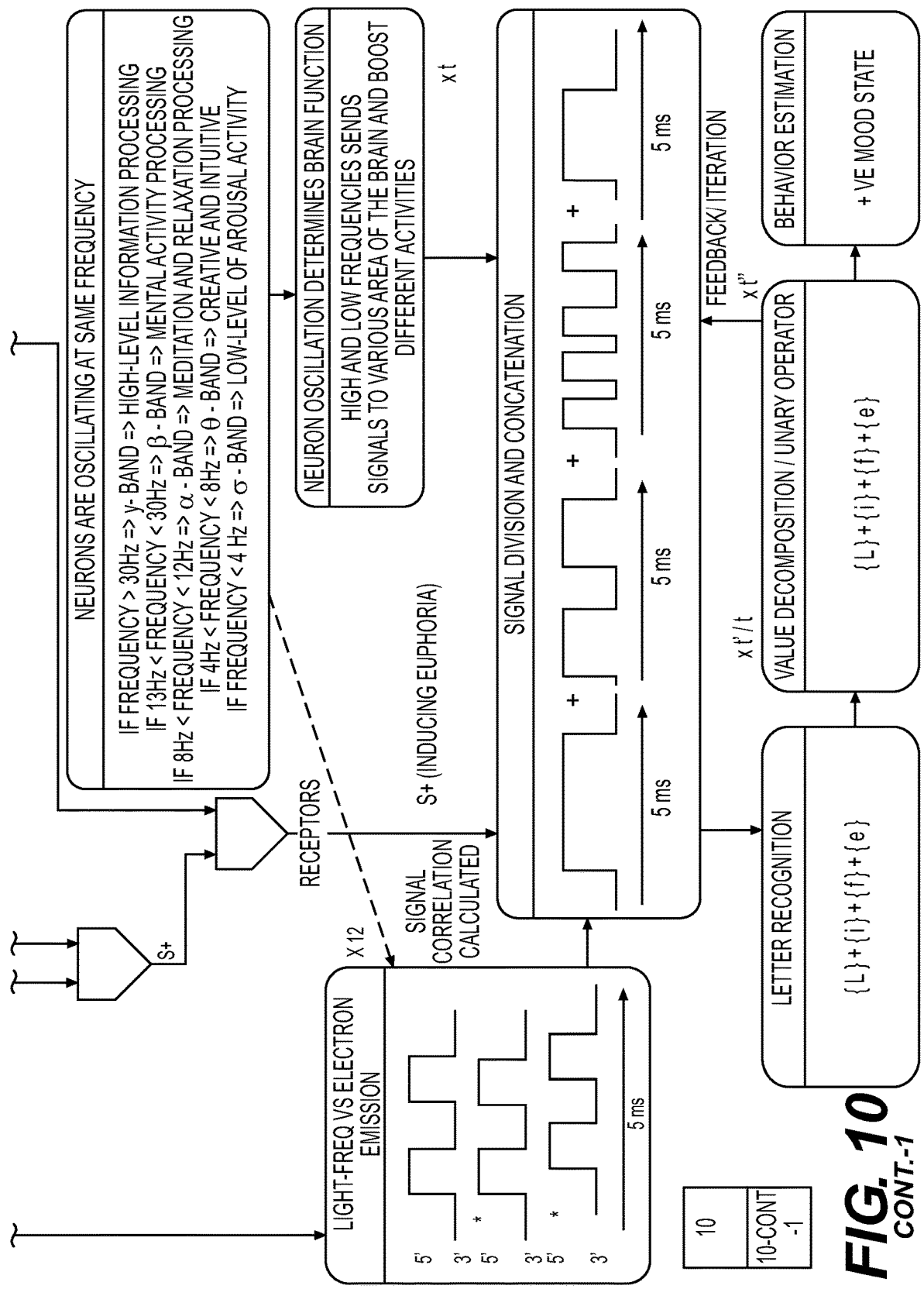

Behavior is the macroscopic expression of neural activity, implemented by muscular and glandular contractions acting on the body, and resulting in egocentric and allocentric changes in an organized temporal sequence. In general, behavior is relational, which is the confluence of an embodied brain with its environment. It is also dynamic, in which change is both accidental and essential. And it is usually high dimensional, making it complex and variable (unpredictable). An example of factors linking behavior with neural, muscular, glandular, and genetic activities is shown in FIG. 10.

In an embodiment, the BCP system may include a BCCS earbud multi sensor system or the like, a Texas Instruments Chronos watch or the like, which is a highly integratable, wearable and wireless system that can measure acceleration at the wrist to collect dominant arm movement data. An Invensense MotionFit system or something similar, which incorporates a 3-axis gyroscope, microcontroller, Bluetooth, and embedded software for a fast and easy development can be used to measure head movement and balance.

Data Analysis Transformation Algorithms, B2D brain-to-digital transformation algorithms. The brain to digital transformation algorithm is a multi-input, multi-output predictive model which is a mapping from population neural responses to a multiple dimensional stimulus representation. First, we record neural signals while the animals/humans are listening some acoustic waveforms. Audio-induced cortical field potentials recorded by the KIWI implant are used to fit our multi-input, multi-output model for offline decoding. The inputs of the transform algorithm are time-varying neural signals at multiple electrodes, and the outputs are a spectrogram consisting of time-varying spectral power across a range of frequencies. And then we use a leave-one-out cross-validation fitting procedure in which the reconstruction model is trained on stimulus-response data and evaluated by directly comparing the original and reconstructed spectrograms of the out-of-sample recording.

By different choices of stimulus representation, we can develop the linear and nonlinear models. The linear model assumes a linear mapping between neural responses and the auditory spectrogram. The nonlinear model assumes a linear mapping between neural responses and the modulation representation. This mapping can be estimated using many different learning algorithms: 1) Regularized linear regression algorithm to minimize the mean-square error between the original and reconstructed stimulus; 2) Support vector machines (SVMs) to construct a hyperplane or set of hyperplanes in a high or infinite-dimensional space; 3) Convolutional Neural Network (CNN) to use minimal amounts of preprocessing with one or more convolutional layers (often with a sub sampling step) and one or more fully connected layers as in a standard multilayer neural network; 4) Online real-time Sequential Extreme Learning Machine Algorithm (OS-ELM) to learn the data one-by-one or chunk-by-chunk with fixed or varying chunk size, which was shown similar or better accuracies with at least an order-of-magnitude reduction in the learning time on non-stationary time series prediction. 5) Gradient Boosted Regression Trees ensemble algorithm to generalize prediction models by allowing optimization of an arbitrary differentiable loss function. With the KIWI implant and the B2D brain-to-digital transformation algorithm, we will explore the following research:

1) Reconstruct the sound; early auditory system decomposes speech and other complex sounds into elementary time-frequency representations, producing a rich representation of the spectro-temporal properties of the sound waveform. With the KIWI implant and the B2D transformation algorithm, we are looking at which neurons are increasing activity at particular acoustic frequencies, and from that we can map back to the sound. In this way, it is possible to reconstruct the stimulus from the measured population neural responses.

2) Target sound extraction and selection mechanisms; Animals can selectively respond to a target sound despite simultaneous distractors, just as humans can respond to one voice at a crowded cocktail party. With the KIWI implant and the B2D transformation algorithm, we can record multiple neuron activities in primary auditory cortex (A1) and medial prefrontal cortex (mPFC) while humans or animal are selectively responding to a target sound from a mixture to investigate the underlying neural mechanisms.

3) Audio-place association mechanisms; Stimulus-place associative task requires humans or animals to associate different stimuli with different locations. With the KIWI implant and the B2D transformation algorithm, here we will figure out how humans or animals integrate information about sensory stimuli and spatial locations to perform the audio-place associative task, thus build the local and transcortical circuits underlying audio-place mapping. Sensory and spatial information are initially processed in largely separate sub-regions of the brain, in our study we record the population neural responses of A1 and mPFC to study the audio-place association mechanisms and circuits.

Data Analysis Transformation Algorithms, D2B digital 2 brain transformation algorithms. Optogenetics may provide control over defined events within defined cell types at defined times—a level of precision that is most likely crucial to biological understanding even beyond neuroscience (Deisseroth, K. (2010)). The significance of any event in a cell has full meaning only in the context of the other events occurring around it in the rest of the tissue, the whole organism or even the larger environment. The millisecond-scale timing precision within behaving mammals has been essential for key insights into both normal brain function and into clinical problems such as Parkinsonism. Depending on the target cell population, some form of processing will be required in addition to standard auditory encoding and pulse modulation. Here we described the algorithm framework of digital-to-brain transformation, which includes three stages: Encode external auditory stimuli, choose appropriate multiple stimulation sites, and select effective stimulation parameter set.

First, encode external auditory stimuli; the first stage is to capture and encode the external auditory stimuli needed to be sent to the auditory cortex at high speed without significant lag. Sound waves are what physicists call longitudinal waves, which consist of propagating regions of high pressure (compression) and corresponding regions of low pressure, described by several basic physics features: waveform, amplitude, frequency, and wavelength. Via Fourier analysis, we can encode the external auditory stimuli into the sum of sinusoids and get its components.

Second, choose appropriate multiple stimulation neurons to be activated or silenced in a temporally-precise fashion;

the second stage is to choose appropriate multiple stimulation neurons to be activated or silenced. Dynamic audio compression techniques could be used to nonlinearly spatially compress the auditory file such that non-important features are compressed leaving important features the same size. Primary auditory neurons are known tonotopically mapped (that is, frequencies are kept in an ordered arrangement). From our brain to digital algorithms, we can obtain the tonotopic map of the auditory cortex and the linear or nonlinear model between stimuli and response. With the transformation models and the tonotopic map of the auditory cortex, we can choose the appropriate multiple stimulation neurons to be activated or silenced which are involved in specific tasks of identifying and segregating auditory objects and identifying the location of a sound in space.

Figure 11:
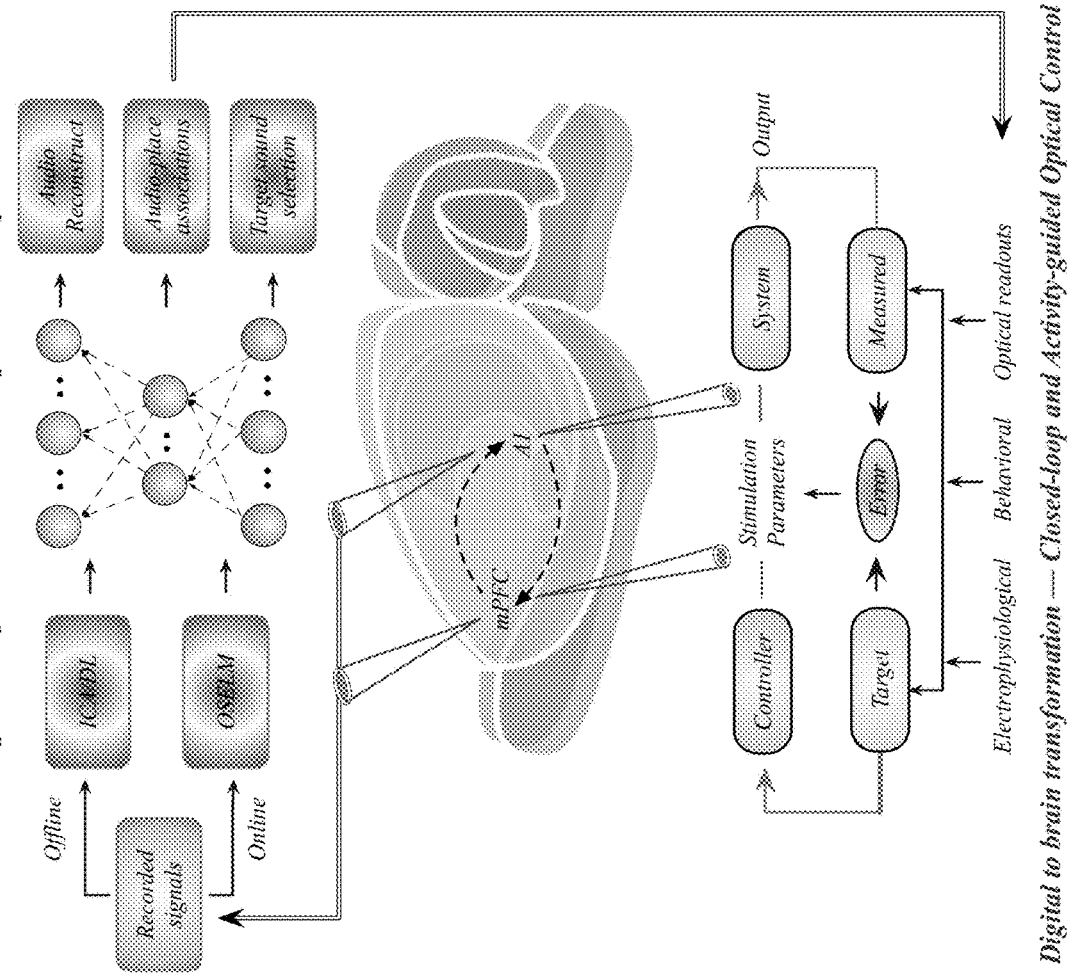
FIG. 11 illustrates an example of a write/read closed loop algorithm framework.

An example of a write/read closed loop algorithm framework on, for example, a rat's brain is shown in FIG. 11.

Third, select effective stimulation parameter set; the third stage is to take into account the effective stimulation parameter set which is bypassed by our KIWI implant. In a system the first stage is to understand the world and as such extracts particular stimulus features, which are sent to the auditory cortex for higher level analysis. As a computational system it is particularly tractable for analysis and modeling. So a pulse encoding scheme of stimulation parameter set is required to emulate the signal. Here we use the closed-loop and activity-guided optical control of neural circuit dynamics to produce the stimulation parameter set.

Closing the loop optogenetically (i.e., basing optogenetic stimulation on simultaneously observed dynamics in a principled way) is a powerful strategy for causal investigation of neural circuitry (Grosenick, L., Marshel, J. H., & Deisseroth, K. (2015). In particular, observing and feeding back the effects of circuit interventions on physiologically relevant timescales is valuable for directly testing whether inferred models of dynamics, connectivity, and causation are accurate in vivo. Closed-loop control could guide perturbations of neural systems (neurons and circuits) to achieve sophisticated, real-time control over neural dynamics and desired animal behavior, and thus to refine and confirm circuit-based models of the underlying system in the process (Grosenick, L., Marshel, J. H., & Deisseroth, K. (2015). In closed-loop optogenetics, the control input is a structured, time-varying light stimulus that is automatically modulated based on the difference between desired and measured outputs, which may include behavioral, electrophysiological, or optical readouts of activity generated by the biological system. It can be used to explore adaptation, plasticity, and neural state changes, as well as online tuning of optogenetic inputs in vivo (to achieve specific output parameters), and online system-identification of neural circuits (that is, choosing optogenetic stimuli online to reverse engineer neural circuits by causally establishing functional circuit architecture).

Data Analysis—How to identify single cells and their activity in the time domain. Traditional spike sorting methods were developed based on the basic strategy of matched filtering to compare the electrode waveform against a temporally sliding template. The clustering based spike sorting methods are developed from the matched filtering strategy, which usually include detecting putative spikes, extracting a variety of geometric wavelets, and grouping the points in the feature space into clusters (Rey, H. G., Pedreira, C., & Quiroga, R. Q. 2015). With the assumption of stereotyped spike waveforms for individual neurons, many conventional waveform based spike sorting algorithms will fail when overlapped spikes from two or more cells are superimposed, which will be more severe for synchronous or near-synchronous spikes (Pillow, J. W., Shlens, J., Chichilnisky, E. J., & Simoncelli, E. P. 2013). And it is also difficult to put the action potentials from the same neuron into a single group when they change shapes, for example in the case of high frequency bursts of spikes. Besides, detecting the subthreshold membrane potential fluctuations is also a big challenge for the current spike sorting algorithms.

Data Analysis Automated Spike Sorting Algorithms—For example, embodiments of the present invention may use fully automated spike sorting algorithms, to replace the waveform-based clustering techniques used today. Independent Component Analysis (ICA) is a blind source separation technique that does not operate under the assumptions that cause unavoidable errors in waveform-based clustering techniques, and may form the basis for a trusted spike sorting. The most promising advantage of ICA is that the signal separation is performed on a sample by sample basis where no information about spike shape is used (Lewicki, M. S. 1998). Overall, ICA can obtain good performance to convert spatiotemporal patterns of neural population activity into digital stimulus in these ways: remove artifacts; separate overlapping action potentials; recover action potential of different shapes from the same neurons; detect subthreshold membrane potentials and potential fluctuations; find the position of each neuron on the detector array to construct the topographic map.

Figure 13:
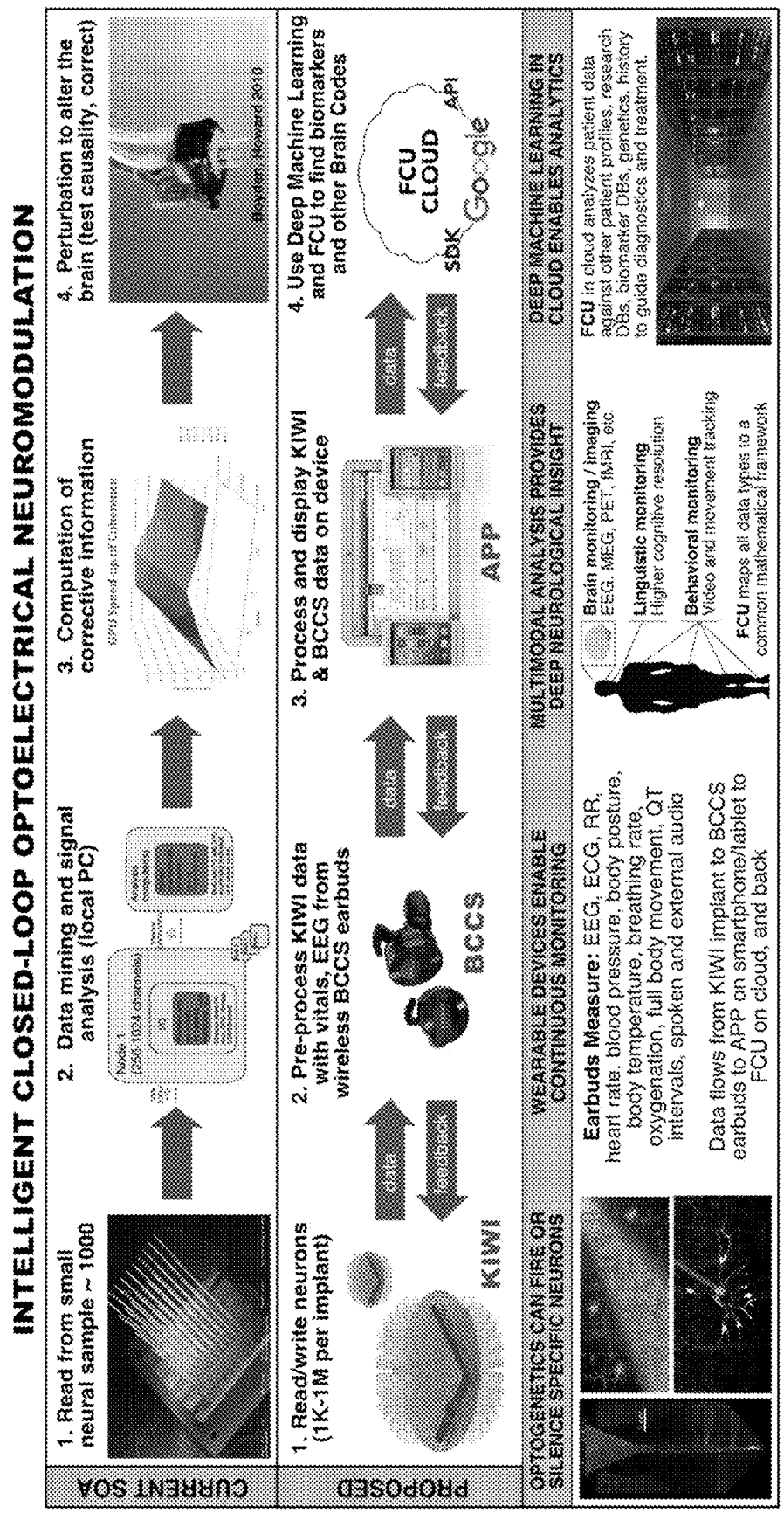
FIG. 13 illustrates an exemplary embodiment of intelligent closed-loop opto-electrical neuromodulation.
Figure 14:
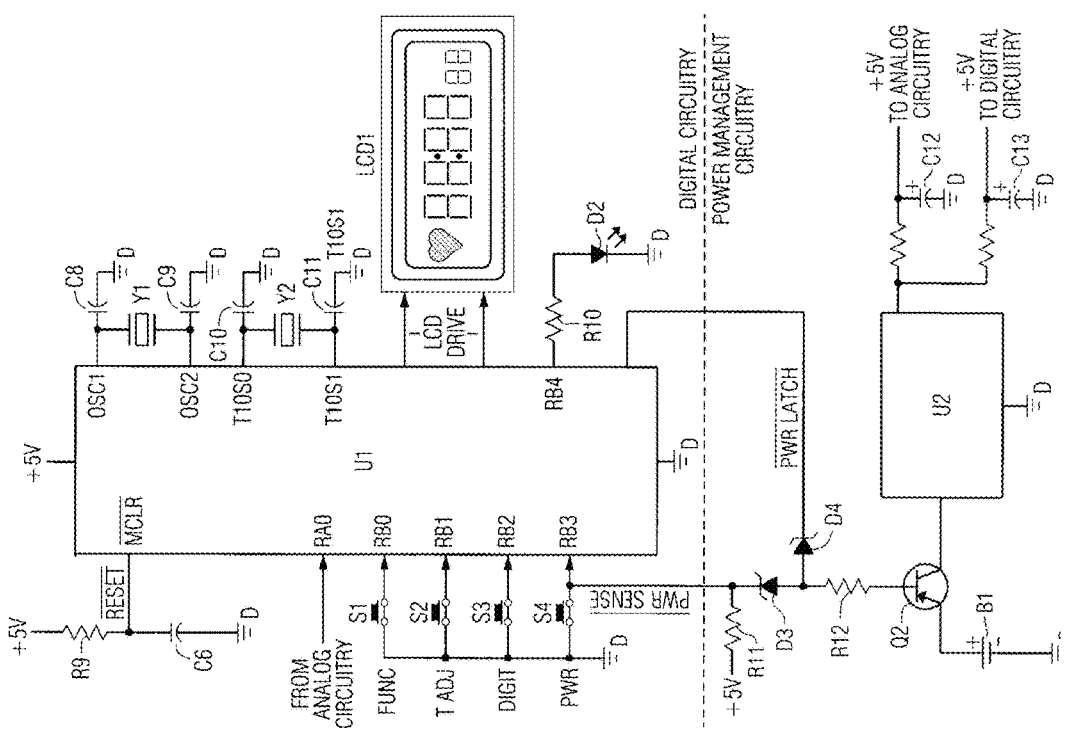
FIG. 14 illustrates an exemplary embodiment of an Electro Cardiogram circuit.
Figure 15:
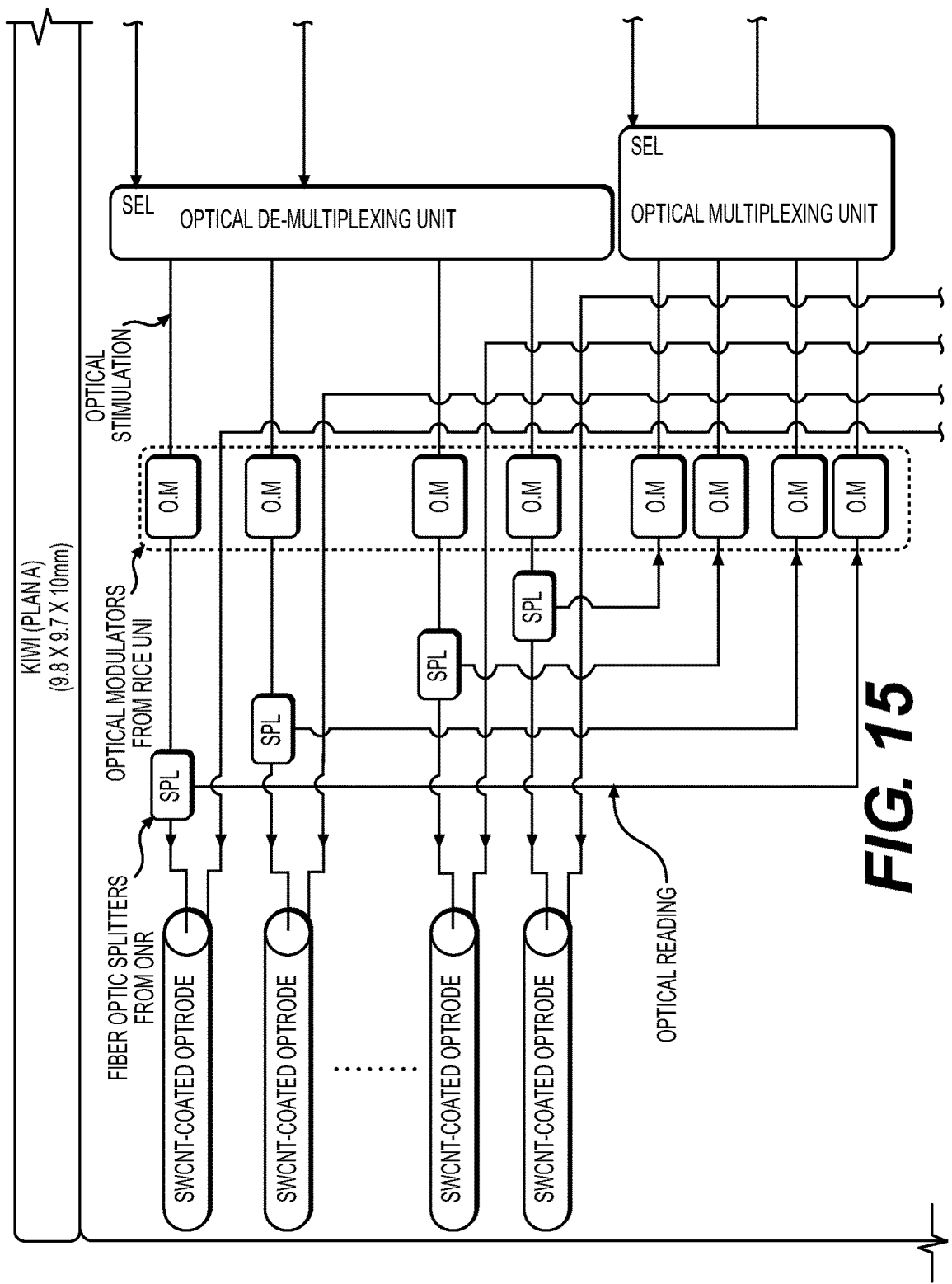
Figure 15:
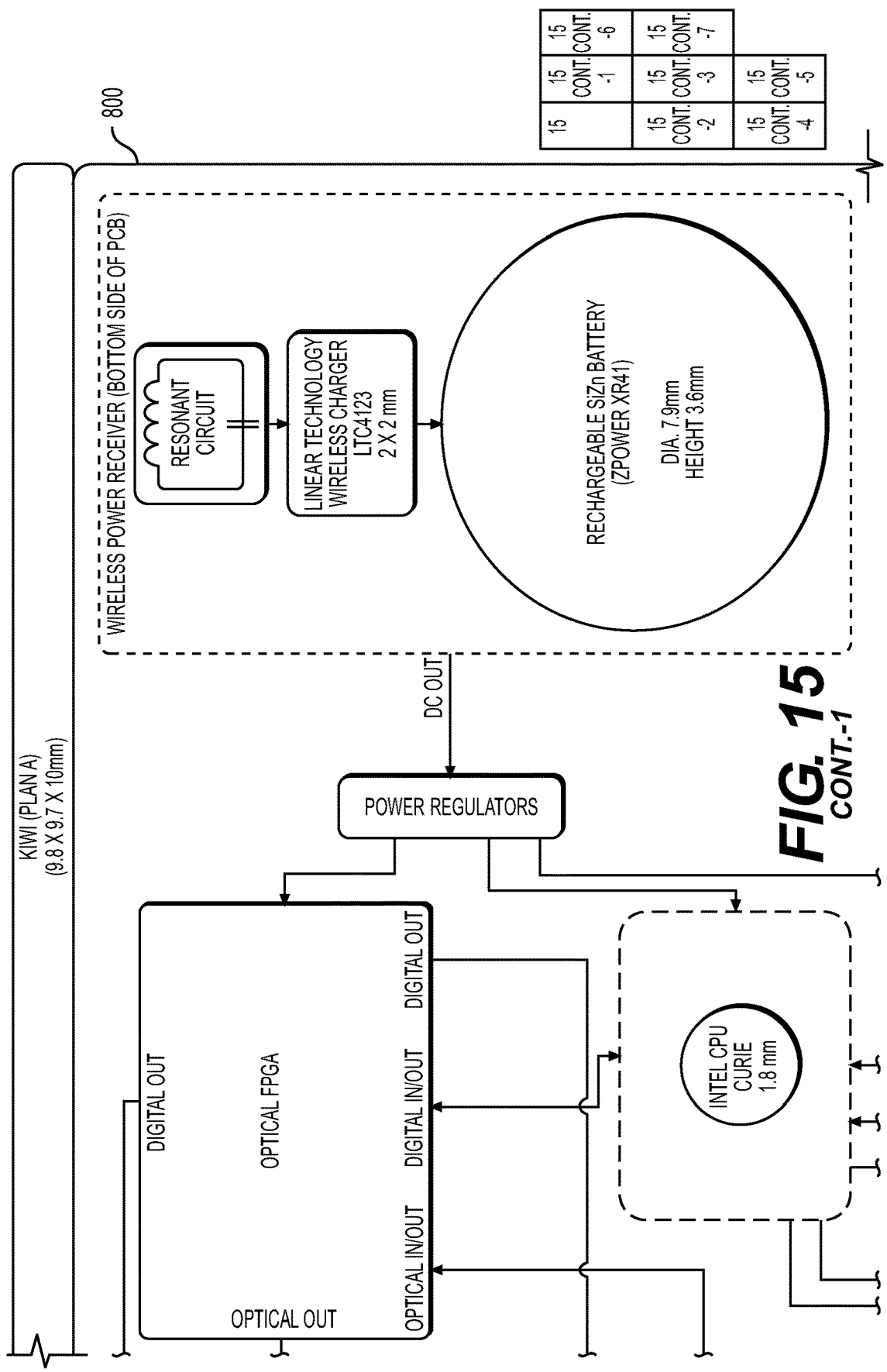
Figure 15:
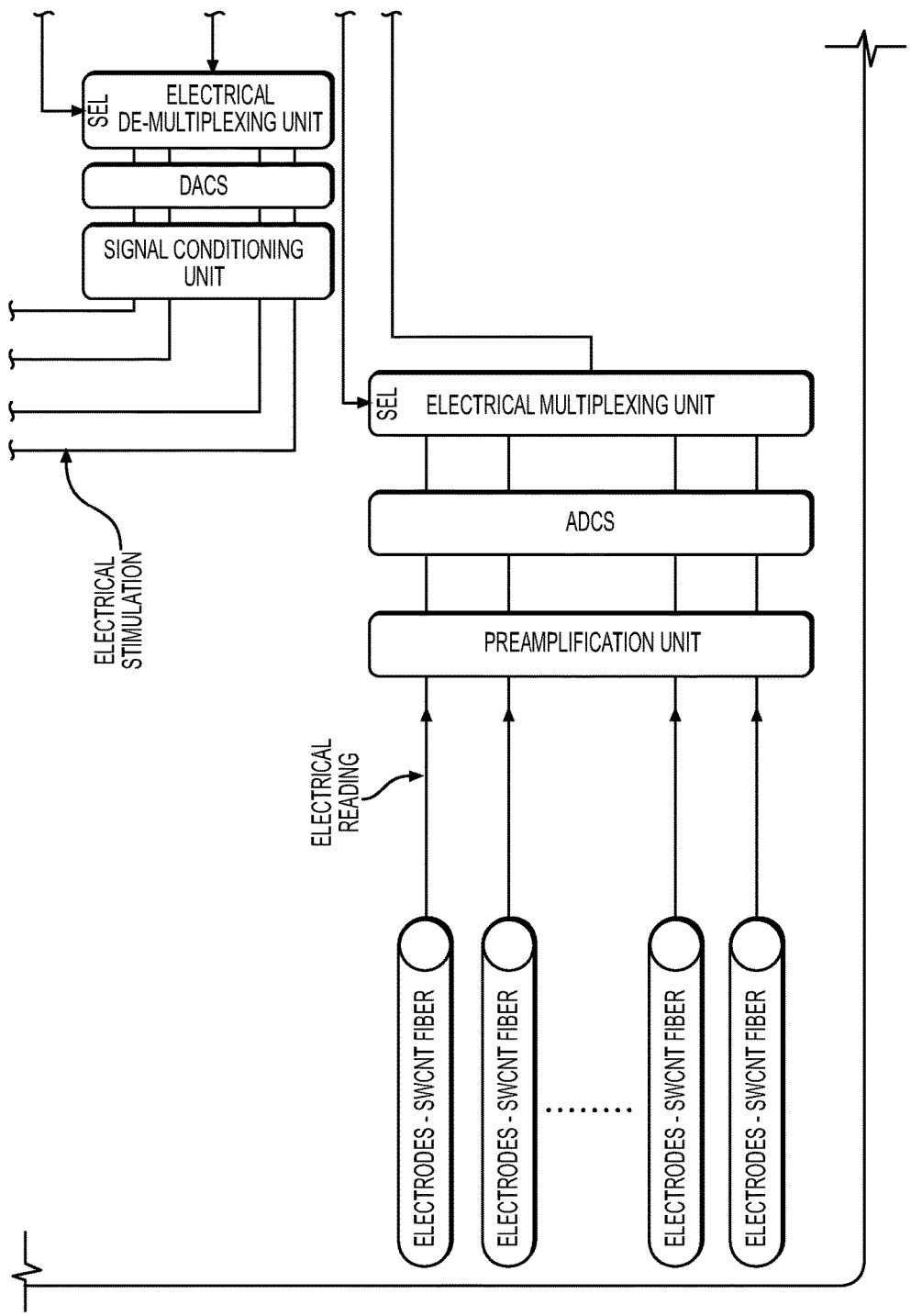
Figure 15:
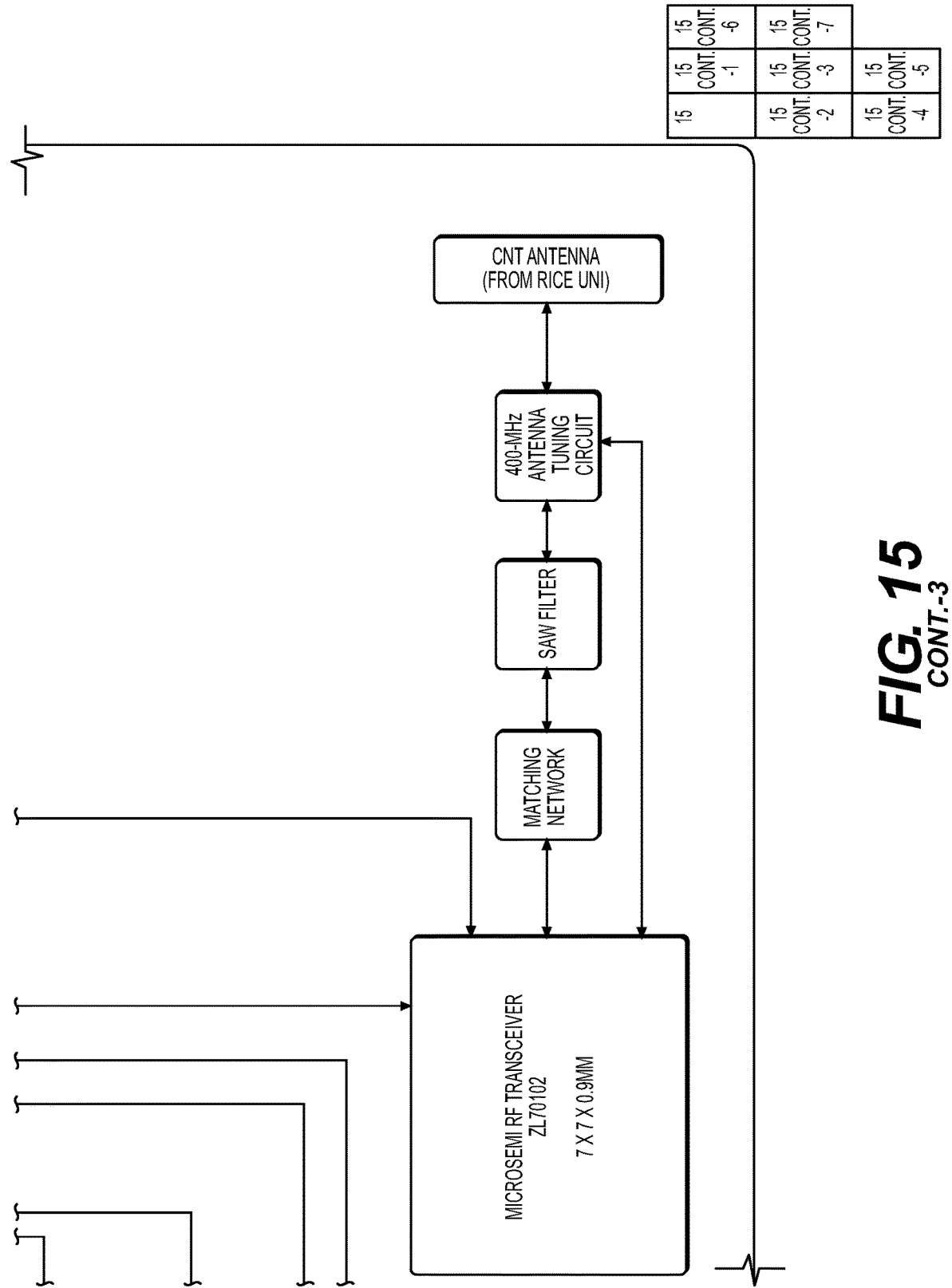
Figure 15:
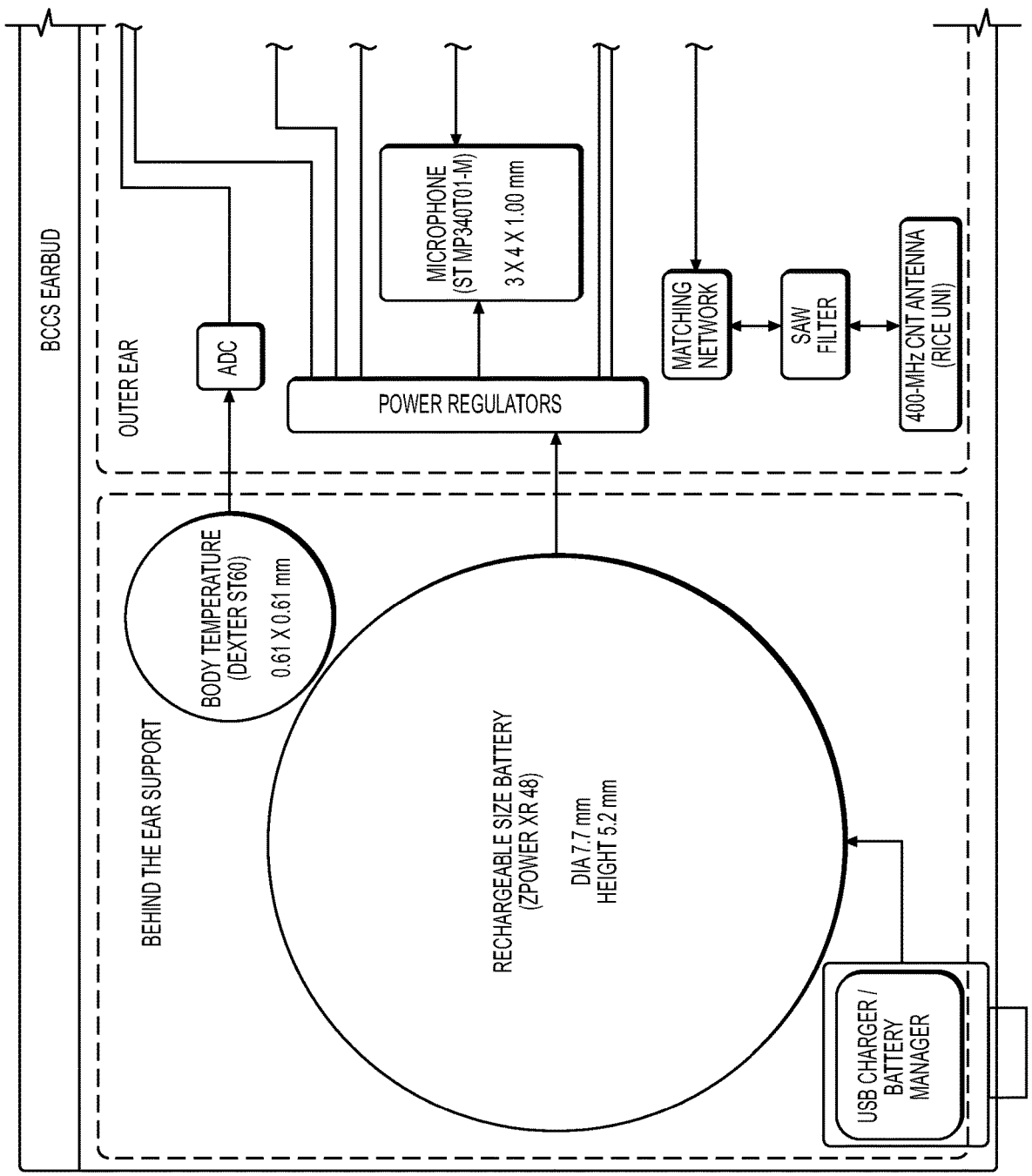
Figure 15:
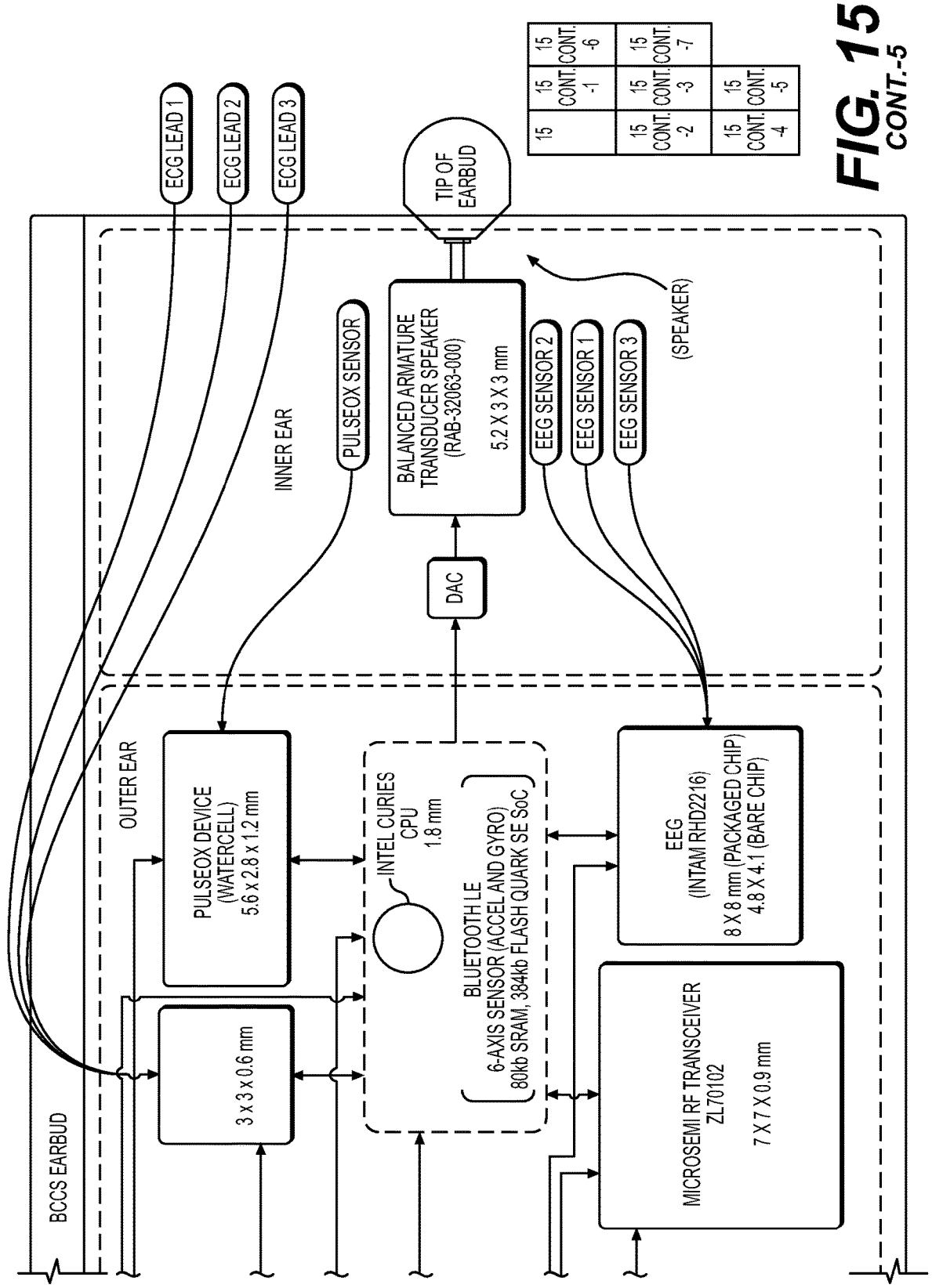
Figure 15:
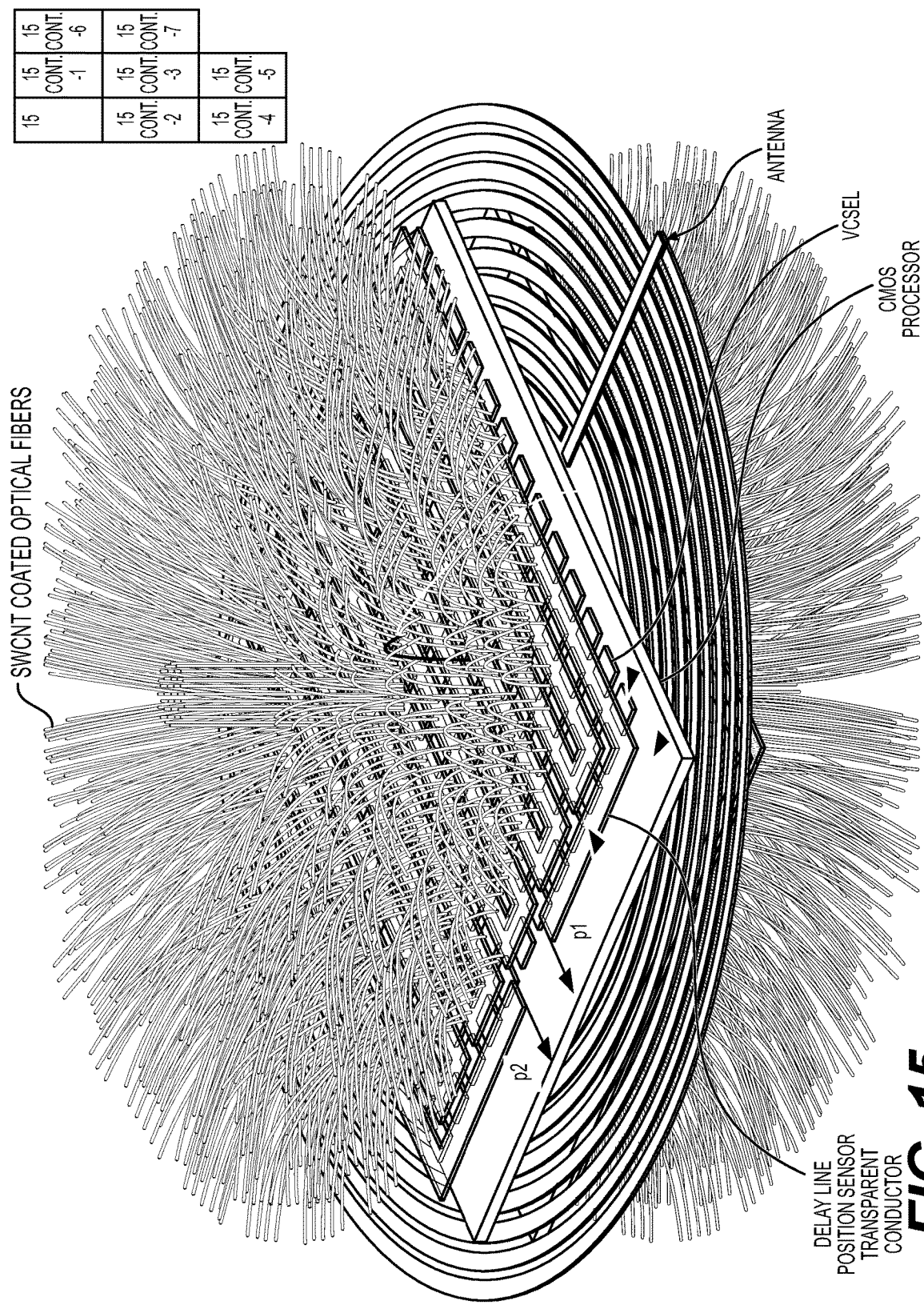

FIG. 12 illustrates examples of objectives and advantages of embodiments of the present invention. FIG. 13 illustrates an exemplary embodiment of intelligent closed-loop opto-electrical neuromodulation. FIG. 14 illustrates an exemplary embodiment of an Electro Cardiogram circuit. FIG. 15 illustrates an exemplary embodiment of a Biological Co-processor System.

For example, embodiments of the present invention may provide a neural oscillation monitoring system. The monitoring system may be configured to receive, process, detect, and optimize performance for a wide range of activities that may be recorded using electrophysiological monitoring devices. The monitoring system may allow raw EEG signals measured and be inputted into the system to undergo signal processing. Machine learning may then be used to classify the signals into groups pertaining to subject cohorts. The results of the monitoring system may be utilized for several applications. For example, the results may be used to detect EEG patterns of specific brain functions or dysfunctions such as mood states or neurological disorders. Another example may be utilizing these EEG patterns to optimize fitness training modules.

In an embodiment, the present invention may provide software that is compatible with a variety of off-the-shelf EEG sensors. Another embodiment may provide a software application integrated into a gaming or fitness equipment console for personalized fitness. Another embodiment may provide a software mobile application. Another embodiment may provide a novel EEG sensor that can acquire and analyze/monitor EEG data. Another embodiment may provide a novel EEG sensor that communicates wirelessly with a mobile application neural oscillation monitoring software.

In an embodiment, a neural oscillation monitoring system may provide objective brain function monitoring and may provide results in real-time. Given the automated nature, the invention may be portable in a software or hardware application.

In an embodiment, the present invention may involve input of raw EEG signals, processing, detecting, and utilizing the raw EEG signals for a variety of applications. The raw signals may first be pre-processed to remove artifacts and filter the frequencies of interest. The pre-processing may be performed in several ways, such as band-pass filtering, artifact removal by averaging, common spatial pattern processing to select EEG electrodes based on current source/signal localization, and segmentation of the EEG recordings. A variety of different signal processing tools may be utilized, and analysis in the three domains of EEG signals is shown as examples. In the time domain, spindle threshold analysis may be performed. In the frequency domain, power spectrum analysis may be performed. In the time-frequency domain, wavelet analysis may be performed. Features from these signal processing steps may be selected based on EEG signals or biomarkers of interest and may be used in machine learning. Several machine learning tools may be employed, such as nearest neighbors, support vector machines (SVM), and naive Bayes.

Figure 16A:
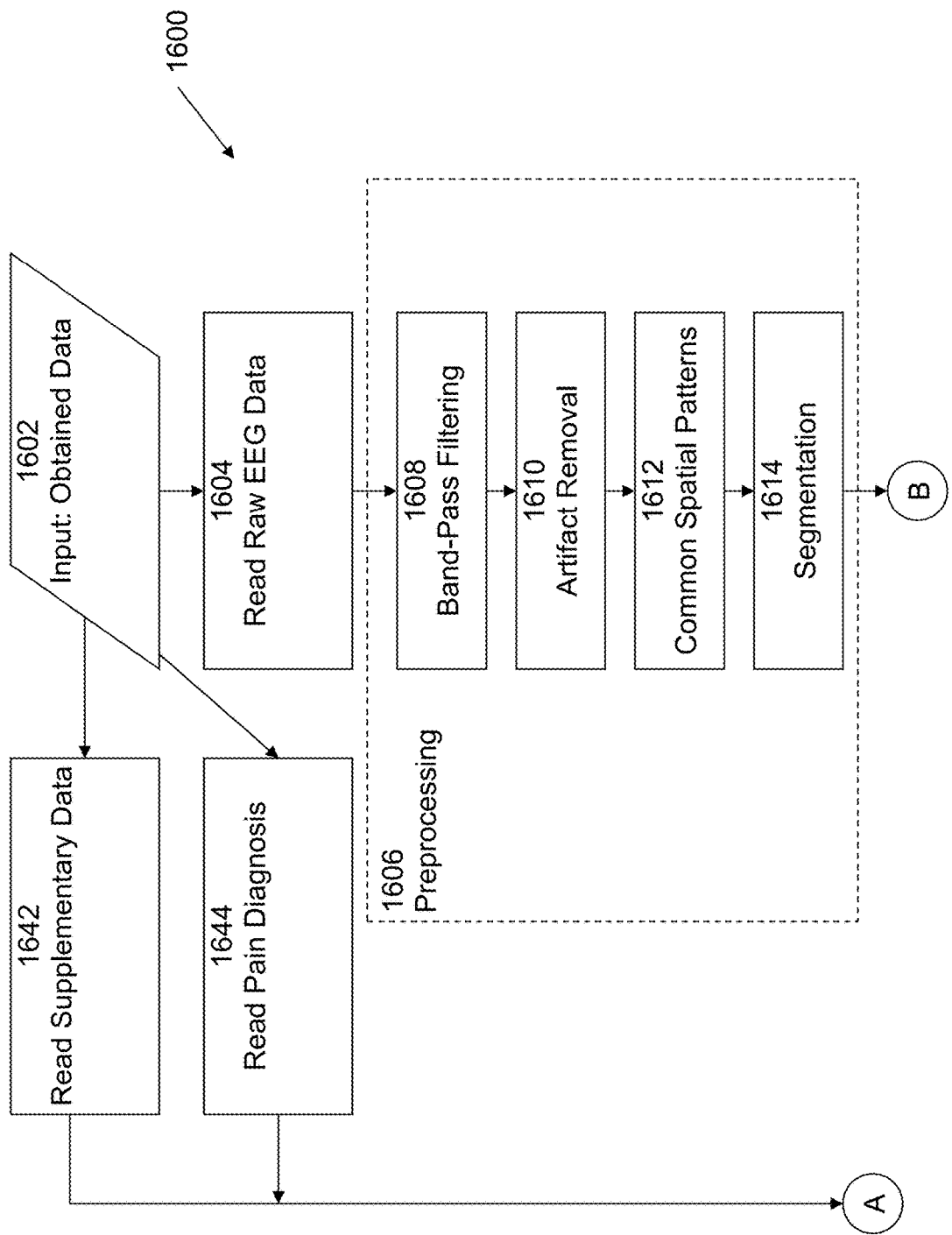
FIGS. 16a, 16b, and 16c illustrate an exemplary flow diagram of a process according to an embodiment of the present invention.
Figure 16B:
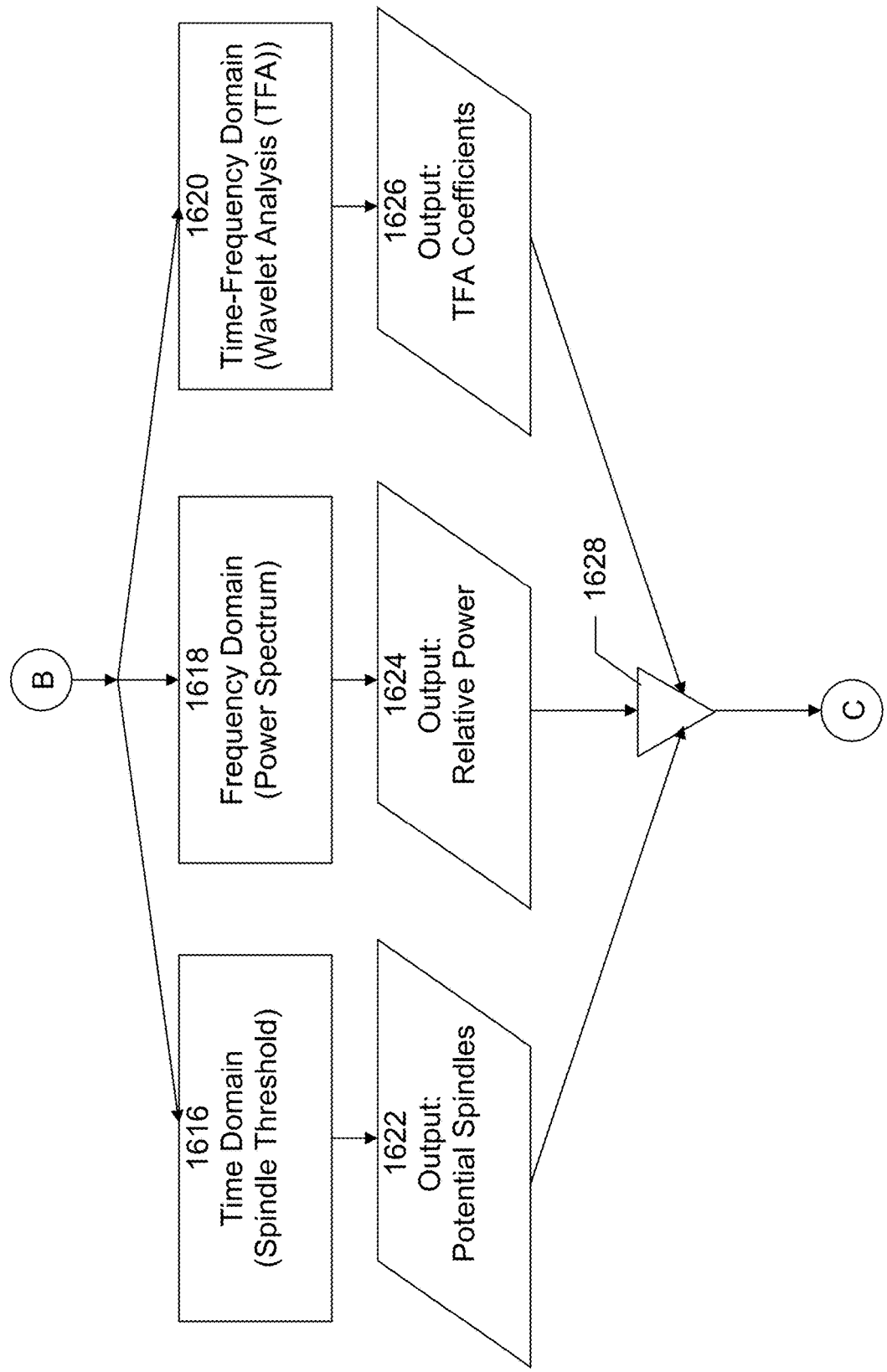
Figure 16C:
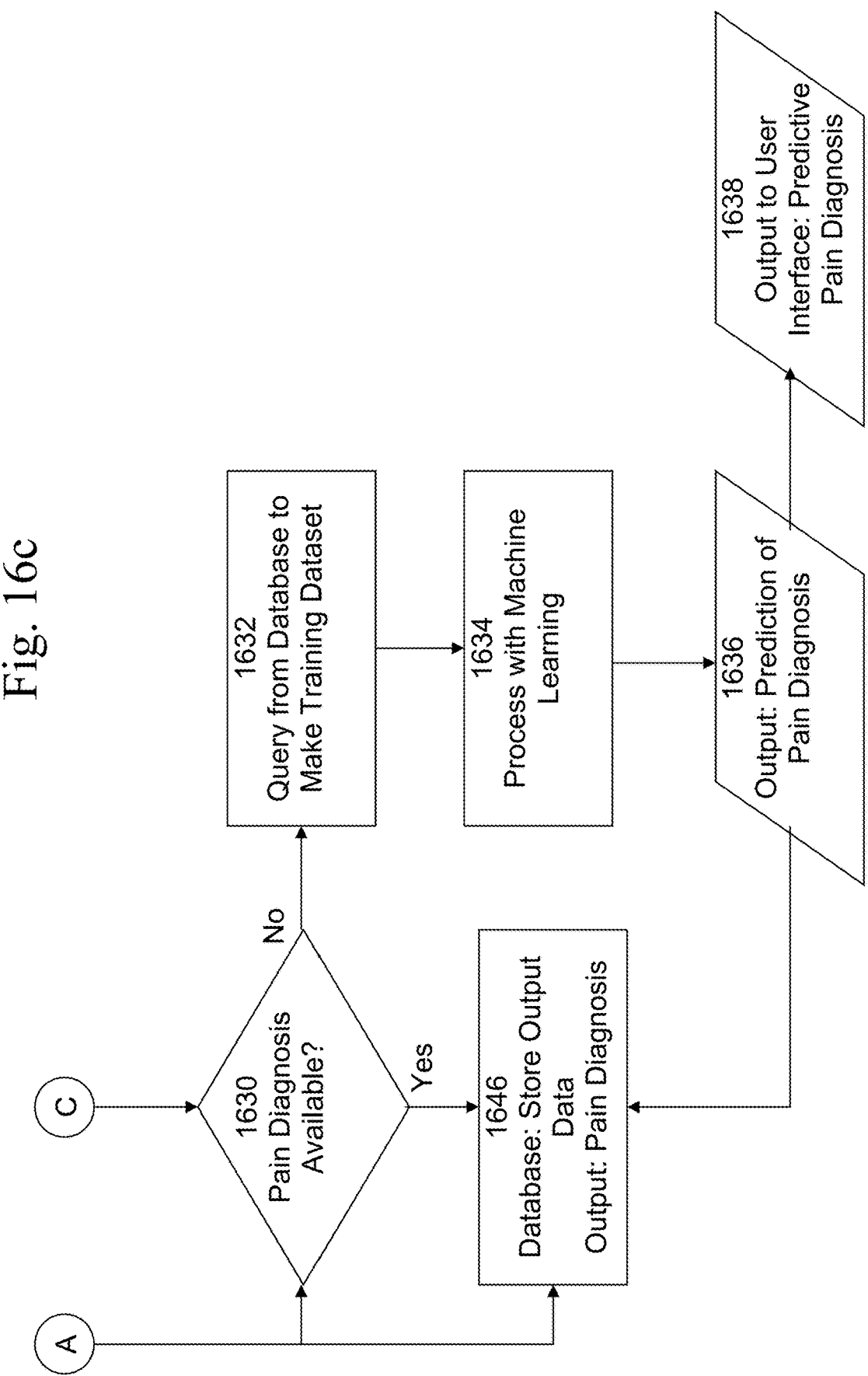

An example of a process 1600 of neural oscillation monitoring is shown in FIGS. 16*a*, 16*b*, and 16*c*. For simplicity, process 1600 is described using the example of a pain diagnosis. However, this is merely an example, as process 1600 is equally applicable any neural oscillation based diagnosis or condition. Process 1600 may be fully automated and may be trained on EEG data from specified groups. Once trained, process 1600 may provide the capability to blindly classify an unknown EEG into groups as defined by the user. The results of the analysis may provide accuracy, sensitivity and specificity of dividing the initial EEG data into cohorts/groups or patterns. The results may be utilized in use-cases such as medical diagnosis, pharmaceutical drug efficacy studies, personalized fitness consumer use, and others.

Process 1600 begins with 1602, shown in FIG. 16*a*, in which input data may be obtained. Data may be input into algorithm in several forms, for example, text files, real-time raw data through software development kits, real-time raw neural oscillations, or EEG data, etc. For example, at 1604, raw EEG data files may be read. As an example, documented Python functions may be used for monitoring systems that use Python scripts. The listed techniques are merely examples; the present invention contemplates data input in any format using any input technique.

At 1606, preprocessing may be performed on the obtained data, such as the raw EEG data. Typically, raw EEG data, which may include EEG data obtained directly from EEG recording equipment, requires pre-processing and cleaning. For example, at 1608, band-pass filtering may be performed. Band-Pass filtering may include frequency filtering the data in order to analyze neural oscillation frequencies of interest. For example, data may be filtered at 4-45 Hz for the complete spectrum (Hipp, et al. 2012) and 8-14 Hz for the broad alpha range (Lundqvist, et al. 2013). At 1610, artifact removal may be performed. After filtering of the data, artifact removal may be performed, for example, using an averaging technique such as a linear (nearest neighbor) approach using weighted averaging. Omitting the data from EEG electrodes with artifacts is not a desirable due to the fact that source localization depends on scalp potential distribution. In the linear method, artifacts may be reconstructed through a weighted average of data from neighboring electrodes. The weights may be proportional to the Euclidean distance between the electrodes. For example, the three nearest neighbors of each electrode may be determined and the recordings of the three nearest electrodes may be averaged.

At 1612, common spatial pattern (CSP) recognition may be performed. CSP may be used for electrode selection, in order to optimize the data analysis by preselecting those EEG electrodes that show the highest variance in their signal, as these are presumed to reflect a brain function/dysfunction pattern. The CSP processing may provide indications of the electrodes that may contain the best features for classification. This approach reduces the computational requirements during further processing, as only the highest-ranking electrodes may be used for further analysis.

At 1614, after CSP processing, segmentation of the data may be performed. A recording may be segmented into short duration intervals, with or without overlapping data points.

Turning now to FIG. 16*b*, the pre-processed data may be analyzed using a variety of different methods. For example, spindle threshold analysis 1616, power spectrum analysis 1618, and wavelet analysis 1620, as well as other techniques, may be used. These processing methods may be used to identify features for the machine learning.

At 1616, spindle threshold analysis in the time domain may be performed. In order to detect pain spindles that may constitute a brain function pattern, a modified spindle amplitude threshold-setting method may be used. In this method, the maximum amplitude in the duration of the recording may be determined using a threshold. Typically, the level of the threshold may be initially set at a maximum value and then may be reduced until the threshold is at zero. For example, the threshold in steps of 10% of the initial amplitude until the threshold of 0 µV is reached. A spindle may be detected when a region of 0.5 seconds of the recording exceeds the current threshold level. At 1622, the detected potential spindles may be output.

At 1618, power spectrum analysis in the frequency domain may be performed. Power decomposition may be performed to determine the power of each frequency that is contained in the recording by using, for example, fast Fourier transforms (FFT) to decompose the recording into frequencies. Several segments of the EEG data may be averaged in order to reduce the variance of the estimate. At 1624, the determined relative power spectra may be output.

At 1620, wavelet analysis in the time-frequency domain may be performed. Wavelet/TFA analysis may be performed executed using, for example, a short time Fourier transform or wavelet transform. Time may be mapped into frequency and phase by the Fourier transform and time may be mapped into scale and time for the wavelet transform. A variety of wavelet analyses may be performed. For example, Morlet wavelet analysis provides wavelets that have a sinusoidal shape weighted by a Gaussian kernel and may capture local oscillatory components in a time-series. At 1626, the determined TFA coefficients may be output.

At 1628 the detected potential spindles, the determined relative power spectra, and the determined TFA coefficients may be combined into a dataset.

Turning now to FIG. 16*c*, at 1630, it may be determined whether or not a pain diagnosis is available in a database (discussed further below) on the basis of the combined dataset. If not, then at 1632, a query may be made from the database to generate a training dataset for machine learning. At 1634, the training dataset may be processing with machine learning. The goal of the machine learning method is to correctly classify with high accuracy, sensitivity, and specificity, an automated and objective method to classify brain function/dysfunction. Features may be selected as spindles, relative power, and wavelet coefficients. Examples of machine learning techniques that may be used include Naïve Bayes, 1 and 2 Nearest Neighbors, and Support Vector Machine (SVM), as well as other machine learning techniques. Features may be selected from signal processing methods such as potential spindles, relative power, TFA or wavelet coefficients, etc. At 1636, a prediction of a pain diagnosis may be output from the machine learning processing. At 1638, the prediction of the pain diagnosis may be output in a human readable form on a user interface or other technique for use by a user, doctor, patient, or other person.

In addition, at 1640, data related to the prediction of the pain diagnosis may be stored in the database. This database may store information such as raw EEG data, pre-processed EEG data, potential spindle data, relative power spectra data, TFA coefficient data, machine learning data, prediction data, etc. Accordingly, at 1642, supplementary data, and, at 1644, pain diagnosis data, may be read from the input obtained data 1602. These data, as well as other data from the database may be used at 1630 to determine whether or not a pain diagnosis is available. As discussed above, if a pain diagnosis is not available, then the dataset may be processed using machine learning. If, at 1630, a pain diagnosis is available, then, at 1646, the relevant data from the dataset may be stored in the database, and the determined pain diagnosis may be output.

A cross validation technique may be used to evaluate the performance of the classification. For example, a 10-fold cross validation approach may be applied to the dataset to determine sensitivity, specificity, and accuracy. The sensitivity of a clinical test refers to the ability of the test to correctly identify those subjects with an EEG pattern of interest or brain state (Lalkhen and McCluskey 2008).

$$\text{Sensitivity} = \frac{\text{True positives}}{\text{True positives} + \text{False negatives}}$$

A test with 100% sensitivity correctly identifies all subjects in a specific brain state. The specificity of a clinical test refers to the ability of the test to correctly identify subjects without the specific brain state (Lalkhen and McCluskey 2008).

$$\text{Specificty} = \frac{\text{True negatives}}{\text{True negatives} + \text{False positives}}$$

A test with 100% specificity correctly identifies all subjects without a specific brain state. The accuracy may be computed by $$\text{Accuracy} = \frac{(\text{True positives} + \text{True negatives})}{(\text{True positives} + \text{True negatives} + \text{False positives} + \text{False negatives})}$$

The accuracy provides a selection criterion upon which the optimal number of electrodes and best performing algorithm could be determined.

The end results of process 1700 may be presented in a variety of ways. One example may be a diagnosis of a brain dysfunction state such as chronic pain or Alzheimer's disease. Another example may be utilizing the real-time accuracy results for applications such as input into personalize fitness-training modules.

Figure 17:
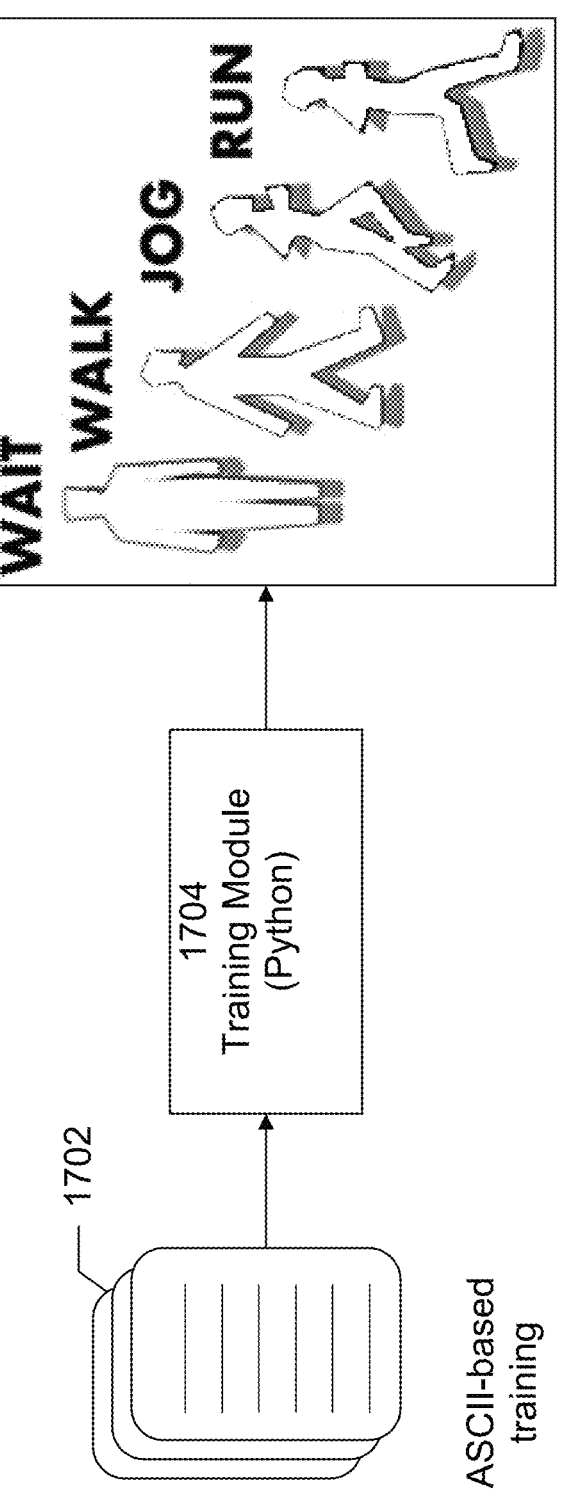
FIG. 17 illustrates an exemplary flow diagram of an application according to an embodiment of the present invention.

An example of the use of neural oscillation monitoring for personalized fitness is shown in FIG. 17. In this example, for each type of exercise or physical activity, EEG data may be collected and compared to non-activity or different modes of activity. For example, EEG data may be collected for running modes: standing, walking, jogging, running. This data may be in any form, but in the example shown in FIG. 17, the data may include ASCII-based training data 1702. The EEG patterns associated with the body's response to these modes may be measured and used to train the neural oscillation monitoring system, for example, using the illustrated Python-based training module 1704. For example, if an exerciser is experiencing high levels of exertion, discomfort, or pain in the jogging mode, this data may then be used to train the monitoring system to learn the level of exertion of the mode 1708. For example, the results of the neural oscillation detection may be represented in the BORG scale for physical exertion. The results of the EEG-BORG scale may then be used to scale an exercise-training module. This may allow the exerciser to personalize their running based on their body's exertion levels. Accordingly, in this example, an exerciser may personalize their training to their body's requirements for an effective workout.

Figure 18:
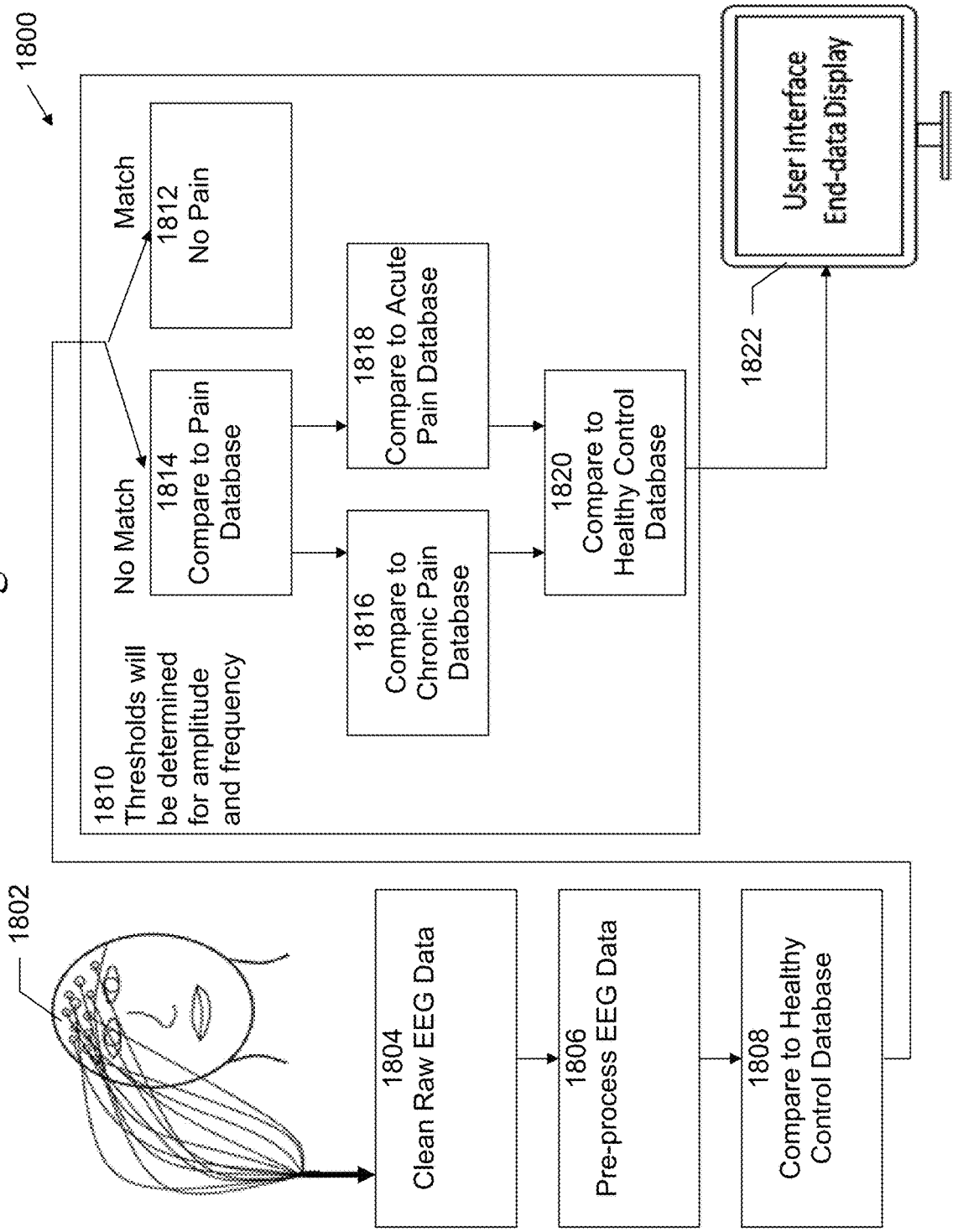
FIG. 18 illustrates an exemplary diagram of an application according to an embodiment of the present invention.

An example of the use of neural oscillation monitoring for pain diagnosis is shown in FIG. 18. Chronic pain is a severe and growing problem in the United States, affecting 116 million Americans and costing $635 billion annually. Pain is especially a significant problem for the military, as a high percentage of soldiers and veterans suffer from both acute and chronic pain. Current pain diagnosis relies on subjective self-reporting of patients making it difficult to quantify pain and its intensity. An objective assay that can rapidly and reliably detects or diagnose pain and its intensity would be useful, and would be especially useful for patients that are unable to self-report such as traumatically injured including the cognitively impaired and sedated patients. An objective pain signature associated specifically with chronic neuropathic pain and its intensity level in patients was recently discussed (Green et al 2009). This pain signature is an increase in (alpha) frequency power with greater spindle activity, which was measured using surgically implanted deep brain electrodes. Using the neural oscillation detection algorithm, used EEG may be used for detection of the scalp correlates of the pain signature to enable its use in portable, user-friendly technology. The detection algorithm could classify pain patients from no-pain with 96% accuracy and high pain from low-pain with 100% accuracy based on patient's EEGs.

As shown in FIG. 18, a system 1800 for neural oscillation monitoring for pain diagnosis may include EEG data sensors 1802, processing and data blocks 1804-320, and display device 1822. EEG data sensors 1802 may be used for gathering raw EEG data from a subject. At processing block 1804, the raw EEG data may be cleaned, as described above. At processing block 1806, the cleaned EEG data may be pre-processed, as described above. At processing block 1808, the cleaned and pre-processed EEG data may be compared to data in a database including corresponding data gathered from healthy control subjects. At processing block 1810, thresholds may be determined for amplitude and frequency. If, at 1808, it was determined that there was a match between the processed EEG data and one or more entries in the healthy control database, then at 1812, it may be determined that the subject does not have pain. If, at 1808, it was determined that there was not a match between the processed EEG data and any entries in the healthy control database, then at 1814, the processed EEG data may be compared to a pain database, including, at 1816, a comparison to a chronic pain database, and at 1818, a comparison to an acute pain database. At 1820, the processed EEG data, along with data relating to matches of the processed EEG data to the pain database, the chronic pain database, and the acute pain database, may be compared to the healthy control database. At 1822, the resulting pain diagnosis may be output or displayed, for example, on a user interfaces.

Figure 19:
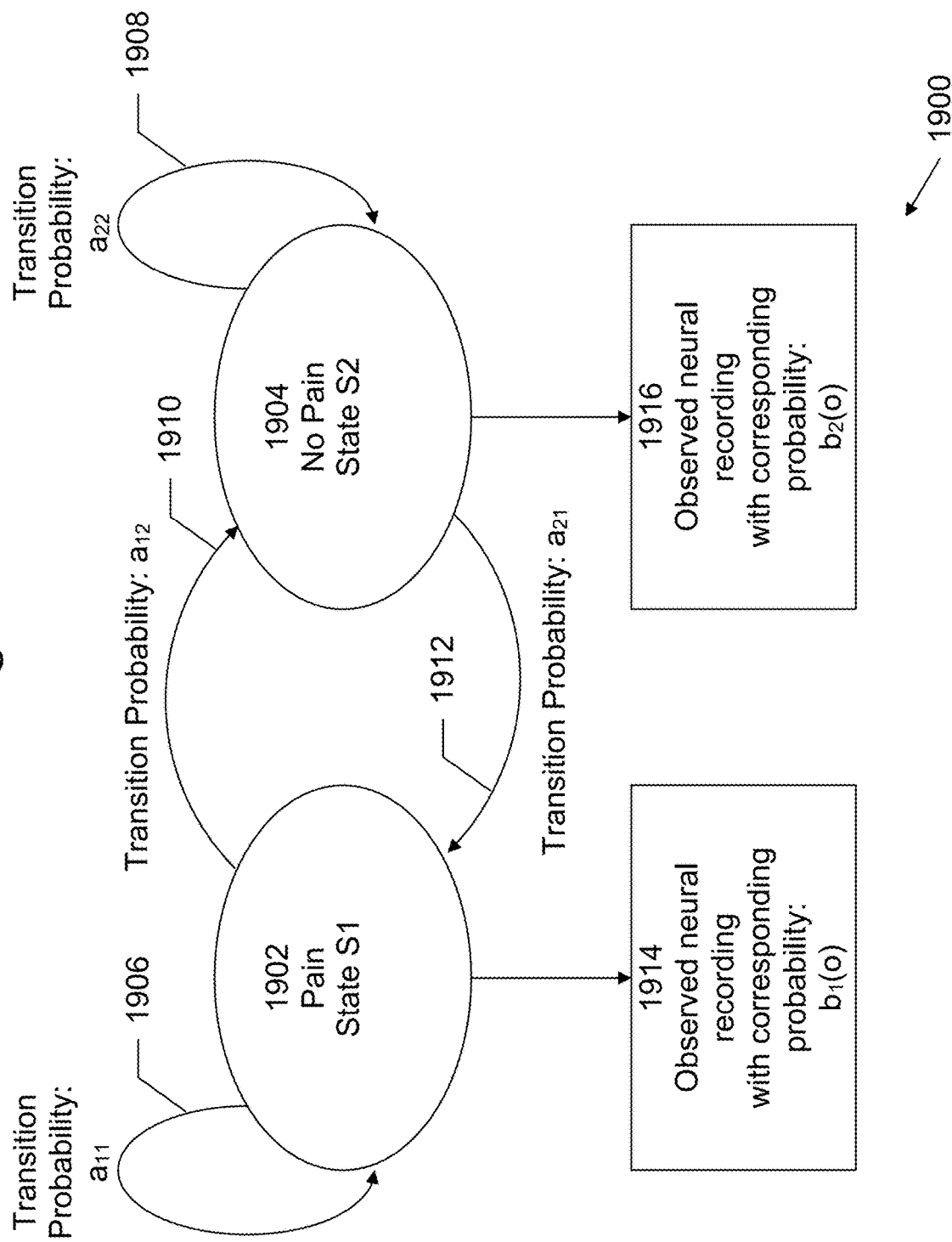
FIG. 19 illustrates an exemplary state diagram of finite state machine processing for an exemplary biomarker pathway that may be performed according to an embodiment of the present invention.

It may be noted that the processing performed at 1806, 1808, 1816, 1818, and 1820 may provide input to, or be considered to be steps in finite state machine (FSM) processing. A state diagram 1900 of such finite state machine processing for an exemplary biomarker pathway is shown in FIG. 19. As shown in this example, there are two states Pain State S1 1902 and No Pain State S2 1904. The probability of transition from S1 to S1 is $a_{11}$ 1906, the probability of transition from S2 to S2 is $a_{22}$ 1908, the probability of transition from S1 to S2 is $a_{12}$ 1910, and the probability of transition from S2 to S1 is $a_{21}$ 1912. The output 1914 from S1 is an observed neural recording with corresponding probability: $b_1(o)$, and output 1916 from S2 is an observed neural recording with corresponding probability: $b_2(o)$.

Figure 20:
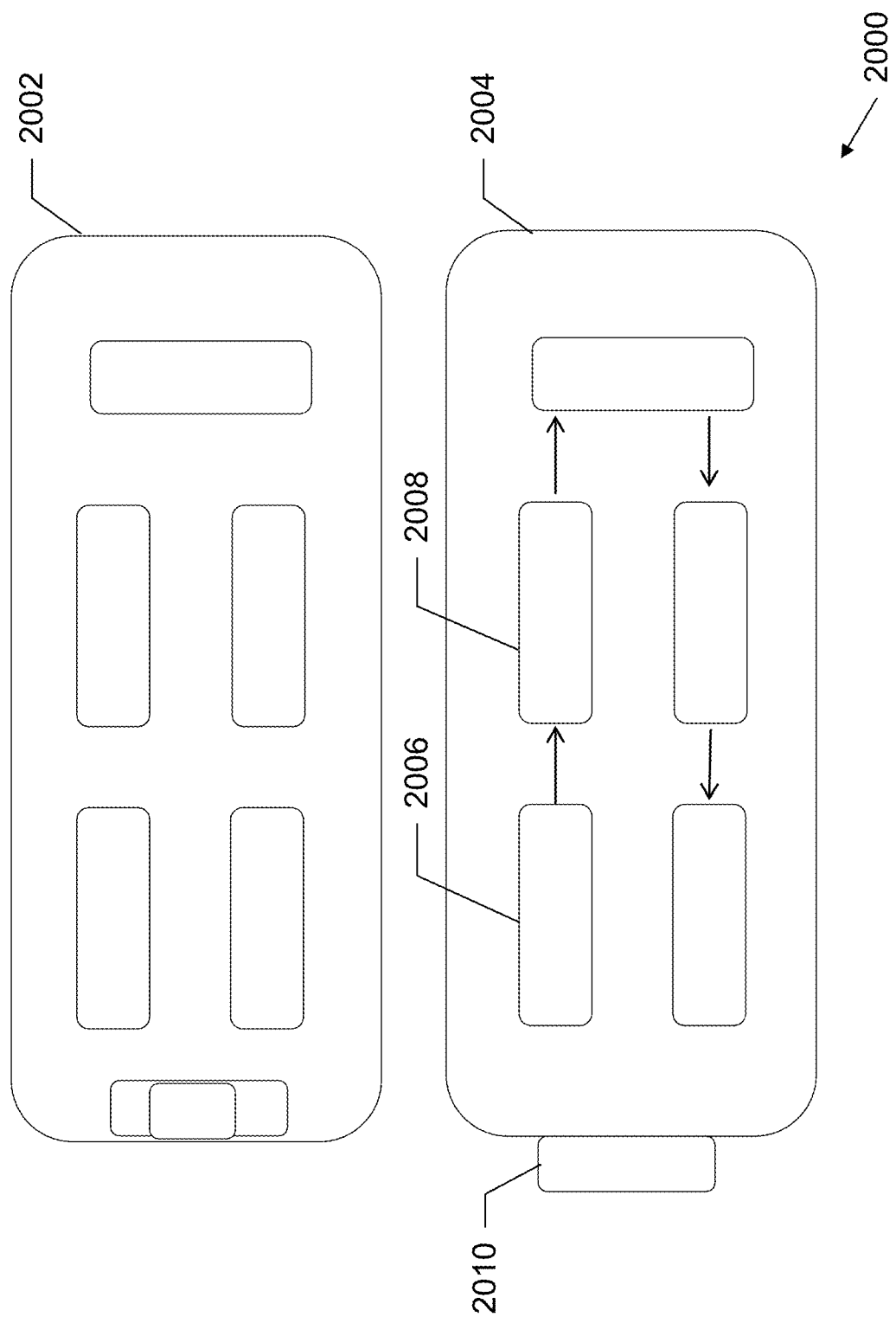
FIG. 20 illustrates an exemplary block diagram of a portable neural oscillation detection system.

An example of a portable neural oscillation detection system 2100 is shown in FIG. 20. In this example, a smartphone or other portable or mobile computing device may be utilized as the basis for system 2100. For example, a user interface 2102, such as a diagnosis and treatment user interface, may be displayed, typically on the front of device 2100. User interface 2102 may provide the capability to receive input from a user and to display diagnosis and treatment information to the user. On the back 2104 of the device, there may be a number of sensor nodes attached to device 2100. For example, there may be one or more EEG sensor nodes 2106 or electrodes, for detecting EEG signals, as well as one or more transcranial direct-current stimulation (tDCS) nodes 2108 or electrodes for providing neurostimulation signals. Further, software 2110 to implement the user interface, processing, and signal generation functionality may be provided. Accordingly, this example may be utilized for neural oscillation biomarker detection of pain and provision of tDCS or USN pain treatment signals.

Figure 21:
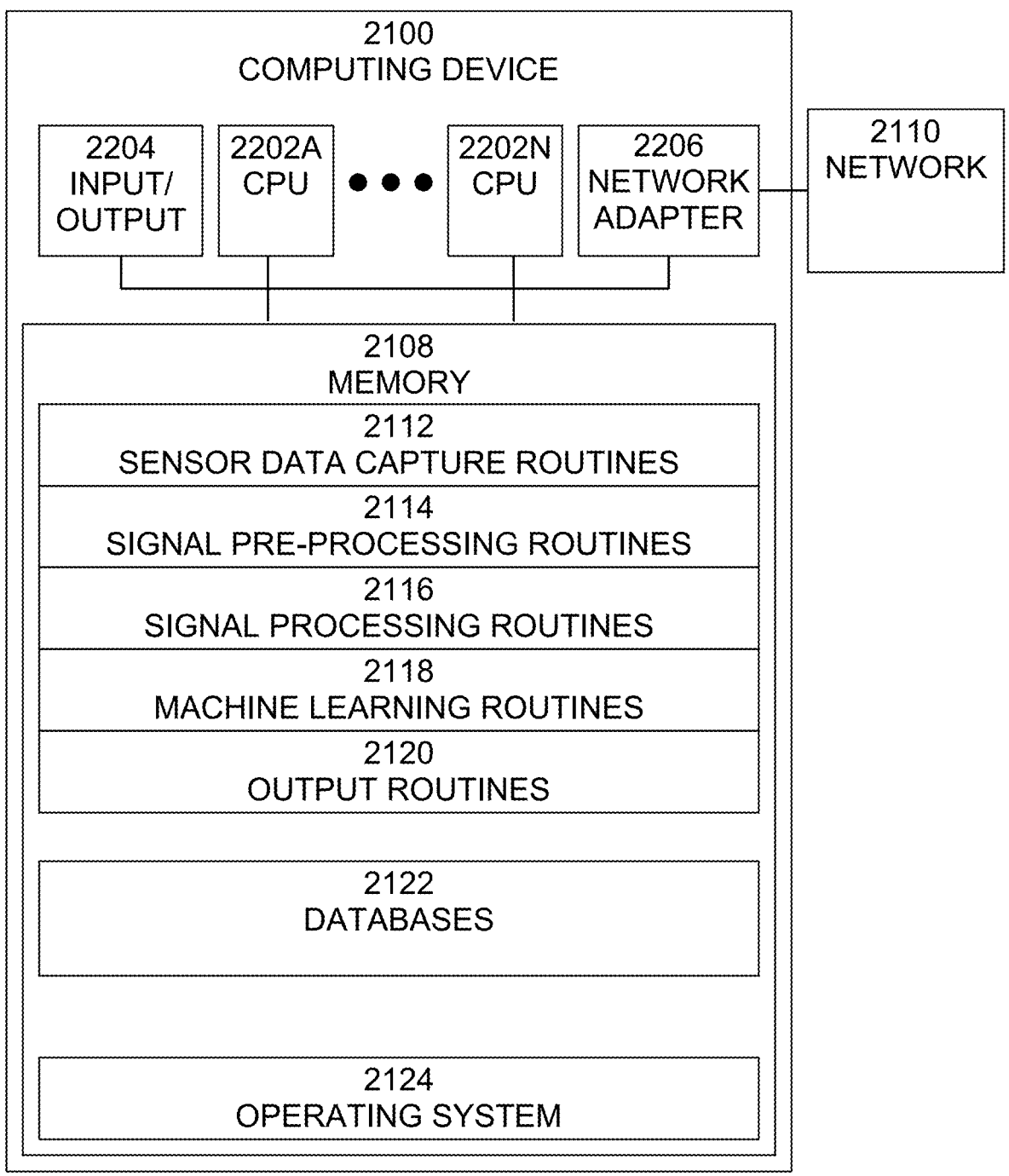
FIG. 21 illustrates an exemplary block diagram of a computing device in which processes involved in the embodiments described herein may be implemented.

An exemplary block diagram of a computing device 2100, in which processes involved in the embodiments described herein may be implemented, is shown in FIG. 21. Computing device 2100 may be a programmed general-purpose computer system, such as an embedded processor, system on a chip, smartphone, tablet, or other mobile computing device, personal computer, workstation, server system, and minicomputer or mainframe computer. Computing device 2100 may include one or more processors (CPUs) 2102A-2102N, input/output circuitry 2104, network adapter 2106, and memory 2108. CPUs 2102A-2102N execute program instructions in order to carry out the functions of the present invention. Typically, CPUs 2102A-2102N are one or more microprocessors, such as an INTEL PENTIUM® processor. FIG. 21 illustrates an embodiment in which computing device 2100 is implemented as a single multi-processor computer system, in which multiple processors 2102A-2102N share system resources, such as memory 2108, input/output circuitry 2104, and network adapter 2106. However, the present invention also contemplates embodiments in which computing device 2100 is implemented as a plurality of networked computer systems, which may be single-processor computer systems, multi-processor computer systems, or a mix thereof.

Input/output circuitry 2104 provides the capability to input data to, or output data from, computing device 2100. For example, input/output circuitry may include input devices, such as keyboards, mice, touchpads, trackballs, scanners, etc., output devices, such as video adapters, monitors, printers, etc., and input/output devices, such as, modems, etc. Network adapter 2106 interfaces device 2100 with a network 2110. Network 2110 may be any public or proprietary LAN or WAN, including, but not limited to the Internet.

Memory 2108 stores program instructions that are executed by, and data that are used and processed by, CPU 2102 to perform the functions of computing device 2100. Memory 2108 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 2108 may vary depending upon the function that computing device 2100 is programmed to perform. For example, as shown in FIG. 1, computing devices may perform a variety of roles in the system, method, and computer program product described herein. For example, computing devices may perform one or more roles as end devices, gateways/base stations, application provider servers, and network servers. In the example shown in FIG. 21, exemplary memory contents are shown representing routines and data for all of these roles. However, one of skill in the art would recognize that these routines, along with the memory contents related to those routines, may not typically be included on one system or device, but rather are typically distributed among a plurality of systems or devices, based on well-known engineering considerations. The present invention contemplates any and all such arrangements.

In the example shown in FIG. 21, memory 2108 may include sensor data capture routines 2112, signal pre-processing routines 2114, signal processing routines 2116, machine learning routines 2118, output routines 2120, databases 2122, and operating system 2124. For example, sensor data capture routines 2112 may include routines that interact with one or more sensors, such as EEG sensors, and acquire data from the sensors for processing. Signal pre-processing routines 2114 may include routines to pre-process the received signal data, such as by performing band-pass filtering, artifact removal, finding common spatial patterns, segmentation, etc. Signal processing routines 2116 may include routines to process the pre-processed signal data, such as by performing time domain processing, such as spindle threshold processing, frequency domain processing, such as power spectrum processing, and time-frequency domain processing, such as wavelet analysis, etc. Machine learning routines 2118 may include routines to perform machine learning processing on the processed signal data. Databases 2122 may include databases that may be used by the processing routines. Operating system 2124 provides overall system functionality.

As shown in FIG. 21, the present invention contemplates implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multitasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

Gero (1990) proposes a multifaceted model of knowledge in his approach to interface representation design. In particular, his conception of relational knowledge is similar to that of Wang. Here he argues that variables such as function, structure, and behavior, while important in themselves, are largely interdependent, and it is the relationships of interdependency that form the bulk of useful relational knowledge. Qualitative knowledge provides information on the hypothetical alteration of the interdependent variables of function, structure, and behavior. In particular, this type of knowledge informs the decision-making process by calling upon prior experience to compensate for uncertainty. Computational knowledge symbolizes mathematical relationships between key variables, and constraints include knowledge of certain actions that will affect the range of possible outcomes. Finally, context knowledge relates to external variables (characteristics of the environment, etc. that could affect the outcome in question). What is particularly significant about Gero's approach is his perceived need to assign different qualities to different types of knowledge; it is as if at a unit level, these types he describes have little in common, and all are needed for coherent cognition to take place. To this end, one might view each 'type' of knowledge he describes as a basic unit of thought, as A, T, C, and G are fundamentally distinct but interdependent units of the DNA molecule.

Block (1962) describes the "perceptron," or a series of sensory and associator units connected to resemble sensory and analytical components into a machine that vaguely models human response to sensory stimuli. Stimuli of a certain threshold trigger activity in specific associator units, which then activate those to which they are directly connected. Thus, different types of stimuli activate different networks of associator components. In this sense, Block's perceptron approach to modeling brain function is similar to our own in that it privileges the connections between components rather than the components themselves as the primarily important in decoding human thought. However, there still remains the question of what constitutes a basic unit of connectivity. Does a single connection between two associates constitute a fundamental unit of perceptron "thought?" Studying the structure and function of different types of neural connections promises significant contributions, but this still begs the question of whether these connections consist, at some level, of units that are part of the same small set.

Anderson et al. (1998) developed the ACT (adaptive control of thought) in 1976 and it is a computational/mathematical model of cognition. This theory has multiple modules: The perceptual-motor modules, the goal module, and the declarative memory module. Like the perceptron, this paper views cognition as consisting of several distinct subtypes that are not necessarily composed of the same units.

De Waal et al. (2010) perform research that supports the idea of cognitive continuity between human and non-human primates. According to them, mental capacities are based on a 'deep homology' of 'the basic building blocks of cognition' (such as homologous brain regions in birds and mammals). Instead of asking which species can perform at a specific cognitive level, they suggest that a better question to ask is what is necessary for that level of cognition to take place and how it works. They suggest that mental capacities have to be broken down to neural level. They use mirror neurons as a bottom up approach to explain fundamental units for motor tasks, memory, future planning, pro-social behavior, and imitation. This theory is more biological as opposed to the mathematical theory that comprises the Unitary System and the FCU, since it accepts neurons rather than arrangements of cognitive structures as a fundamental unit of thought. However, the two approaches are similar in that they both proceed upward after defining a fundamental unit.

Aerts (2009) discusses the cognition of concept formation and communication of meaning. They show that it is governed by the presence of quantum structure in cognition. They show that they can derive structure of human thought by interpreting quantum representation in a model that centers on 'emergence due to superposition', 'interference,' and 'specific quantum field theoretic aspects'. According to them human thought comprises two layers, the 'classical logical layer' and the 'quantum conceptual layer'. This model is not as concerned with pure linguistic structure. Rather it focuses on the 'meaning aspects' of concepts and their combinations. This has significant consequences for the traditional problem of artificial intelligence, and the idea that meaning must be ascribed to the computational prerequisites of intelligence.

Lamb (2010) introduces the concept of the functional web, in which he posits that cognitive concepts such as single words and ideas (analogous to semantic primitives) are in fact spatially distributed across parts of the brain such as the cerebral cortex. Lamb splits these concepts into conceptual, motor, phonological image, tactile, and visual components, or components that roughly align with the senses. This approach not only applies to cognition but also to the concepts that comprise it is intuitive since its criteria are empirically grounded. In addition, it unifies behavioral and linguistic with neurological activity.

What the FCU seeks to do in addition is to tie cognition not just to specific sensory activity but also to brain activity in itself; Lamb's approach is more focused on response and activation, but the nature of cognition is such that thought can beget more thought; an external agent is not consistently necessary.

Blais et Al. (2011) argue that modeling cognitive activity based on synaptic modification depends in large part on how synapses are stabilized after firing. With respect to synaptic activity, there are numerous types of "learning," each of which has a different neuronal effect. Hebbian learning, for instance, occurs when the connectivity between two neurons decreases after one produces an action potential in the other. It is represented in a matrix as such:

$$\frac{dm_i}{dt} = \phi(c)d_i$$

The selectivity-learning rule, on the other hand, incorporates a variable threshold of activation because it modulates the type and level of response to sensory stimuli (for instance, the difference between looking at the sun or at the night sky).

$$\frac{dm}{dt} = c_k(c_k - \theta_M)d_k$$

Blais et al. demonstrate an important mathematical connection between biology and temporality, or the idea that modeling such processes as cognition involves the accounting for change rather than for absolute physical values. In this way, Blais does for synaptic selectivity what we do with cognition as a whole, and in doing so demonstrates the process parallelism that pervades natural phenomena. The unitary logic-based FCU is a more generalized form of Blais's analytical approach; that is, it does not exclusively deal with stimuli.

Penrose (1991) suggests that consciousness is not just complex computation, but instead quantum computing of objective reduction, a self-collapse of the quantum wave function as a result of quantum gravity. He links the mind to space-time geometry. However, Penrose never specified the anatomical location of the seat of consciousness in the brain. Hameroff suggests that microtubules in neurons are the seat of consciousness and perform quantum computing. Microtubules have proteins that associate with their quantum conformation states and thus orchestrate their actions. Thus Hameroff calls the quantum states orchestrated objective reductions. According to Hameroflmicrotubule units can undergo quantum coherence across large areas of the brain. The quantum states of microtubules are maintained without environmental entanglement for up to 500 ms. Microtubule units are able to interact with neighboring units. Conformational changes in microtubules can regulate synapses and other neuronal activities. This mode is related to unconscious activity. Quantum coherence among microtubule units occurs through electrons in hydrophobic pockets acting as a quantum computer. The associated proteins communicate the quantum state to the environment and hence collapse microtubules, resulting in what is known as orchestrated objective reduction. The selection of quantum states is random. Orchestrated objective reduction binds different microtubule unit conformations over large areas and at different time scales into a conscious though.

In a general sense, Orchestrated Objective Reduction is a form of the popular collapse of the wave function theory that asserts that the quantum state activity in the microtubules is sufficient to influence synaptic transmission; thus, it represents a form of active conscious control of mental function. This idea has been criticized because the calculated quantum decoherence happens within a time frame that would not be biologically significant. Other theories have responded by bolstering support for Orchestrated Organic Reduction by factoring in quantum correction.

Taking Orchestrated Objective Reduction as a template, results of a testable theorem are then needed. For instance, there are many clues that indicate that conscious processes are necessarily supported by a distributed network of synchronous neuronal firings. According to the endogenous EMF, conscious electromagnetic information field (CEMI) theory, quantum brain dynamics (QBD) theory, among others, the synchrony of the action potential firing creates a local electrical field that is the substratum for consciousness. Cortical gamma oscillation, as well as the observed effects of deep brain stimulation, TMS, and other electromagnetic manipulations support the notion that the brain does produce an EM field that can interact with other fields that influence brain function indirectly. While each of these theories contributes to our understanding of the complexity of consciousness, none of them can explain the phenomenological experience of agency, or the qualitative distinction that marks the conceptual gap between the human brain and the human mind. Intention Awareness is a subfield that approaches this problem more directly and with recent research has led us to believe that, based on quantum spin-theories of consciousness, we may need to search for an unprecedented form of matter interaction due to the dearth of theories that can be used to explain cognition. Prior to such a search, however, the problem of cognition must be approached more directly. Intention Awareness is a similar concept to situational awareness in that it incorporates factors of an actor's environment, but it takes a further analytical step by defining those factors temporally and causally. Thus, to be "intention aware" means to weave present events and intelligence into a causal network of past and future intentions and action.

Similarities between the Unitary/FCU approach and quantum coherence lies in consciousness governed by quantum effects. Hameroff describes microtubules in a minimum of states of conformation that trigger consciousness like GC describes 3, 5 and +/−. However the advantage the unitary system has over Hameroff in this is that it works at both quantum and cognitive level and explains quantum information propagation. Also, Hameroff states that quantum collapse occurs on a scale of 500 ms, which is not biologically possible, whereas cognition modeled under the unitary system is defined by different time scales. In addition, the unitary system is not spatially limited or level-of-cognition limited as Hameroff's microtubules are.

Contemporary conceptualizations of cognition often focus on cognitive structures and its overall character, but examinations of its physical nature at the unit level are equally important. Baslow (2009) frames his argument as a study of how receptors receive and transmit information. This is because, as he argues, there are two leading schools of thought regarding neuronal communication that are both difficult to verify empirically. The first, the "spike timing code" theory, suggests that specific information is carried not only in the average firing rate of a neuron, but also in the precise timings between each spike. Alternatively, the "spike rate code" theory, posits, "information is coded by the mean firing rate of the neuron, and that spike timing is naturally random. Instead of engaging critically with these theories directly, Baslow explores the implications of both of them for the theory that language persists even at the interneuron level. Baslow calls the sending language a "two letter alphabet consisting of spikes and pauses between spikes that form specific meaningful reproducible "words" that can be used to transmit information obtained from a variety of external and internal sensors." The main advantage of applying language at this level, Baslow argues, is its universality:

"The universal nature of neuronal S/P languages is clear in that they can be written in many different frequency-encoded formats, and can be translated into any number of spoken or symbolic human languages, all with the same meaning. Neurons are also highly specialized communicating cells that use both electrophysiology, and what appears to be a more primitive chemical communication mechanism between neurons at chemical synapses. Thus, it follows that inter-cellular chemical communication that is used by a variety of modern cells as well as neurons is an ancient trait, and that all cells are probably biosemiotic systems."

Baslow further develops the neuron as a sem1ot1c object, or one capable of transmitting meaning, based on spike action potentials. Each neuron uses a simple signaling mechanism for communicating with neighbors: that electro-physiological action potential spike, which lasts about 1 millisecond, along with pauses. "Phrases" are repeated groups of spikes and pauses that compose words. Based on the S/P language he develops for interneuron communication, Baslow concludes that the basic "unit" of cognition in the brain is a dyad of connected neurons and their dendrites and synapses. Two important pieces of evidence underlie Baslow's claim. First, regardless of how information is communicated across synapses (rate or timing), it is clear that the spikes and pauses are its medium. Second, since a dyad of neurons is the smallest group across which the SIP language can be used, it must be by definition the fundamental unit of cognition.

For Baslow, there are four potential means by which neuron dyads can modulate signals sent: the length or thickness of the dendrites, and the length or width of the synaptic cleft. However, any change in the dendritic field can bring about a change in meaning of the words and phrases transmitted as spikes and pulses. Thus, Baslow argues that word-based translation takes place at the neuron level, and that words that are transmitted from one neuron to another are physically translated into a new spike/pulse language before they are interpreted by the receiving neuron.

This activity of translation allows for the recall of memory engrams encoding specific sensory recollections: this is because the act of recalling and the memory recollected will occur in different spike/pulse languages, but the meaning of the former will be preserved in the retrieval of the latter. In addition, Baslow asserts that anomalies in this translation process are the mechanisms of pathological and drug-induced changes in brain activity.

The binary basis for interneuron communication Baslow puts forth lends credence to the unitary system as a useful formula for decoding cognitive activity mathematically. However, his application of a broad definition of language (one that encapsulates both signaling between neurons and speech between humans) leads to a conclusion that is divergent with our own; namely, that the basic unit of thought must be defined in terms of biological structures that compose the brain.

Many of these approaches to cognition appear to assert the need for a conceptual breakdown of cognition in order to better model it. That is, each expression, whether linguistic or otherwise, reflects some contextual information, prior knowledge, and a rational schema based on qualitative and quantitative analysis. Since we posit the notion that each type of knowledge or form of thought could originate from the same fundamental cognitive units (or, to use a computer science analogy, data structures), it is important to address these positions. We do not believe that we are inherently incompatible with them; rather, their models simply don't have a low enough level of analysis to acknowledge the possibility that the diverse types and numbers of knowledge and processing they propose are, at a basic level, woven from the same cognitive fabric.

To understand how the brain achieves these objectives on a consistent basis requires investigation of the problem at several levels simultaneously: from electro-physiology to molecular mechanisms of information storage and signaling, to neural network foundation and trends. From a code and process to automata of sensory information, from the functional processes of perception, recognition, and behavioral control that must be implemented by the brain to the language expressed by higher intelligence and adaptation.

The role of linguistics in deciphering cognition: We posit that the linguistic base that humans possess is rooted in the same natural language and shared regardless of the language each of us speaks. While some of any natural language has been evolved over time to include sophisticated semantics, there is a series of core grammatical and lexical concepts that have remained the same over time. These are linguistic 'primes,' which exist both at the word and sub-word level. In the latter case, there is a demonstrable analytical bias towards specific letter and phoneme types among francophone and other western language speakers. Specifically, one study has found that "French and Italian adults were found to be able to track transitional probabilities at the lexical level in a context of fixed consonants and variable vowels, but not the other way around." New et Al. (2008) concluded, "The scope of the consonantal bias at the lexical level is not even limited to the speech modality. It actually extends to lexical access through reading." While this does not suggest that cognition is coded at the phoneme level, it does lend credence to the notion that, like biochemical reactions, cognition is composed of a few basic building blocks that can be arranged into any number of small concepts or words, which can in turn be combined into any of a rich set of thought expressions.

At the grammatical level are embedded semantic primes, a concept similar to the prime in the natural numbers (2, 3, 5, 7, 11, and so forth). Semantic primes, like prime numbers, are unique and cannot be constructed with other concepts; in this sense, they are truly atomic. By studying the low-level, indivisible conceptual constructs of languages, we can better understand these thoughts and perceptions. In addition, specifying a cognitive prime that plays a similar role in thought that the semantic prime does in language will better elucidate the connection between the two.

Semantic primitives, or innate concepts developed in the htm1an mind and encoded in spoken language without explicit definition, provide a very basic inte1face between the human mind and its physical surroundings upon which cognition builds throughout one's lifetime. They are an intuitive point of departure for analyzing the links between thought and language. Consequently, linking them to other cognitive concepts such as conception, perception, and intention, it is possible to give semantic primes greater context and understand them better. By "marrying" data on semantic primitives to time-based, intrinsic, consequent and contextual value analysis, we argue that it is possible to better understand human cognitive processes and causes of behavior. The existence of semantic primes suggests that we have as part of our inherited human faculties a basic set of innate 'concepts' like intention awareness, or perhaps more precisely, a non-conscious propensity and eagerness to acquire those concepts and encode them in sound-forms (words) intentions. The words that those concepts become encoded in are called semantic primes, or alternatively, semantic primitives—'semantic' because linguists have assigned that word in reference to the meaning of words. Words that qualify as semantic primes need no definition in terms of other words. In that sense, they remain indefinable. We know their meaning without having to define them. They allow us to construct other words defined by them.

As modern human beings who share the same set of types of inherited determinants that make us human (i.e., the human genome), all our natural languages, despite the diversity of language families, share the same basic set of innate concepts, or share the same propensity and eagerness to encode the same set of concepts in words. Our common grandmother and grandfather many generations removed may have encoded those concepts in a specific vocabulary, and therefore had an original set of semantic primes. The dispersal of their descendants from their African homeland throughout the world enabled the evolution of many different languages, each with a unique set of sound-forms for their words. Nevertheless, the same set of semantic primes remained within each language, though expressed in differing sound-forms. Thus, all modern humans have the same set of semantic primes, though not the same set of sound-forms (words) expressing them, rendering semantic primes cross-culturally universal.

The biophysics of cognition: The living neuron transmits infom1ation by "firing" it, delivering only an action potential. The inside of a resting neuron has a negative charge with respect to the outside. Sodium ions are actively pumped out of the neuron and potassium ions are pumped in. Potassitm1 ions flow slowly across the membrane of the neuron, but sodium ions rarely cross it while the membrane is at rest. When the membrane is at rest, the electrical gradient and concentration gradient act in competing directions for potassium, almost balancing out. Both gradients tend to push sodium out of the cell. When the charge across the membrane is reduced, sodium ions can flow more freely across the membrane. When the membrane potential reaches the threshold of the neuron, sodium ions enter explosively, suddenly reducing and reversing the charge across the membrane. This event results in the action potential. For any stimulus greater than the threshold, the amplitude and velocity of the action potential are independent of the size of the stimulus that initiated it.

After the peak of the action potential, the membrane returns to its original level of polarization because of the outflow of potassium ions. Depolarization of the membrane opens voltage-gated sodium and potassium channels and the sodium channels snap shut at the peak of the action potential.

A neuron adds and subtracts excitatory and inhibitory inputs until it reaches a threshold, at which point it fires a single impulse or action potential. At the neuromuscular junction, vi1tually every action potential in the presynaptic motor neuron triggers an end plate potential in the postsynaptic muscle cell. However, the situation at synapses between neurons is more complex because the postsynaptic neuron commonly receives signal from many presynaptic neurons. A single neuron can be affected simultaneously by signals received at multiple excitatory and inhibitory synapses. Just as the brain constantly integrates the unary "plus" and "minus" of words when generating linguistic expression, so too does the neuron continuously integrate these signals and determine whether or not to generate an action potential based on the unitary system.

Generally speaking, atoms such as hydrogen, nitrogen, and oxygen, each have a unique marker that defines its behavior and its interactions with other atoms. This arises from protons, neutron, and electron counts and configuration and, more importantly, the ionization energy as defined by an atom's valence. The ionization that takes place at the valence shell yields energy. If two atoms react and approach one another, it is their outer shells that become involved in any chemical reactions, such as the synaptic exchange. Thus, the ionization energy related to synaptic exchange is driven by the interactions amongst neuronal molecules.

Shifting concentrations of elements within the brain, particularly the activity of the ions, creates an ebb and flow of charge and energy between individual neurons. The flow of electron and protons as action potentials throughout the brain matter gives rise to an energetic field that we call consciousness, which manifests in language as we have previously seen. Thus, the Unitary System is applicable in modeling the changes in this field, which result from the output of chemical transactions between neurons. In particular, neuronal action potentials that drive synaptic communication are themselves driven by a rush of sodium ions into the receiving cell, a process that has a depolarizing effect on the membrane potential. Recovery, on the other hand, is affected by a rush of potassium ions through potassium channels. Both of these effect what is known as the membrane potential of the receiving neuron. Membrane potential in a cell derives from two factors: electrical force and diffusion. Similarly, these are the two primary mechanisms of neuron communication. In the former case, the net actions of ion channels and ion pumps (such as the soditm1-potassium ATPase) embedded in the membrane produce differences (and therefore electrical charge) on the intracellular and extracellular sides of the membrane.

From the viewpoint of biophysics, the resting membrane potential is merely the membrane potential that results from the membrane permeability that predominates when the cell is resting. At any given moment, there are two factors for an ion that determine how much influence that ion will have over the membrane potential of a cell. The first is the ion's driving force, which is the net electrical force available to move that ion across the membrane. It is calculated as the difference between the voltage that the ion "wants" to be at (its equilibrium potential) and the actual membrane potential $E_m$. So formally, the driving force for an ion is equivalent to $E_m - E_{ion}$. For example, if there is a resting potential of −73 mV, the driving force on potassium is 7 mV: (−73 mV)−(−80 mV)=7 mV. The driving force on sodium would be (−73 mV)−(60 mV)=−133 mV. Second is the ion's permeability, which is simply a measure of how easily an ion can cross the membrane. It is normally measured as the (electrical) conductance and the unit, Siemens, corresponds to 1 C·s−1·V−1 that is one charge per second per volt of potential. If the driving force is high, then the ion is diffusing in one direction faster than the other. If the permeability is high, it will be easier for the ion to diffuse across the membrane. Thus, in a resting membrane, while the driving force for potassium is low, its permeability is very high. Sodium has a high driving force, but almost no resting permeability. In this case, potassium carries about 20 times more current than sodium, and thus has 20 times more influence over Em than does sodium.

The effect of increasing the permeability for a particular type of ion is to shift the membrane potential toward the reversal potential for that ion. Thus, opening soditm1 channels pulls the membrane potential toward the sodium reversal potential, usually around +100 mV. Opening potassium channels pulls the membrane potential toward about −90 mV; opening chloride channels pulls it toward about −70 mV. Because −90 to +100 mV is the full operating range of membrane potential, the effect is that sodium channels always pull the membrane potential up, potassium channels pull it down, and chloride channels pull it toward the resting potential.

At the peak of the action potential, on the other hand, permeability to Na is high and K permeability is relatively low. Thus, the membrane moves to near E(Na) and far from E(K). From this example, it becomes clear that the more ions are permeable, the more complicated it becomes to predict the membrane potential. However, this can be done using the Goldman-Hodgkin-Katz equation or the weighted means equation. By simply using the concentration gradients and the permeabilities of the ions at any instant in time, one can determine the membrane potential at that moment. What the Goldman-Hodgkin-Katz equations tell us is that at any time, the value of the membrane potential will be a weighted average of the equilibrium potentials of all permeating ions. The "weighting" is the ions relative permeability across the membrane.

In neurons, the factors that influence the membrane potential are diverse. They include numerous types of ion channels, some that are chemically gated, and some that are voltage-gated. Because voltage-gated ion channels are controlled by the membrane potential, while the membrane potential itself is partly controlled by these same ion channels, feedback loops arise which allow for complex temporal dynamics, including oscillations and regenerative events such as action potentials. Each of these variables can modulate the polarity that results from each chemical transaction and thus drives synaptic communication.

Figure 22:
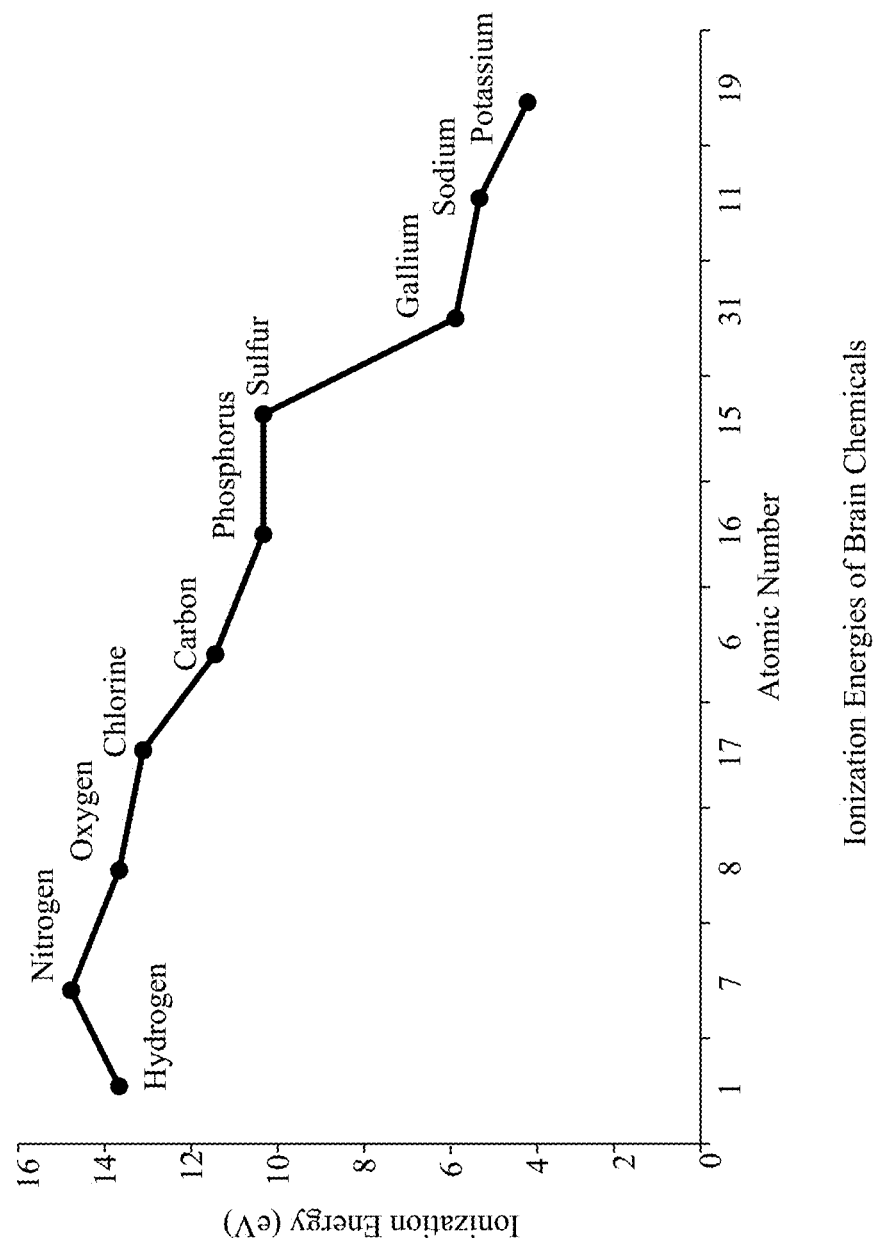
FIG. 22 illustrates examples of ionization energies of some brain chemicals.

Examples of ionization energies of some brain chemicals are shown in FIG. 22.

The model for two populations of neurons to address connections to neighboring networks of actions, or neuron coltm1n, assumes a constant production efficiency, meaning potentiation, or activation ratios. This efficiency also holds at (−10 mv) with (+) displacement and a (−20) with (−) displacement as in the classical Lotka-Volterra equations, which succinctly utilize the energy flow principle: in essence, we are energy processors.

$$\frac{dx}{dt} = -bx - f(x)y$$
$$\frac{dy}{dt} = -ef(x)y - dy$$

Here the system is divided into two levels, (x and y are their respective densities or biomasses in the same units) and the yield constant or the production efficiency (e), manifests the second law of thermodynamics (0≤−e<1). Since e is a constant and the functional response of 1a, f (x), is a monotone non-decreasing function, it follows that higher density never decreases the flow of energy to the next level In fact, all relationships are considered as a (+, −) type, as indicated by the signs of the off-diagonal terms in the community matrix or Jacobian of system (1).

At a synapse, a neuron releases neurotransmitters that excite or inhibit another cell or alter its response to other input. Excitat01y neurotransmitters, the most common type, increase firing rate. An inhibitory neurotransmitter decreases the chances of the neuron firing. Each neuron is influenced via multiple neurotransmitters acting at multiple synapses by dozens of other neurons.

Following the release of a neurotransmitter and the subsequent activation of a receptor, it is important that the response is terminated and the system reset so that a subsequent activation can occur. This is achieved through the removal of the neurotransmitter by metabolic enzyme activity and by passive or active uptake activities. The concentration of the transmitter at the synapse for a longer time period occurs if the uptake mechanism is blocked. Therefore, a neurotransmitter uptake blocker may have an effect similar to a postsynaptic agonist of that transmitter. For uptake to take place, the neurotransmitter must be recognized by an uptake mechanism. As a result, it is common for structural analogs of the neurotransmitter of this process, for example, noradrenaline, serotonin, and dopamine. Here, we see the unitary system at work in the form of chirality.

Biological molecules such as neurotransmitters exist in minor image isomers of one another, and this is what governs the ligand-substrate interaction specificity necessary for biochemical reactions. The recognition of a neurotransmitter by its complementary receptor occurs due to the unique conformation of each isomer-enantiomer ligand, functioning as a "lock and key" mechanism. The two mirror image isomer-enantiomer molecules will interact with postsynaptic receptors, producing different biochemical effects. The ligand-substrate specificity required for neurotransmitter activity is conferred by the unique electronic interactions between asymmetric molecules. The "all-or-nothing" action potential is generated by the summation of excitatory and inhibitory signals in the form of chiral molecules that are found in a S (+) or R (−) isomer-enantiomer conformation binding and releasing from the receptor, generating a strong enough signal to cause the neuron to reach threshold. While the chiral neurotransmitters are mirror images of one another, it is important to remember that they are not the same molecule and will not exert the same strength of signal upon the receptor. The salience of the signal is determined by the strength of the ligand-substrate interaction. Thus, the individual effects of each neurotransmitter are tied to its particular chiral pair configuration.

With regard to the central stimulant actions on a regional structure of the central nervous system, the S (+) isomer is several times more potent than its R (−) enantiomer. The S (+) isomer is known to induce euphoria, whereas enantiomer R (−) has been linked to depression. The overall greater potency of the S (+) isomer form in such cases suggests that this form may have a higher potential for deep cranial stimulant actions and neurotransmitter availability in the synapse.

Figure 23:
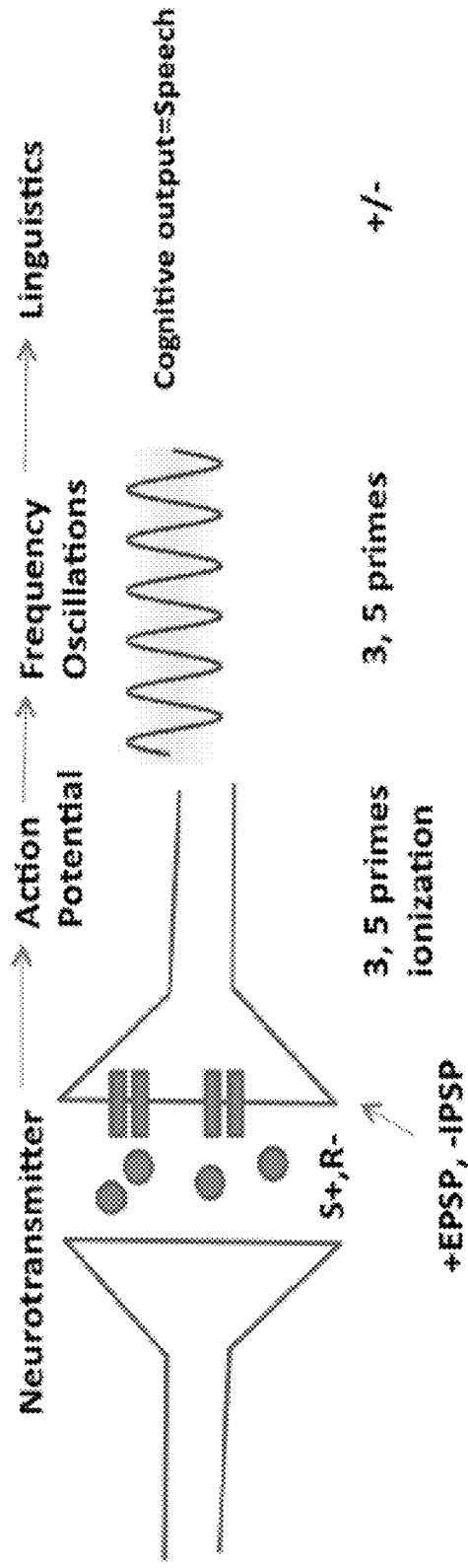
FIG. 23 illustrates an example of multi-level code translation to cognition.

The Unitary System: bridging the gap between biophysics and linguistics; Parallelism in cognitive phenomena. Parallelism in physical processes is a cornerstone of the FCU argument. That is, basic building blocks of language (letters) are analogous to DNA's role in protein formation, which is similar to the FCU's role in formulating coherent thought. We argue that the underlying units that compose cognition, like those of DNA, are relatively simple compared with the structures they create. This applies both to the brain itself and the way we perceive it (i.e., as a system of sensory inputs and linguistic and behavioral outputs). In our approach, we map the physical phenomena of cognition to this theoretical system. The functions "unary plus" (+) and "unary minus" (−), representing an increase or decrease in the underlying measured value, carry sufficient computational efficiency to represent human cognition, provided that the same linguistic base is present on both sides. Thus, demonstrating a basic linguistic parity among human minds would alleviate the need for a number-theory based approach to the conscious brain function that we seek to model. Mathematically speaking, in between the semantic primes and unary constructs, there exists a set of functions, which together with the unary construct form a new system of mathematics—the unitary system. The brain communicates within itself and with the rest of the body via unitary operators. These unitary operators carry a state of time and space that conveys information necessary to decipher any semantic or non-semantic based language. An example of multi-level code translation to cognition is shown in FIG. 23.

Since we postulate the existence of FCU and unitary system for communication within cognitive systems, we expect deeper examination to reveal correlations between that unitary system and the neurological functions at multiple levels, down to the smallest unit level of neurons. This is generally two, from the action potential down to the stimuli effect down to the cellular level of the body and how the DNA ciphers and deciphers specific protein segment corrections.

For example, the behavior of quarks, the smallest measurable particles known to man, is governed by 3 combinations of positive arrangements and 5 negative combinations. When DNA actually replicates itself it does so only on prime segments on 3 and 5, 5 and 3. It becomes apparent at the sub-atomic level that this 5/3 ratio relates to the quantum value of quarks residing within the sub-atomic particles, which in turn reside in the nucleus of the atom. That the quark codes on the state of 3 and 5, and the level of efficiency in doing so allows the body to repeatedly produce DNA at a high daily rate. If we look at the chemicals produced in the body, we see that a lot revolves around two arrangements of the atoms in the molecule—the enantiomer and the isome1 each chemical has 12 possible geometric configurations, with their combinations once again using primes 3 and 5. Once the specific chemical configuration is known, one can precisely engineer a medicine for anything that the body would need, either through stimulating the brain or correction of a damaged system.

The chemical action potentials that drive neuronal communication show the unitary system at work. This is due to the photoelectric exchange ratio, or the amount of photonic energy required ionizing an atom, or changing its charge state. For instance, if we assume that the ratio is 5:3, then 5 photons are required to ionize a given atom by 3 electrons. For example, if each photon has 1,759.2 KJ/mol of energy, then those 5 photons would ionize iron into the +3 state. The 5 photons would have to hit the iron simultaneously though. We theorize, however, that each actionable photon should hold the quantum of energy required for 1 electron. Thus, using the above example, rather than having 5 photons at 1,759.2 KJ/mol, we would ideally want 3 photons. Those 3 photons would have different energies. The first photon would have 759.3 KJ/mol to exactly match the first ionization energy of iron. Photon number 2 would have 1,561 KJ/mol to exactly match the second ionization energy of iron. And photon number three would have 2,957.3 KJ/mol, exactly matching irons third ionization energy. Since ionization is a key mechanism of intercell communication between neurons, this ratio, modeled by the unitary system, can be correlated with specific cognitive activities.

A quantum logical gate can be described as a unitary operator, assuming arguments and values in a product-Hilbert space. From an intuitive point of view, it seems natural to see the gate as a kind of truth table that transforms + and −. The gate can also be represented as a matrix. One can observe the same quantum physics at work when they consider cognition at the meso-level by examining the physiology of the brain; this is particularly significant in that it demonstrates the multi-level applicability of the unitary system. That is, the unitary system's underlying logic holds at both the quantum and cognitive levels.

Using the unitary system, information, coded using the FCU, travels from positive/negative cognitive constructs, to action potentials in neurons, to chiral molecular structures of neurotransmitters, DNA and proteins, governed in the end by quantum effects. On each of these different levels, the unitary system is being used to model the propagation information. Although it takes different forms at each transition, it can be described via a set of related mathematical formulas, rooted in number theory, which in turn exposes the most basic patterns and sequences of our universe. Understanding these patterns and transition will allow us to better understand the human mind, and to more precisely engineer specific compounds that the brain and body need to develop, heal, and perform better.

Information Processing—Does the brain use stochasticity in computation, or does it simply average out convergent neuronal input? Many scientists assume the latter, but those that challenge this assumption have to deal with a lack of mathematical tools. Active properties are based on the aggregate behavior of many voltage-gated ion channels that are in themselves stochastic mechanisms; tools already exist for the examination of these processes. The Shannon-Weaver Model of Communications, for instance, states that there are three levels, or obstacles, that must be overcome when constructing a system of interaction. In our case we are essentially reverse-engineering an existing system, but the claims made by this model are still equally relevant. In particular, this model calls for technical, semantic and effectiveness aspects of an interaction system to be resolved before it is deemed effectual.

The S-W model asks us how accurately the symbols of communication are transmitted; that is, if the rate of errors is low enough to maintain overall functionality. In the case of the human brain, it is clear that synaptic electrochemical mechanisms do a sufficient job of communicating signals between brain cells, but do the Unitary System and FCU properly account for this? The S-W model also demands conveyance of the precise meaning of symbols, and for the message to affect behavior in the intended way.

With regard to the communication aspect of the S-W model, a lot of signal noise occurs in neuronal transmission; in fact, transmission probability (i.e., the probability of reception) can be as low as 10%, and thus the method of neuronal signal transfer in itself is not particularly reliable. This is compensated for by greater redundancy. More reliable and stronger synapses do exist, but short-term signal modulation is difficult with these, as if habituation to transmitting a specific signal or type of signal improves the synapse. On the other hand, short-term modulation capacity's tradeoff is the fact that it depends on frequency and use-history.

In neurons, information is transmitted as "spikes;" it is unclear how exactly these spikes encode information, and there is a continuing debate in the field about whether the timing of these spikes is an important informational component. Conventional wisdom argues that the average firing rate is more important, and this is due to the apparent correlation between stimulus strength and firing rate. However, the observation of neuron firing rate by external measurement has some built-in latencies that make accurate measurement of these figures difficult.

Those who support the notion that neuron spike timing is important fall into one of two camps. First, there are those who argue that interspike intervals in the activity of a single neuron can potentially transmit information. In addition, others believe that the relationship between spike timings of different neurons may be important to the conduction of information. The latter argument is based primarily on the notion that synchronized neuron firing is an effective mechanism for activating postsynaptic cells, and is therefore an effective means for encoding information, especially in dynamic environments.

It is very difficult to conduct experimentation on neuron spike timing because statistical approaches such as principal component analysis don't offer insight into the coding strategies of neurons. Consequently, there needs to be significant progress in statistics and theory of stochastic information processing before a conclusion can be reached.

Proceeding from our prior assertions that the brain is fundamentally a linguistic computational engine and that its processes can be modeled topologically, we argue that the qualitative and quantitative specification of a Fundamental Code Unit is a prerequisite to a robust model of human cognition. This is because it will allow more accurate computational and mathematical reproduction. The FCU is not specific to one level of cognitive analysis (i.e., biochemical, quantum, psychological etc.) but, once specified, serves as a building block for the construction of new analogous thought structures outside the brain.

In order to support the notion that the FCU is the building block of thought, we must seek specific arrangements of phenomena within the brain. Within the brain, the FCU will correspond to the biochemical and molecular interactions that govern human thought. That is, synapse interaction and activation, as well as the protein exchanges between neurons, will comprise the FCU. In what way they do so, however, will depend on how the structures of linguistic expressions and cognition are reflected at this biochemical level. Thus, we seek to intuitively connect the simplest, most fundamental components of thought with the sophisticated, intelligent cognition we experience as thinking humans. The goal is thus to specify both the quantitative characteristics (i.e., how many molecular interactions or semantic components are needed to generate thought?) and the qualitative characteristics of cognition (i.e., what do FCU components and processes do in concert that would not be useful to our understanding of cognition if they were considered alone?).

If cognition is composed of like units, each must account for the various sources of conscious thought. The act of thinking, or reasoning, calls upon events in both long and short-term memory, in addition to applicable learned concepts. Because language maps thoughts to a coherent expression, linguistics is a potent source of cognitive insight. The FCU takes this relationship between thought and linguistic expression a step further by mapping the underlying physical processes that ultimately lead to this expression of language and behavior. Since cognition is a spatial as well as temporal phenomenon, the units that describe and comprise it must reflect both of these dimensionalities. Thus, we introduce the mind state, or a physical approximation of the human mind or a subset of it at a given point in time, and use the Markov Decision Process model to map its transitions through reasoning and decision-making.

In cognitive processes, predictions based on the present are not made any more precise through additional information on the past. All useful information for predicting the future is contained in the current state of the process. One of the most useful tools for studying this property is the Markov chain. A Markov decision process (MDP) allows individuals to make decisions when there is inherent certainty about the current state and uncertainty about the effect of their actions.

Assuming that a state of mind evolves over time, then any change has a given probability of being positive or negative. Now, should one want to control the state of mind, there is a range of possible actions (e.g., therapy) that, in turn, are also probabilistic. The efficiency of the control exerted is measured based on the positivity or negativity of responses throughout the experiment. The process can be summarized as follows: when in state s, there is probability p that, having chosen action a, the subject finds himself in [new] state s' with benefit b. The progression of mind states corresponds to a Markov chain. In other words, the mind follows a sequence of distinct states over time, based on the probability of each transition. According to Markov's hypothesis, transition probabilities depend exclusively on n previous states. Generally, n is equal to one in order to restrict analysis to the current state and the following state.

A Markov process is an {S, A, T, R} quadruplet where:

S={S0, . . . , S/S/} is the finite discrete set of possible states;

A={a0, . . . a/A/} is the finite discrete set of possible actions;

T:S×A×S→t [0;1] is the function describing the change in state resulting from the cont1v1 actions.

Figure 24:
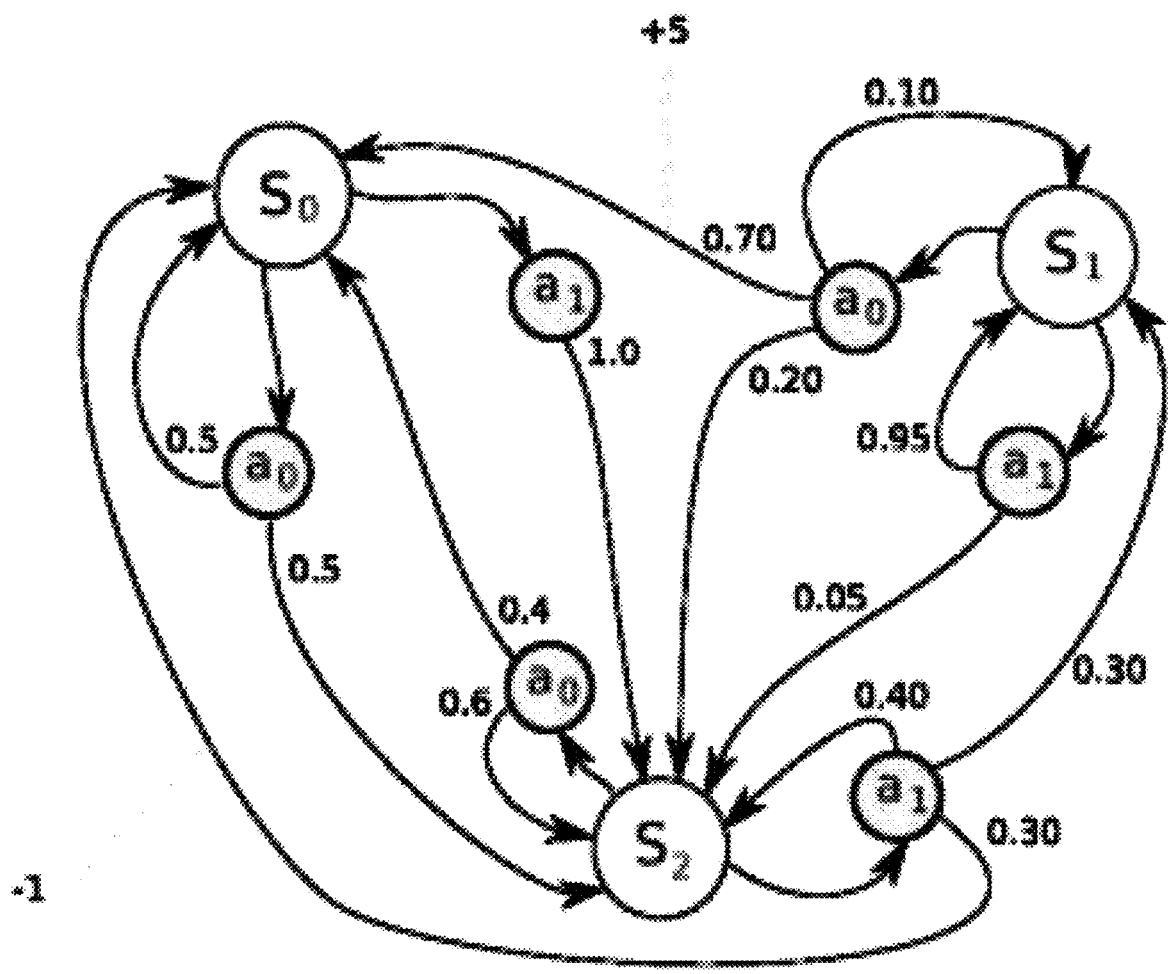
FIG. 24 illustrates an exemplary MDP showing transitions between three mind states.

Generally, the T function is probabilistic: p(s'|s,a)=T (s, a, s') being the probability that the mind goes from state s to s' when action a is undertaken. R:S×A×S→[ ] is the reward function indicating the real product of choosing action a while in state s in order to achieve state s'. An exemplary MDP showing transitions between three mind states is shown in FIG. 24.

Figure one represents a MDP for three different states {S0, S1, S2}, shown in green. From each state there is the possibility of choosing an action from the set {a0, a1}. The red nodes therefore represent a potential decision (the choice of an action in a given state). The numbers indicated on the black arrows indicate the various transition probabilities for each decision node. Finally, the transitions can generate rewards, as shown by the upward yellow arrow (+5) and the downward yellow arrow (−1).

The transition matrix drawn from a0 is:

$$\begin{pmatrix} 0.50 & 0 & 0.50 \\ 0.70 & 0.10 & 0.20 \\ 0.40 & 0 & 0.60 \end{pmatrix}$$

The transition matrix drawn from a1 is:

$$\begin{pmatrix} 0 & 0 & 1.0 \\ 0 & 0.95 & 0.05 \\ 0.30 & 0.30 & 0.40 \end{pmatrix}$$

With regards to rewards, there is a +5 reward when going from S1 to S0 by doing a0 and a −1 reward (also called penalty) when going from S2 to S0 by doing a1. Using this mind-state mechanism, we argue that it is not only possible to approximate cognitive processes in a computationally efficient manner, but that these same processes occur in the physical realm.

Taking the analysis a step further in the spatial direction, we introduce an algebraic component. Begin with an infinite set S representing brain regions that may be activated by some means. We introduce a σ-algebra A on that set, and call the elements a∈A activation sets (by definition, a ⊂ S]. Next, we introduce a second set W whose elements are labeled concepts in the brain that correspond to words. For some subset A ⊂ 𝒜 there is a mapping P: a'∈ A→w∈ W called the concept activation mapping. The elements a' of A are action potentials. Let P̃:w∈ W ⟼ ā∈ 𝒜̄ be a mapping we call the brain activation mapping. Let μ be a measure on S, and let ℱ:A→{+, −} be a parity mapping. An axiology is a mapping Ξ: W→{+,−} generated by computing $$f(w) = \int_a \mathcal{F}(s)d\mu, \text{ with } a = \tilde{P}(w) \text{ and then projecting } \Xi(w) = \text{sign}(f).$$

Definitions of symbols for such mappings are shown in FIG. 25.

This system describes the mental mood states of an individual by examining the mind's abstract structures. Throughout the brain there are various forms of activations (electrical, chemical, biological) each contributes individually or within groups to the formation of new concepts, which define a positive or negative mental state. Series of such activations form an activation set, this set represents a connected structure for each activated region, which is defined in terms of a node. The node circumference changes based on the duration of the region being activated and the reflexivity is due to the re-activation of this region at different instances.

Figure 26:
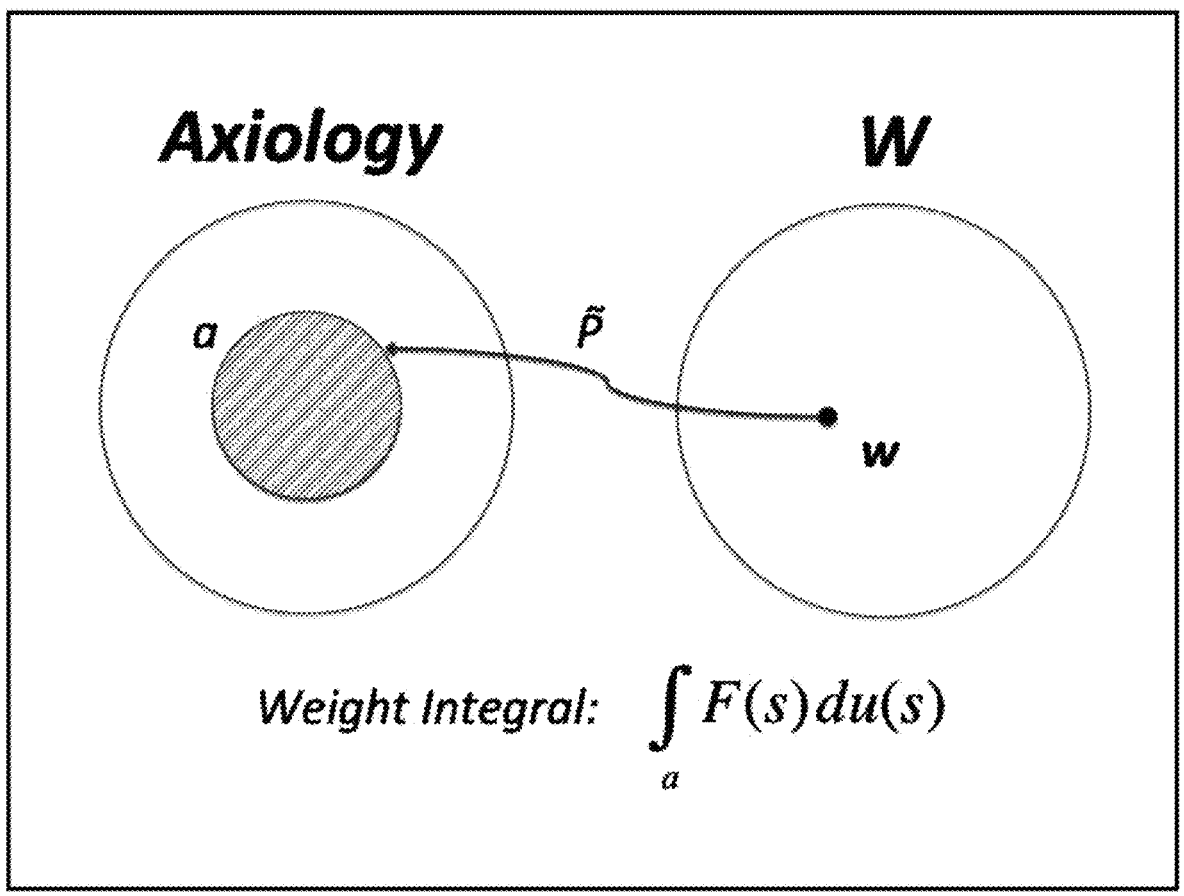
FIG. 26 illustrates an example of integration of a node activation of a set integration using the unitary system axiology.

An example of integration of a node activation of a set integration using the unitary system axiology is shown in FIG. 26.

Maximum Entropy Statistical Analysis of the Unitary System and FCU—The Maximum-Entropy (Maxent) model of statistical analysis can be used to test the fidelity of the predictions made using the Unitary System, as well as to determine how much and what type of data should be encapsulated in the Fundamental Code Unit. Maxent is a discriminative, or conditional, model that accepts input data and uses its inherent patterns to infer about missing data—in this way, the results of a Maxent analysis become more accurate not only in proportion to the amount of data available, but the type of data as well.

To construct a Maxent model for Unitary System analysis, we must establish several prerequisite features, or pieces of evidence tying observations (i.e., empirical data), to our predictions about them. In Natural Language Processing (NLP), these features often include the specific word being analyzed, its shape (hyphens, suffixes, and prefixes etc.) nearby words, and their features. [cite Klein] In the case of the FCU under the Unitary System, we can use Maxent not only to examine the features FCU at the unit level but also the correlation between Unitary System mathematics and the process by which fundamental code units are transmitted within the brain, and then expressed behaviorally. Thus, we are testing two separate analytical levels using Maxent. The first is the qualitative composition of the FCU, or the features it encompasses. Comparing the FCU to linguistic expressions and other behavioral observations will allow measurement of the conceptual preservation of the FCU. We are also measuring similar preservation between the Unitary System's unary function-based model and the observed spike-pulse alphabet that we observe within the brain.

Application for Unitary System and FCU—The unitary system promises a straightforward approach to modeling cognition as an intuitive mathematical model. This system is applicable at multiple levels of brain function, from language acquisition to neuronal interaction to DNA replication and the subatomic processes that govern it. We argue that the strength of the unitary system lies not only in its wide applicability in the cognitive realm but in the new opportunities it offers to researchers and scholars of cognition: the ability to discern a fundamental unit of thought. Combining the unitary system with empirical data promises to help determine not only the quantitative minimum of cognition (i.e., the number of active neuronal connections that form conscious thought), but its qualitative foundations as well.

Ultrasound is well established as a diagnostic imaging tool but its therapeutic potential, particularly for central nervous system disorders, has been largely overlooked until now. Recent technological advances now allow transmitting and focusing of ultrasound through the intact human skull using an array of phase-corrected ultrasonic transducers placed on the cranium. As the technology matures and the control over brain effects becomes more fine-grained, an understanding of the structural relationship between cognition and its physical media will allow greater therapeutic strides to be made.

Such non-invasive, focused ultrasonic intervention permits thermal (high power) and non-thermal (low-power) modes. Non-invasive, thermal ablation of thalamic nuclei using ultrasound has recently been demonstrated to be effective in the treatment of neuropathic pain patients. We argue in favor of the use of non-invasive, focused ultrasound in non-thermal stimulation and suppression of neural activity. We hypothesize that non-invasive, transient and focused ultrasonic neuromodulation (USN) offers great potential for the therapy of psychiatric disorders that are associated with dysfunction in defined anatomical structures but evade effective pharmacological treatment.

Discourse Analysis—Within the realm of cognitive studies, we posit that one can analyze a state of mind as "positive" or "negative," which can also be expressed along the time axis, as being future-oriented or past-oriented. Human cognitive architecture allows us to digest information as negative or positive values. However, it is by processing our cognitive structure with this cognitive architecture that we can judge whether a given concept has a positive or negative value. During discourse, we unconsciously select words, which signify positive or negative concepts. Thus, unary functions, i.e., '+' and '−', allow efficient processing of language information provided that you have the same linguistic base on the communicating parties. The linguistic base is essentially the sum of any natural language, which evolved over time to include semantics with level of sophistication and potency, built on the foundation of embedded semantic primes. The semantic primes, i.e., concepts that are understood intrinsically, have positive or negative values in the shared value system, or axiology.

Analyzing discourse, one can deduce positive and negative values for specific words, based on the intrinsic value, time orientation, context, and frequency. Internal or interpersonal discourse, associating concepts with their positive or negative values (e.g., abstracted as reward/punishment, pleasure/pain, etc.) drives the actions and attitudes, and can thereby be quantified, analyzed, and corrected. This has applications for diagnostics and treatment of mental disorders, starting with depression, and general implications for cognitive modeling. Mathematically speaking, in between the semantic primes and unary constructs, there exists a set of functions, which together with the unary construct form the new system of mathematics—the unitary system. The brain communicates with other organs, and within itself, in unitary operators. The unitary operators carry a state of time and space, conveying all that is necessary to decipher any semantic or non-semantic-based language, including pictorial languages.

The diagram below depicts the underlining actions that take place in the brain at the various levels from biological, electrical, chemical through the cognitive and linguistic levels. Here, we are trying to trace how a word, in this particular example "Life" can be viewed by a patient and what formulates the mood state associated with it. Words are processed in the brain based on their letters and how each letter relates to the other from a value standpoint. When analyzing a word value we cannot disregard the fact that each group of words can represent a concept that could be significant to understanding a patient's state of mind. Looking closely at what triggers this mechanism of word valuation and mood identification, we first examine the atoms that react and interact with one another while their chiral molecules produce different biochemical effects that in turn generate electrical signals. The signals characteristics specify the isomer-enantiomer molecules that result in euphoric or depressive state of mind respectively. These mood states are associated directly to the energy generated at various signal spectrums.

The resultant S+ and R− will trigger chemical secretions at the synaptic levels and uniformity of such interactions will result in a unary operation that compensates for the elevated levels of such chemicals. Only signal frequencies that are involved in this particular evaluation are considered. Hence, frequencies <4 Hz are only taken in consideration for the sake of our example. In other cases, we look at different frequencies associated with the neuron activation. Particularly, in some instances we might need to considered these signals at different time frames and frequency oscillations due to their direct affect in determining the value of each letter or word. The operation that takes place at the synaptic level generates various resultant signals which when correlated generated signal amplitudes that represent various letters of the alphabet. This unitary system produce particular signals with amplitudes and oscillations that are directly associated with letter values and mood characterization. After each letter has been thoroughly examined and analyzed compared to the previous and preceding letter, it is subjected to a value assignment which when calculated as a whole produce a positive or negative axiological value that represents a mood state at that particular time instance within a specific context. Although the various words form concept but some, especially if they are universally accept form conceptual metaphor, which are evaluated using the same framework, described here.

A practical application of this form of discourse analysis is the LXIO cognitive mood analyzer developed by Howard et al. (2011) that parses sentences into words that are processed through modules to evaluate cognitive states. Words are processed through time orientation, contextual-prediction, and consequent modules. LXIO relies on two core concepts in its formulation of mood: first, human states of mind are a spatiotemporal phenomenon. That is, the human mind's progression from one state to the next can be quantified by variation in these units, which in turn forms a pattern of change over time that can be mapped to coherent thought.

Regardless of language, LXIO takes into account linguistic expressions. LXIO is a word-value-based analyzer that assigns positive and negative values to each parsed word based on the modules. The primary metrics for LXIO analysis include the time frame, orientation and concept set of the words spoken by the subject. This way, the activation of certain concept sets can be correlated with environmental and physiological variables in order to determine the causative agent in thought process, as well as its future progression.

As an alternative to the compartmentalized notion of cognition many researchers propose, LXIO is a testable means of insight into the relationship between language and underlying cognitive structures; it promises to yield techniques for automated diagnostics of PTSD, depression and similar symptoms, as proof of concept. Using metrics such as the cultural or traditional significance of spoken words and phrases, the frequency with which they are used, and their context relative to other phrases, LXIO projects the "value" analysis of a given statement. Thus, in its analysis of mood state and diagnostics, LXIO subjects all input to the same fundamental mathematical transformation, and in doing so it produces positive clinical results.

With respect to cognition, the significance of LXIO is its ability to incorporate conscious thought and its bodily expressions, linguistic or otherwise, into a uniform code schema. The ability of LXIO to diagnose brain conditions based on mood analyzed through speech lends credence to our view that the whole of cognition, including language, consists of a series of different structures arising from the same units.

fMRI Neurofeedback—Shibata et Al. (2011) describes a fMRI neurofeedback method for inducing visual perceptual learning that bears relevance to our position in that their findings contain two important implications: First, visual perceptual learning (VPL) in the Early Visual Cortex of adult primates is sufficiently malleable that fMRI feedback can influence the acquisition of new information and skills when applied to the correct region of the brain. Second, these methods can induce not only the acquisition of new skills and on formation but can aid in the recovery of neurological connections that have been damaged by accident or disease. For instance, a trauma victim suffering from language skill loss can potentially recover those skills through fMRI neurofeedback induction.

What Shibata's paper shows us about the structure of thought is that the FCU which we seek in cognition must be based on some finite number of neurological connections—those same connections influenced by the activity of fMRI neurofeedback. This process does not target a single neuron, but a locality of connected neurons, and based on its positive effects on the conscious process of Visual Perceptual Learning, the FCU represents that reality. In addition, Shibata's fMRI induction research can provide powerful evidence for the composition of thought because it can be used to determine the m1mmum amount of neuronal connectivity for the formation of thoughts. The goal here is not to state that it takes n neuronal connections to constitute a coherent, conscious thought; instead, we treat n as any number of neuronal connections that satisfies specific qualitative requirements. In this case, it may be the number needed to produce some response to fMRI neurofeedback induction.

Toward a superior computational understanding of brain function—In order to study brain function, some researchers have attempted to reverse-engineer neuronal networks and even the brain itself. This approach was based on the assumption that neurons in-vivo acted just like simple transistors in-silico. Unfortunately, both network and whole-brain modeling have led to very little insight into actual brain function. This is largely because transistor-based computing reacts to static events whilst neurons can react to processes. In contrast to transistors, neurons can establish and change their connections and vary their signaling properties according to a variety of rules, allowing them to adapt to circumstances, self-assemble, auto-calibrate and store information by changing their properties according to experience. Consequently, a detailed understanding of neuronal function and network organization is required prior to neuronal network modeling attempts.

Economy and efficiency are guiding principles in physiology. We thus argue that understanding the design rules which shaped neuronal function and network organization will help us in understanding and modeling of brain function. This notion was already recognized about 100 years ago by Cajal, who stated "all of the formations of the neuron and its various components are simply morphological adaptations governed by the laws of conservation for time, space, and material.

The structural and physiochemical relationships that connect resource use to performance in the brain are determined by three major constraints: geometrical limitations on packaging and wiring, energy consumption considerations, and energy-efficient neural codes.

One obvious difference between current in-silica technology and the brain is their three-dimensional organization. Most microprocessor chips use a small number of layers of planar wiring. In contrast, neurons wire in a complete 3D fashion. Various studies have examined optimal geometric patterns of connectivity; and find that neurons, arranged in cortical columns, strike the optimum balance between two opposing tendencies: transmission speed and component density. Understanding the design rules underlying the micro-level column organization thus will be crucial for a better understanding of the brain as a whole.

Energy usage poses another conspicuous difference between neural networks in-silica and in-vivo. The Blue Gene/IP supercomputer used to model a cat's cerebral cortex, requires several times more energy than an actual cat brain and still runs about 100 times slower. The main issue is that transistor based networks convert most of the energy used into heat. Brains make considerably more efficient use of the energy they consume (about 20% of the resting metabolism. Of this energy, about 50% is used to drive signals along axons and across synapses with the remainder supporting the maintenance of resting membrane potentials and the vegetative function of neurons and glia. It should be noted that cortical gray matter consumes a higher proportion of energy (75%) than white matter, highlighted by the fact that global connectivity in the co1iex is very sparse: the probability of any two neurons having a direct connection is around 1:100 for neurons in a vertical columns 1 mm in diameter but only 1:1,000,000 for distant neurons. These findings point to another major design rule: use the majority of resources for modular, local signaling and computing (gray matter) and spend the rest on long-range communication (myelinated axons: white matter) linking the distributed computational units.

The development of a FCU promises several important applications for brain disorders as well. Crespi et Al. (2009) demonstrate a dian1etric relationship between the genes affecting autism and schizophrenia. Specifically, there exist four specific genetic loci at which deletions are linked to autism and duplications to schizophrenia, or conversely, deletions are linked to schizophrenia and duplications to autism. This unexpected structural link between two otherwise unrelated brain disorders has several important applications. First, it is indicative of a fundamental similarity between inherited brain disorders as a whole—not only in the way that they affect the brain, but the patterns of genetic affect that cause them. Second, it provides an important application for the FCU not only as a way to quantify what we define as cognition, but as a benchmark for faulty brain processes. Like cognition, language, and DNA itself, brain disorders may be analogous in the sense that they are also complex combinations of a few simple processes such as genetic mutation at specific loci.

Finally, energy constraints also govern the optimal coding schemes. It is well established that redundancy reduction is a major design principle in the cortex. By maximizing the ratio between information coded and energy expended for signal transmission and resting state maintenance, sparse coding regimes improve energy efficiency. Sparse coding regimes, in which a small proportion of neurons signal at any one time, have the additional benefit of a large representational capacity.

An improved appreciation of the geometrical and energy constraints that are fundamental to the functioning of the brain should provide a valuable guide for the study of neuronal network architecture and coding. We have already learned that neurons do not statically integrate information as transistors do and also that the electric fields generated by neuronal activity in turn can affect neuronal activity itself. We should thus ask whether it is appropriate to assume a binary code for neural networks or whether a more holistic view is required. Current attempts to computationally mimic brain function attempt to do so by fitting form to expected function; our unitary system offers an alternative to persisting in a computer hardware-inspired understanding of the human brain by asserting the necessity of comprehending the physical expression cognition on each medium at which it operates.

Model—In embodiments, a system may model the different mediums of brain function in a mathematically uniform manner. This system manifests itself in many ways relating to brain physiology, from neuronal activity, to molecular chirality and frequency oscillations. An improved appreciation of the geometrical and energy constraints that are fundamental to the functioning of the brain should provide a valuable guide for the study of neuronal network architecture and coding. A better understanding of intelligence can help scholars of artificial intelligence overcome the energy consumption and efficiency obstacles they face in reproducing the human brain's performance at the hardware level. Modeling brain function promises insights to the paradox of the low energy consumption and high cognitive output of the brain.

A method for efficient coding at the level of neuro-linguistics is explained here. The process by which the brain analyses the mental state of an individual provides is an efficient learning algorithm and a great example of efficient coding. One of the ways in which the brain examines the mental state of an individual is to analyze the mind's abstract structures. Throughout the brain there are various forms of activations (electrical, chemical, biological) each contributes individually or within groups to the foundation of new concepts, which define a positive or negative mental state calculated by the MSI algorithm (Howard 2011).

Brain areas that underlie value-based choices should receive value-based inputs from all choice options and then decide a winning value choice. Several authors used a neural network model to mimic the choice decisions and found that value-based decision-making occurs at low frequencies of <10 Hz. They studied Magnetoencephalography (MEG) data from humans to confirm their network model and determine brain areas corresponding to the value comparison. The parietal and the prefrontal cortices were implicated in value-based choices. The advantage of MEG is that possesses high temporal resolution as the value comparison is being made and can detect more accurately than fMRI the time after the decision has been formed and how the choices are made over time.

The parameters that are used for the network model such as frequency oscillations are related to biophysical properties such as inhibitory (−) inputs, concentration of neurotransmitter, which can be measured locally using fMRI/MEG/magnetic resonance spectroscopy (MRS). Therefore MEG can be used to measure FCU in frequency oscillations associated and fMRI used to measure brain areas involved during axiology (another level of FCU analysis) using the MSI algorithm during patient testing in and MRS can be used to determine FCU in neurotransmitters involved. For example, the frequency oscillations that are based on excitation/inhibition balance in patient's brain is measured using fMRI+MRS+MEG as patients are in discourse, and simultaneously, excitatory/inhibitory neurotransmitters are correlated. Therefore, multiple modalities can be used to measure FCU at different levels in parietal and prefrontal cortices in response to discourse, where mood states and word value can be also calculated.

By recording from the OFC and ACC of monkeys' brains some scientists were able to train monkeys to make decisions. They found that OFC neurons evaluate a choice based on recent choice values, while ACC neurons integrate multiple decision parameters, positive and negative values, predictions, and errors to evaluate choice. If these brain areas are damaged, it results in impaired decision making, suggesting these areas as the seat of value comparisons in the brain. The neuronal coding scheme employed by prefrontal cortical neurons was based on associating different firing rates to different aspects of decision-making. However, they found that ACC uses a positive valence-encoding scheme for all aspects of decision-making and evaluates reward prediction errors.

The OFC is likely to be activated during context based word value decisions and encodes an adaptive value signal that changes based on recent value history, while ACC during and encoded value on a fixed scale to evaluate how choice outcomes are related to prior expectancies. This provides the subset of prefrontal cortical neurons that are involved in determining value and can be identified in imaging studies as the regions correlated to word value axiology. The coding scheme of neurons to calculate value and compare is reminiscent of GC and comparing + and − values and forming an aggregate output. Hence, we can suggests that a write modality to feedback different word values or mood states can be used to control OFC and ACC to improve mood states and decision making.

Hence, if we were to trace the activations that trigger such behavioral outputs we find them at various levels. A series of such activations form an activation set, this set represents a connected structure for each activated region, which is defined in terms of a node. The node circumference changes based on the duration of the region being activated and the reflexivity is due to the re-activation of this region at different instances. Each node representing a fom1 of activation can also be connected to another node that can vary in shape and time orientation. The segment connecting the various nodes to one another represents the time orientation. Once this connected structure is formed, a new activation set is created. This activation set can also be connected with other activation sets to create a concept set. In other words, nodes within the same set are added together based on the unary system computation and they are represented in terms of waveform signals that are weighted by a statistical coefficient to produce a resultant active node.

Figure 27:
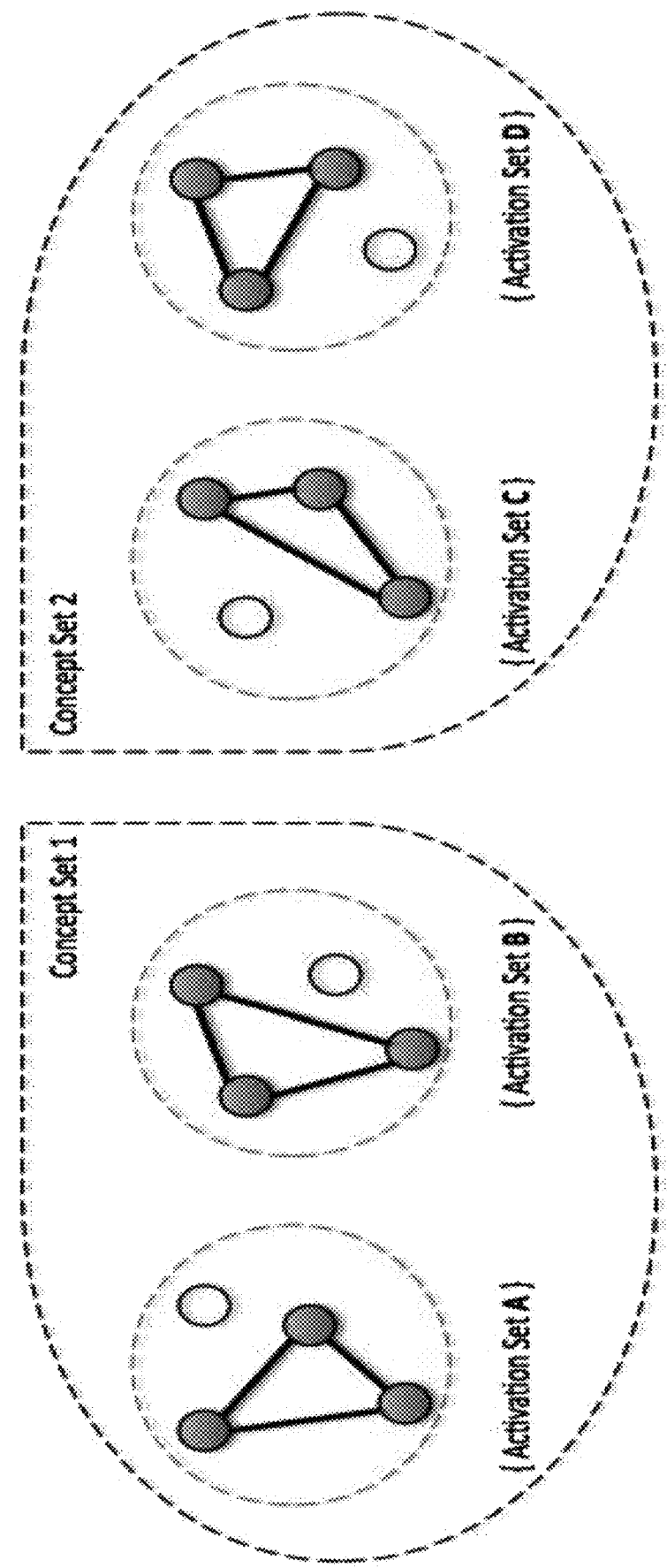
FIG. 27 illustrates examples of two different concept sets {1, 2} each consisting of two or more activation sets.

FIG. 27 shows two different concept sets {1, 2} each consisting of two or more activation sets. These sets have been generated through the interaction of neural activity at the various cognitive levels. Each node of those sets represents an active region that is either dependent on other regions to complete its "cognizant" state or is self-dependent but cannot form a comprehensive notion. Two active states that are can form a uniform concept interact together to define a concept set.

Each node represents an active region of the brain, which consumes energy to maintain continuous neural activity. Throughout the various stages of our analysis energy is being generated and propagated from the molecular level to every signal mechanism. Looking closely at the activation sets we can clearly distinguish the various levels of interaction ranging from chemical/biological, electrical to cognitive-energy activation of brain regions. Components at each level interact with one another in a unary structure producing a consistent function of activity. As a whole the various levels that active these brain regions form a unitary system of operation that affects the brain from the molecular through biological to the cognitive levels to interaction.

Figure 28:
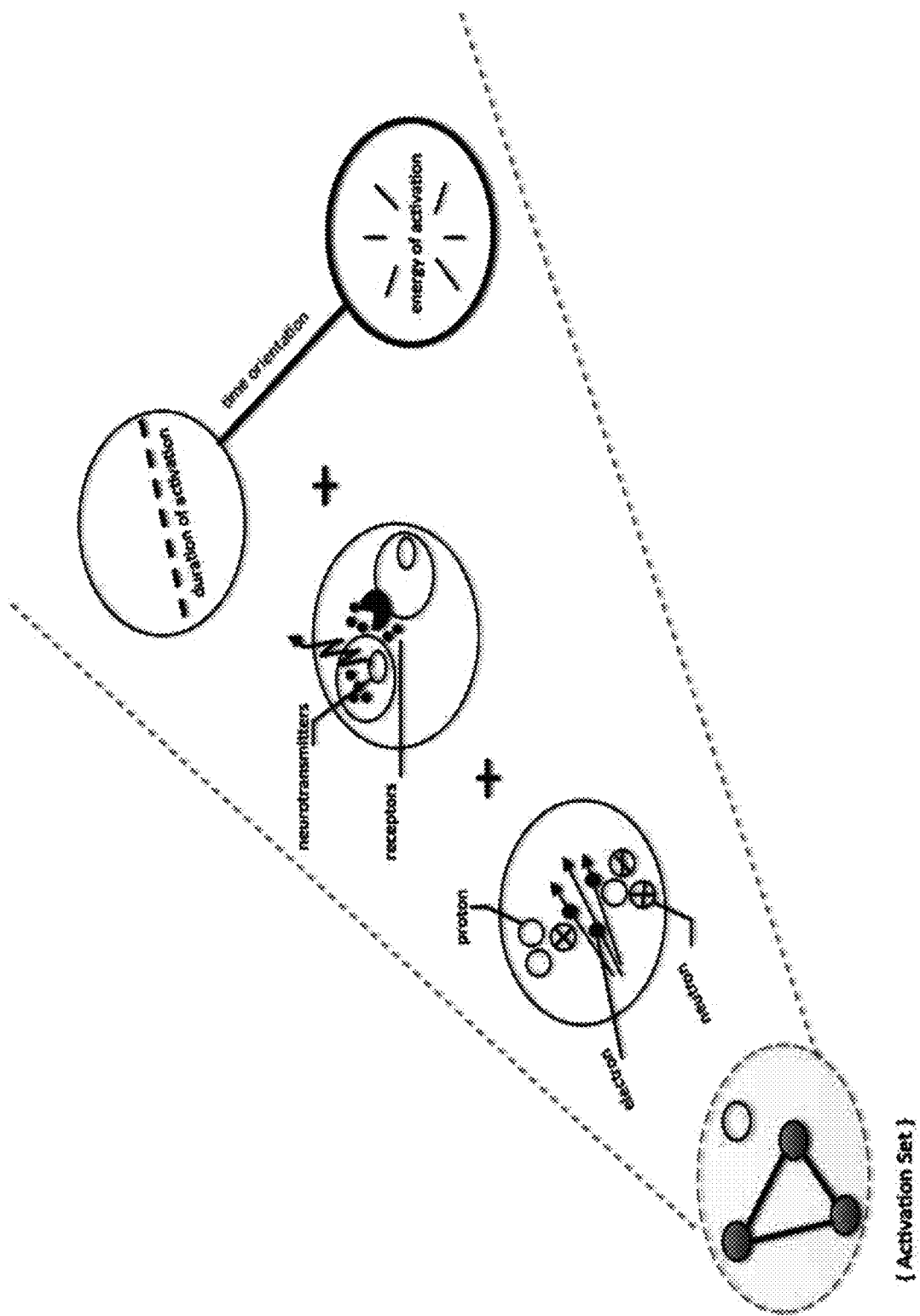
FIG. 28 illustrates examples of the set of concepts derived from the connected-activated sets, which produce an axiological value that represents a mood state after being projected on a positive and negative plane.
Figure 29:
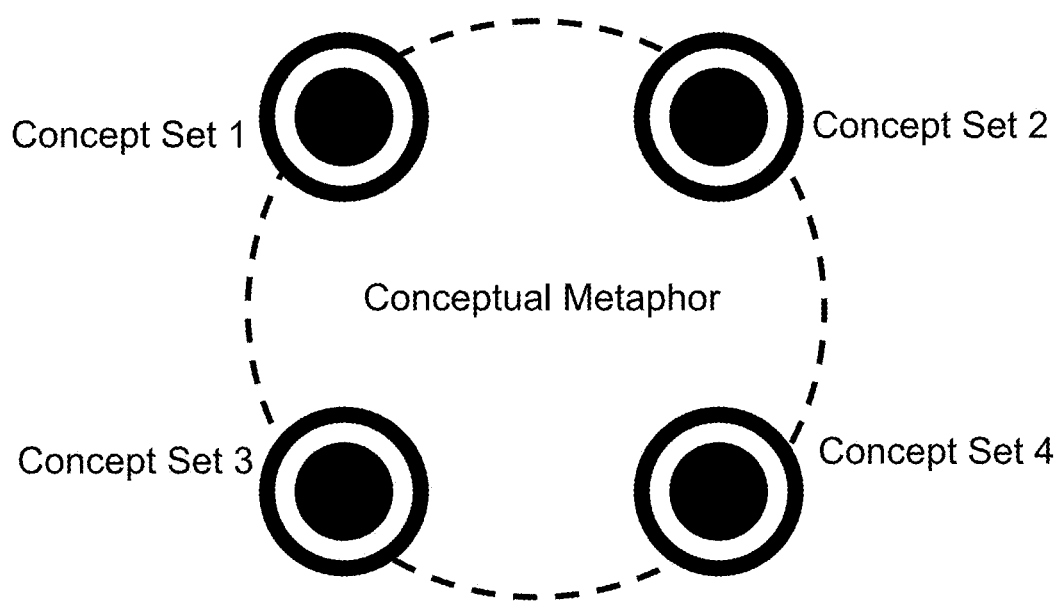
FIG. 29 illustrates examples of correlated and dependent concept sets form a conceptual metaphor that remains consistent in terms of its axiological value despite changes in time.

As shown in FIG. 28, the concept set is the set of concepts derived from the connected-activated sets, which produce an axiological value that represents a mood state after being projected on a positive and negative plane. The concept set is defined by the activation set with higher value. Therefore, a concept can be formed when other activation sets are elements of it but their contribution (effect) is diminished by another dominant activation set. The value of the resultant concept set can have various ranges from positive infinity to negative infinity, only after its projection that these values become a unitary positive or negative. As shown in FIG. 29, correlated and dependent concept sets form a conceptual metaphor that remains consistent in terms of its axiological value despite changes in time.

Several problems facing contemporary scholars of cognitive science have been described above. First is the diverse set of definitions of cognition that pervade the research discourse. While many believe that thought consists of several fundamentally different subtypes, we went on to argue that, like DNA or a grammatical alphabet, cognition is a complex construction of a series of simpler constructions, or fundamental units, and that the overall behavior of cognition in terms of these units can be described using a unary mathematical scheme known as the unitary system.

While decoding the exact composition of each "letter" in the alphabet of thought from the sheer combinatoric complexity of the brain is outside the scope of this paper, we have shown biophysical evidence for a set of simple signals that compose cognition, and using the unitary system, we have also demonstrated a clear link between those signals and the linguistic expressions of conscious thought. In particular, we argue that concepts articulated linguistically can be placed on a continuum of positive and negative values based on factors such as environmental variables and linguistic and behavioral context.

The core claim is that these processes are closely interrelated and can be described mathematically in a uniform manner. The multi-level model of information exchange in biological systems, from abstract concepts in the brain down to the molecular interactions guides the development, functioning, and communication within the brain. The schema of coding is utilized to express behavior, intelligence, cognition, and conscience. The schema code governs fundamental neuronal communication across all brain activities, and forms the fundamental unit of thought. The link between cognition and linguistic articulation means that the unitary system can be used to model cognition both at the biophysical level and at the linguistic and system levels, and showed that it is imperative to comprehend its expression on each of these mediums because of their mathematical continuity.

Combining the unitary system with empirical data promises to help determine not only the quantitative minimtm1 of cognition (i.e., the number of active neuronal connections that form conscious thought), but its qualitative foundations as well; the DNA of brain language and human thoughts. The decomposition of cognition into these basic units governed by an intuitive mathematical model has potential applications in a number of fields, such as neurological and psychiatric therapy, discourse analysis, and a better understanding of intelligence that can help scholars of Artificial Intelligence overcome the energy consumption and efficiency obstacles they face in reproducing the human brain's performance at the hardware level.

Figure 30:
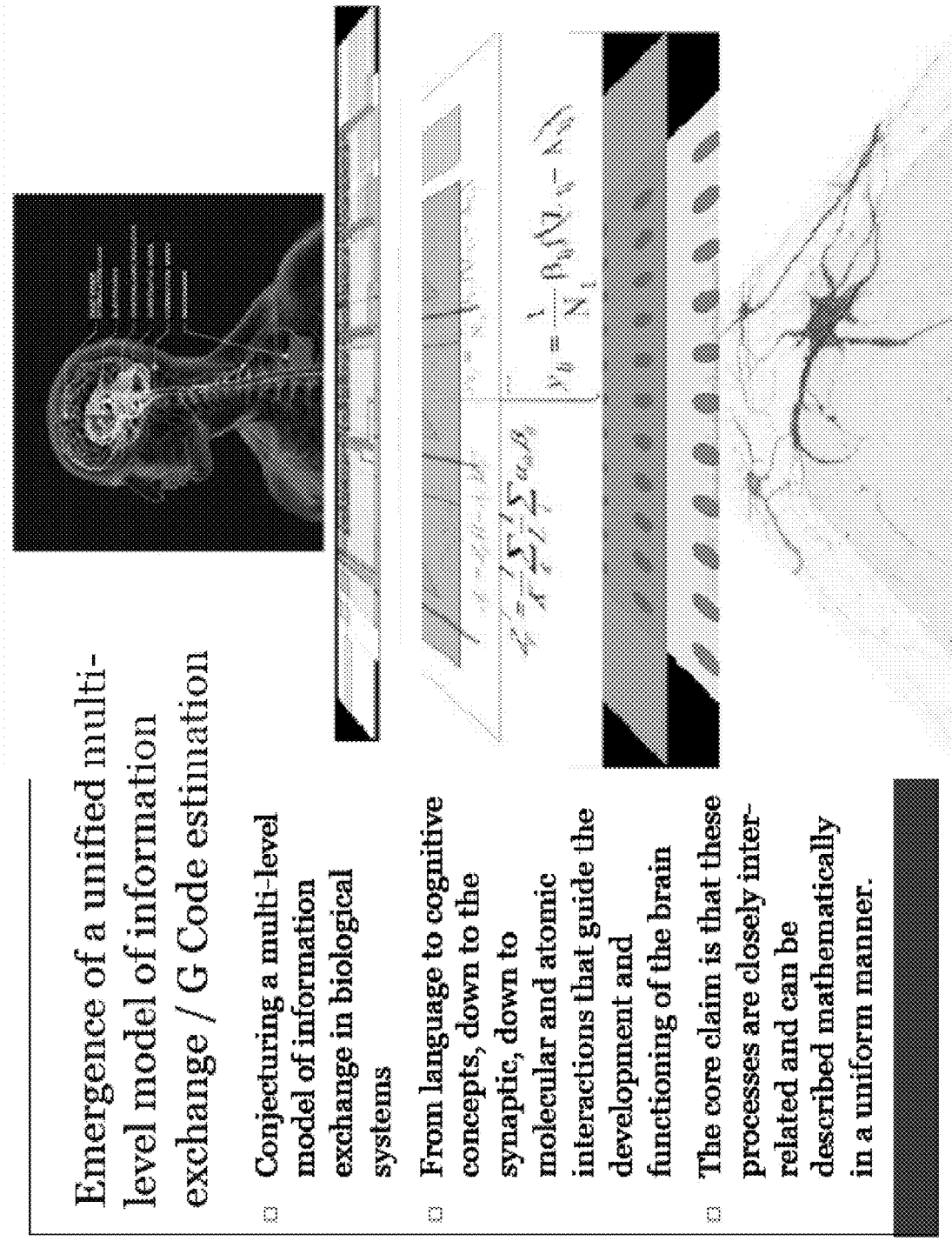
FIG. 30 illustrates an example of the emergence of a unified multi-level model of information exchange/G code estimation.

In FIG. 30, an example of the emergence of a unified multi-level model of information exchange/G code estimation is shown. This example shows a multi-level model of information exchange in biological systems, from language to cognitive concepts, down to the synaptic, down to molecular and atomic interactions that guide the development and functioning of the brain. The processes may be closely interrelated and may be described mathematically in a uniform manner.

An example of elements of time including effect based on duration and time evolution is shown in FIG. 31. An effect based on duration may include the weight mapping and parity mapping being dependent on a duration parameter. The time evolution may involve both the concept activation mapping and the brain activation mapping being presumed to change over time, either (i) in response to external stimulus, or (ii) in response to "instantiating" the mapping d $\mathcal{F}$ (a, t+$\delta$t, $\Delta$t)=f(a, t, $\delta$t, $\Delta$t, $\mathcal{F}$ (a, t, $\Delta$t)).

Figure 32:
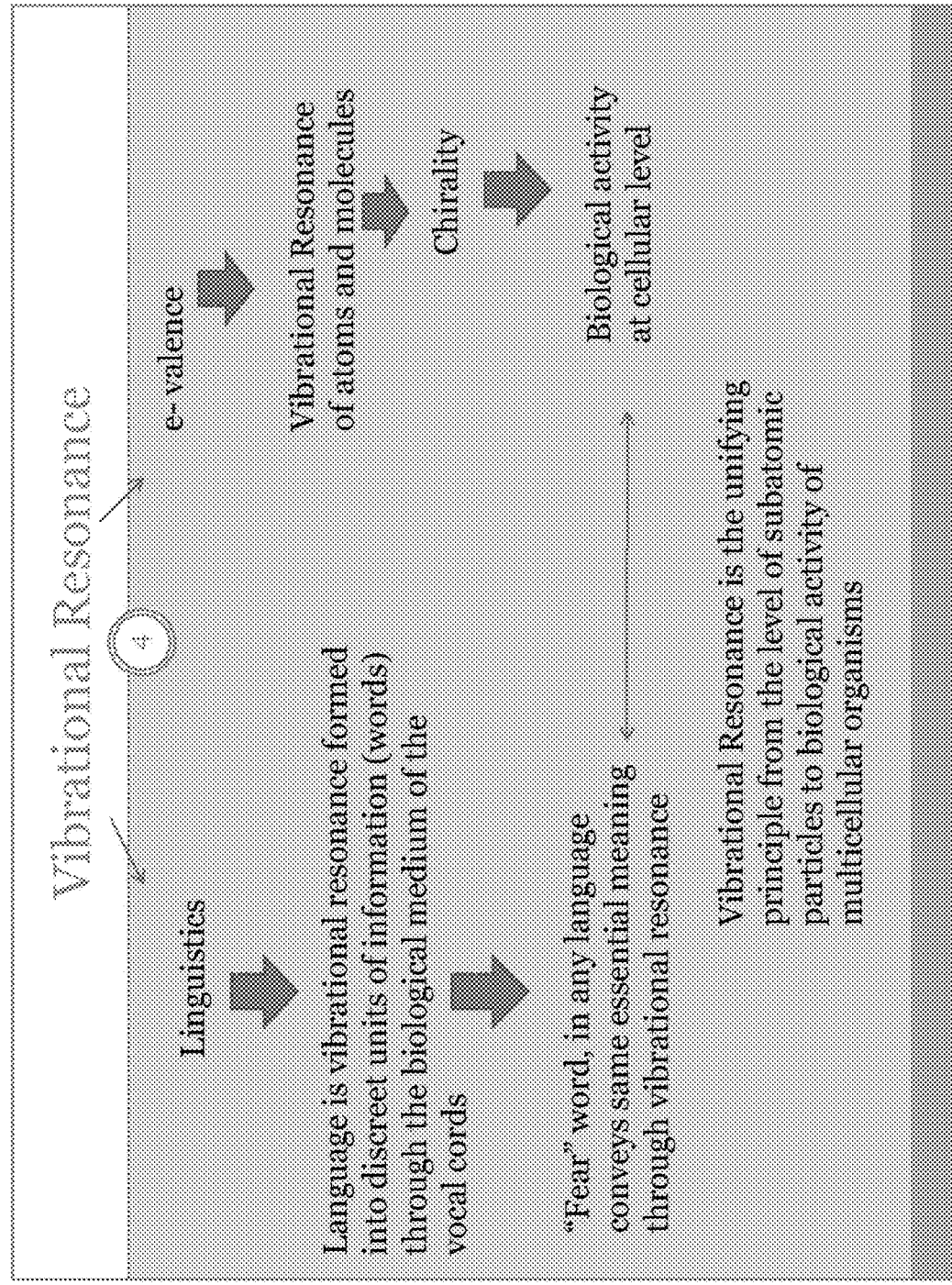
FIG. 32 illustrates an example of vibrational resonance.
Figure 33:
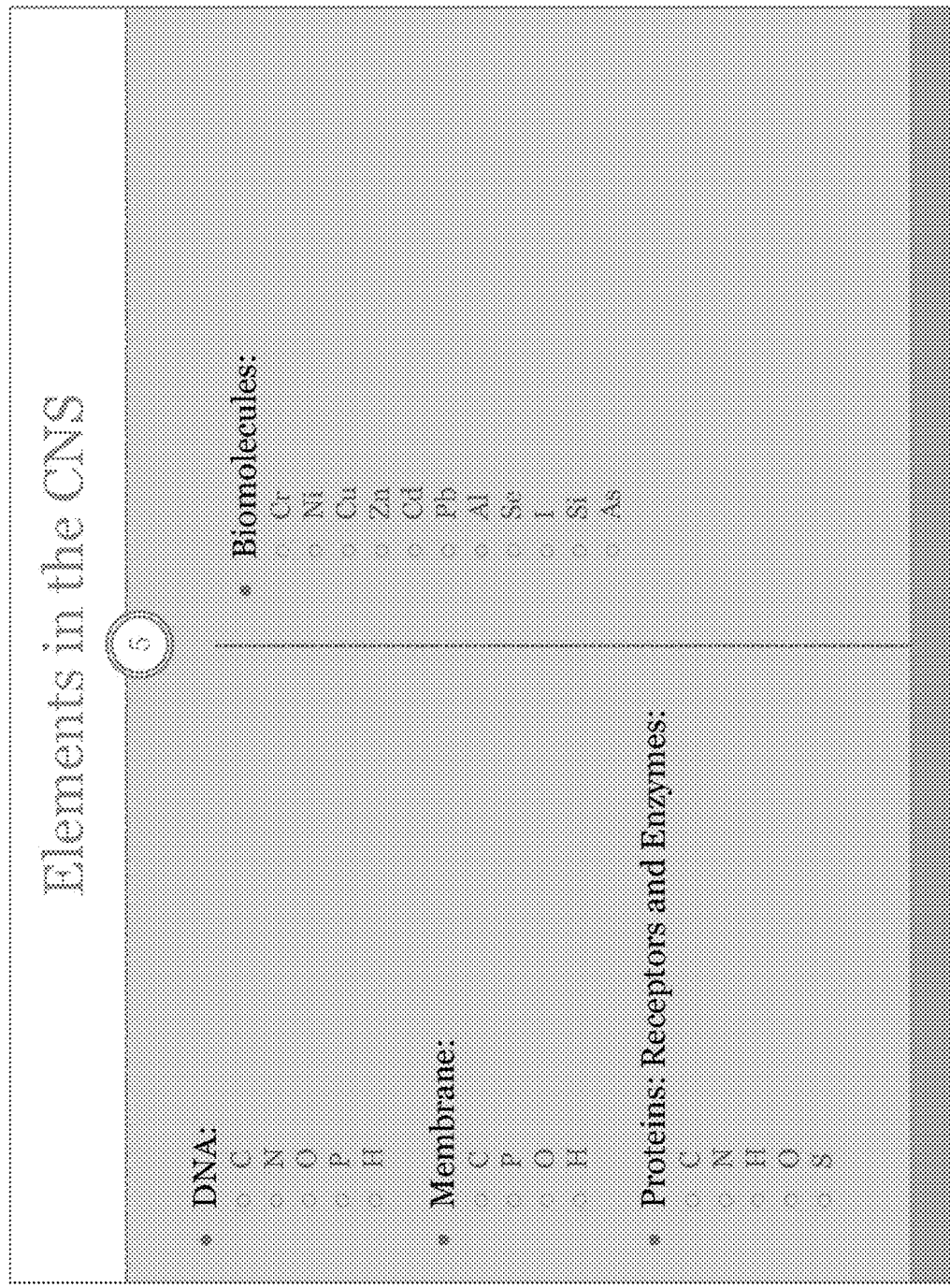
FIG. 33 illustrates examples of elements in the Central Nervous System (CNS).
Figure 36:
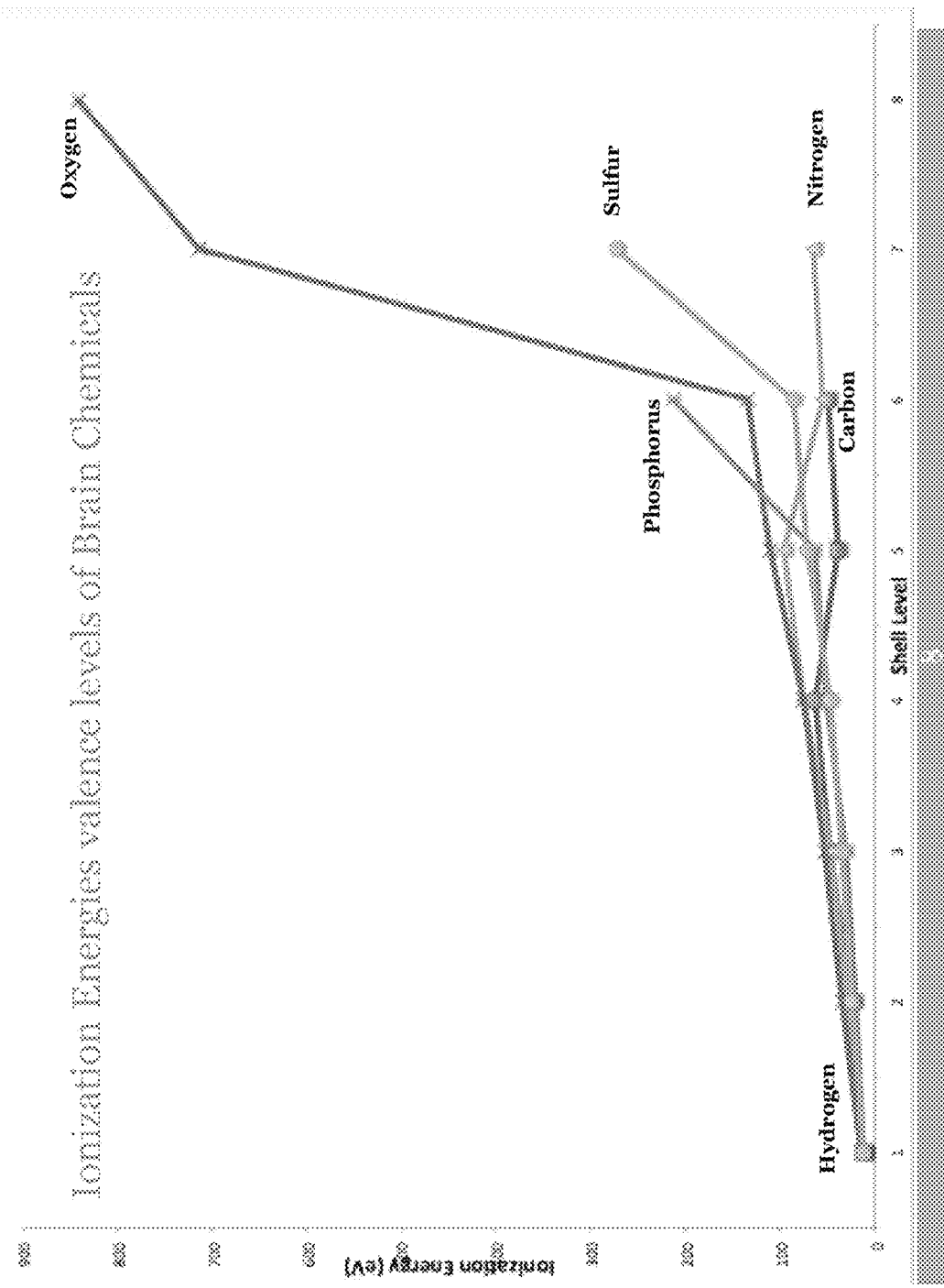
FIG. 36 illustrates examples of ionization energies valence levels of brain chemicals.
Figure 37:
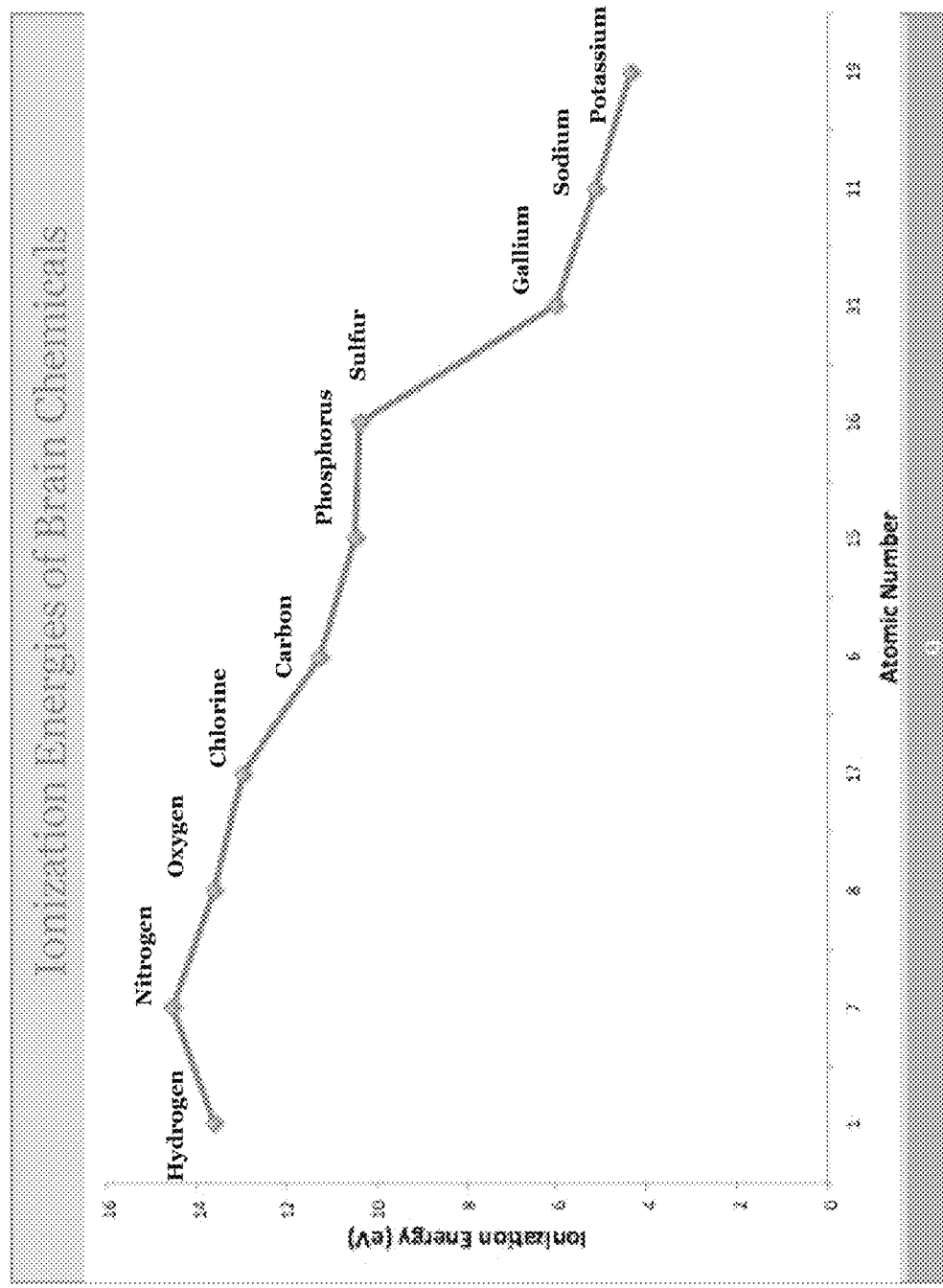
FIG. 37 illustrates examples of ionization energies of some brain chemicals.

An example of vibrational resonance is shown in FIG. 32. Examples of elements in the Central Nervous System (CNS) are shown in FIG. 33. An exemplary photo electric experiment is shown in FIG. 34. Examples of ionization energies of chemical elements are shown in FIG. 35. Examples of ionization energies valence levels of brain chemicals are shown in FIG. 36. Examples of ionization energies of brain chemicals are shown in FIG. 37.

Figure 38:
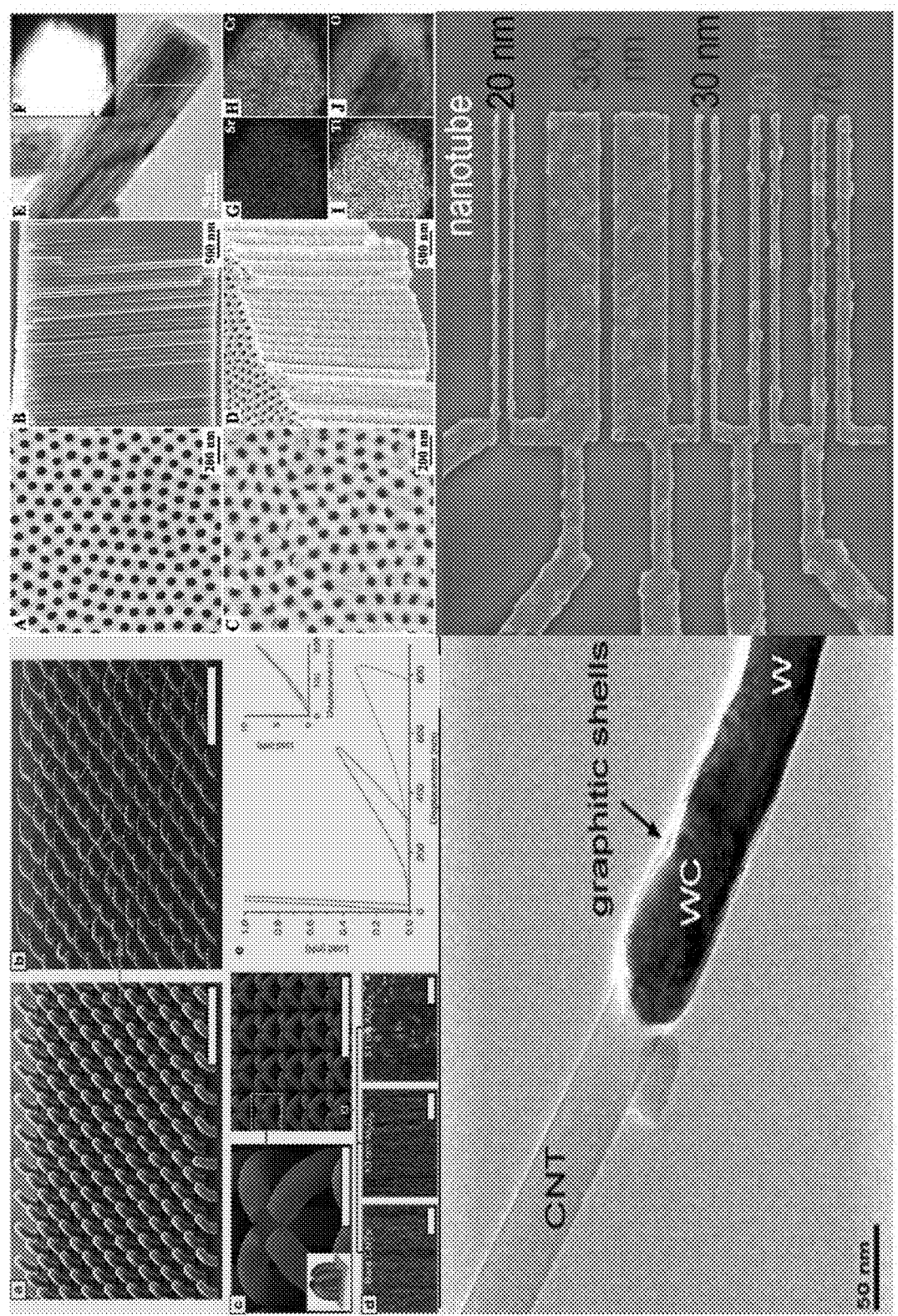
FIG. 38 illustrates examples of high resolution bi-directional optrodes, w/CNTs, and a 3D radial probe with a million CNTs.
Figure 39:
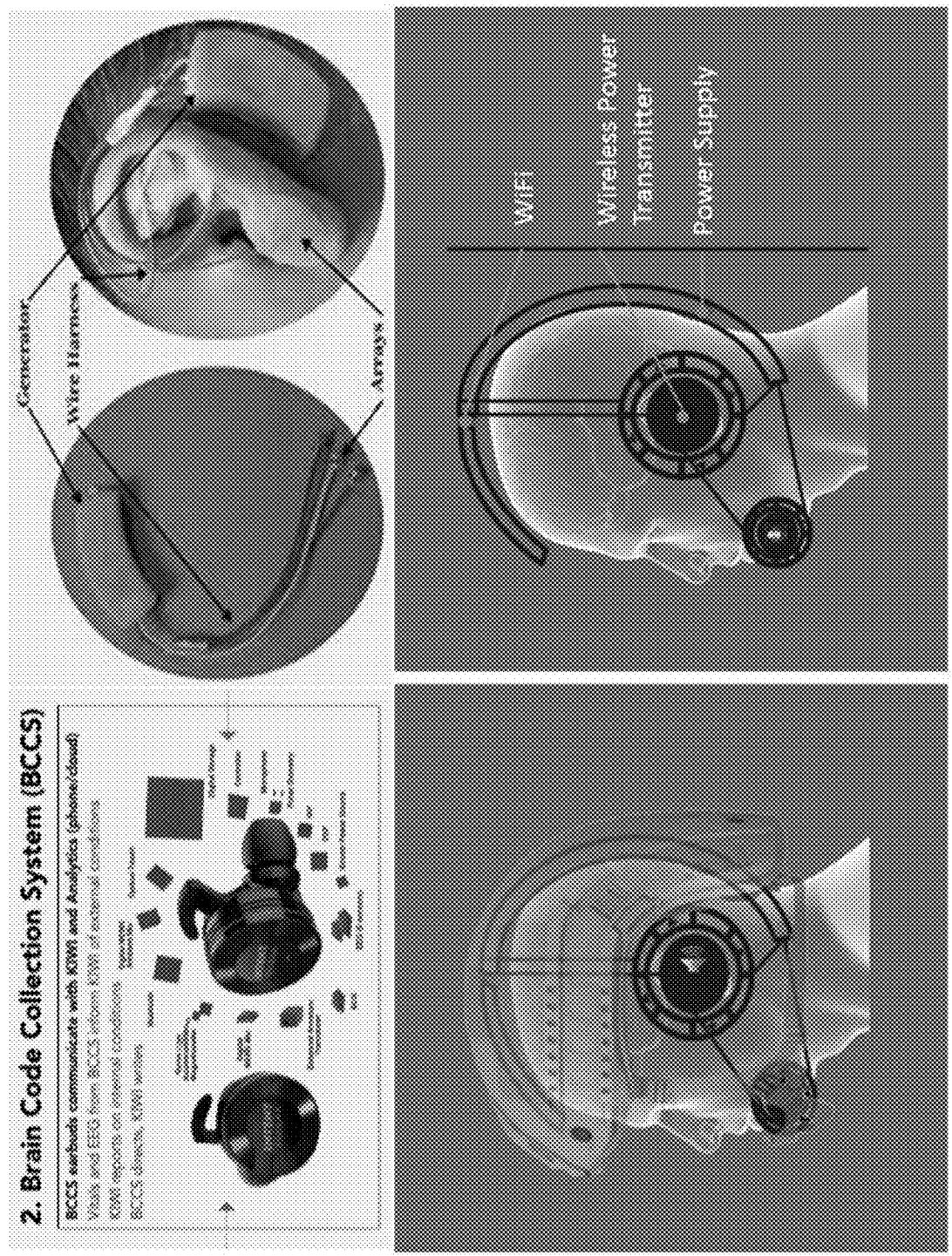
FIG. 39 illustrates an example of a 3D radial probe.

In embodiments, such as those shown in FIG. 13, a Biological Co-Processor (BCP) may include a closed-loop optoelectric neuromodulative system, wearable devices for psychological screening, real-time, full data capture and cloud-based analysis, and may be informed by internal and external conditions, for example, as captured by the wearable devices. In embodiments, the BCP may provide a neurodiagnostic system and/or a neurotherapeutic system. The BCP may map neuronal activity to behavior, context and vitals, map audial and prefrontal cortical activity to EEG, speech, lay groundwork for hearing augmentation and/or restoration, enhance cognitive skill learning with neurostimulation to promote synaptic plasticity, and may provide digital to brain (D2B) and brain to digital (B2D) conversion or transduction, such as thought to text, text to brain, etc. In embodiments, components of a BCP may include high resolution bi-directional optrodes, w/CNTs and may include a (Kiwi-inspired) 3D radial probe with a million CNTs, such as may be shown in FIG. 38. Such components may provide the capability to read from 1 million neurons, write to 100,000 neurons, and read/write bi-directionally to over 1,000 neurons. In embodiments, components of a BCP may include implantable wireless communications devices with inductive recharge into the implant and a Brain Code Collection System (BCCS), such as is shown in FIG. 39, which may include earbuds with EEG and key vitals to communicate with the implant. Embodiments may include system wide apps and API/SDK for smartphone/tablet and a secure cloud service to store and process all data.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry (such as that shown at 208 of FIG. 2) may include, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A system for interacting with living tissue comprising:
a device adapted to be attached to a body of a person or animal, adapted to transcribe signals from the living tissue, and adapted to transmit the transcribed signals, the device comprising a plurality of single wall nanotube carbon fibers, each single wall nanotube carbon fiber adapted to receive electrical signals from the living tissue, wherein at least some of the single wall nanotube carbon fibers are adapted to receive electrical signals from pyramidal layers II to VI of a brain cortex region, a processor adapted to receive the electrical signals and to process the electrical signals to form digital data representing the signals, and a transmitter adapted to transmit the digital data representing the signals wherein the device further comprises a receiver adapted to receive digital data representing signals to be applied to the living tissue and output control signals representing the signals to be applied to the living tissue, a plurality of light sources adapted to receive the control signals and output optical signals representing the control signals, and a plurality of optical fibers adapted to apply the optical signals to the living tissue, wherein the optical fibers are coated with single walled carbon nanotubes which adapt the optical fibers to receive electrical signals from the living tissue, wherein at least some of the optical fibers are adapted to receive electrical signals from pyramidal layers II to VI of a brain cortex region;
a processing device adapted to receive the transcribed signals, process the transcribed signals, and transmit the processed transcribed signals; and
a computer system adapted to receive the processed transcribed signals, store and further process the processed transcribed signals, and store other data related to the person or animal.

2. The system of claim 1 wherein the device further comprises delay lines between the plurality of carbon fibers and the coated optical fibers and the processing device, wherein the delay lines are adapted to compare time between pulses of the electrical signals.

3. The system of claim 1, wherein the light sources comprise vertical-cavity surface-emitting laser devices.

4. The system of claim 1 wherein the transmitter comprises a wireless transmitter.

5. The system of claim 1 wherein the device further comprises an inductively-recharged power source.

6. The system of claim 1 wherein:
the device is further adapted to be implanted within the body of the person or animal; and
the transcribed signals comprise neural signals from living brain or other neural tissue.

7. A method for interacting with living tissue comprising:
attaching a device to a body of a person or animal, the device comprising a plurality of single wall nanotube carbon fibers in contact with the living tissue, each single wall nanotube carbon fiber adapted to receive electrical signals from the living tissue, wherein at least some of the single wall nanotube carbon fibers are adapted to receive electrical signals from pyramidal layers II to VI of a brain cortex region;

receiving by the plurality of carbon fibers signals from the living tissue;

processing the received signals by the device;

transmitting the processed signals;

receiving digital data representing signals to be applied to the living tissue and outputting control signals representing the signals to be applied to the living tissue;

receiving, at a plurality of light sources, the control signals and outputting optical signals representing the control signals; and applying the optical signals to the living tissue with a plurality of optical fibers, wherein the optical fibers are coated with single walled carbon nanotubes which adapt the optical fibers to receive electrical signals from the living tissue, wherein at least some of the optical fibers are adapted to receive electrical signals from pyramidal layers II to VI of a brain cortex region.

8. The method of claim 7 further comprising comparing time between pulses of the electrical signal using delay lines coupled to the plurality of carbon fibers and the coated optical fibers.

9. The method of claim 7 wherein the light sources comprise vertical-cavity surface-emitting laser devices.

10. The system of claim 7 wherein the processed neural signals are transmitting using a wireless transmitter.

11. The method of claim 7 wherein:
the device is implanted within the body of the person or animal; and
the received signals comprise neural signals from living brain or other neural tissue.

12. A computer program product for controlling interaction with living tissue, the computer program product comprising a non-transitory computer readable storage having program instructions embodied therewith, the program instructions executable by a processor, to cause the processor to perform a method comprising:

receiving neural signals at a device attached to a body of a person or animal, the signals received from the living tissue using a plurality of single wall nanotube carbon fibers coupled to the device attached to the body of the person, the plurality of carbon fibers in contact with the living tissue, each single wall nanotube carbon fiber adapted to receive electrical signals from the living tissue, wherein at least some of the single wall nanotube carbon fibers are adapted to receive electrical signals from pyramidal layers II to VI of a brain cortex region;

processing the received signals by the device;

transmitting the processed signals;

receiving, at the device, digital data representing signals to be applied to the living tissue and outputting control signals representing the signals to be applied to the living tissue to a plurality of light sources at the implanted device;

receiving, at the plurality of light sources, the control signals and outputting optical signals representing the control signals to a plurality of optical fibers at the device; and applying the optical signals to the living tissue with a plurality of optical fibers, wherein the optical fibers are coated with single walled carbon nanotubes which adapt the optical fibers to receive electrical signals from the brain tissue, wherein at least some of the optical fibers are adapted to receive electrical signals from pyramidal layers II to VI of a brain cortex region.

13. The computer program product of claim 12 further comprising comparing time between pulses of the electrical signal using delay lines coupled to the plurality of carbon fibers and the coated optical fibers.

14. The computer program product of claim 12 wherein the light sources comprise vertical-cavity surface-emitting laser devices.

15. The computer program product of claim 12 wherein the processed signals are transmitting using a wireless transmitter.

16. The method of claim 12 wherein:
the device is implanted within the body of the person or animal; and
the received signals comprise neural signals from living brain or other neural tissue.

17. The system of claim 1, further comprising a gel or flesh membrane surrounding the plurality of single wall nanotube carbon fibers, wherein the gel or flesh membrane adapted to slowly dissolve when implanted, exposing the single wall nanotube carbon fibers to a cellular environment.

* * * * *